United States Patent
Ding et al.

(10) Patent No.: US 9,527,862 B2
(45) Date of Patent: Dec. 27, 2016

(54) COMPOUNDS OF CHIRAL AROMATIC SPIROKETAL DIPHOSPHINE LIGANDS, PREPARATION METHODS AND USES THEREOF

(71) Applicant: SHANGHAI INSTITUTE OF ORGANIC CHEMISTRY, CHINESE ACADEMY OF SCIENCES, Xuhui District, Shanghai (CN)

(72) Inventors: Kuiling Ding, Shanghai (CN); Xiaoming Wang, Shanghai (CN); Zhaobin Han, Shanghai (CN); Xubin Wang, Shanghai (CN); Zheng Wang, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 14/415,857

(22) PCT Filed: Jan. 29, 2013

(86) PCT No.: PCT/CN2013/071091
§ 371 (c)(1),
(2) Date: May 19, 2015

(87) PCT Pub. No.: WO2014/012371
PCT Pub. Date: Jan. 23, 2014

(65) Prior Publication Data
US 2015/0252055 A1 Sep. 10, 2015

(30) Foreign Application Priority Data

Jul. 20, 2012 (CN) .......................... 2012 1 0253476
Jul. 20, 2012 (CN) .......................... 2012 1 0253896

(51) Int. Cl.
| | | |
|---|---|---|
| C07D 491/20 | (2006.01) |
| C07D 493/10 | (2006.01) |
| C07D 493/20 | (2006.01) |
| C07F 9/6561 | (2006.01) |
| B01J 31/22 | (2006.01) |
| B01J 31/24 | (2006.01) |
| C07B 53/00 | (2006.01) |
| C07F 15/00 | (2006.01) |
| C07C 227/32 | (2006.01) |
| C07D 495/20 | (2006.01) |

(52) U.S. Cl.
CPC .......... *C07D 493/10* (2013.01); *B01J 31/2247* (2013.01); *B01J 31/2409* (2013.01); *C07B 53/00* (2013.01); *C07C 227/32* (2013.01); *C07D 491/20* (2013.01); *C07D 493/20* (2013.01); *C07D 495/20* (2013.01); *C07F 9/6561* (2013.01); *C07F 9/65616* (2013.01); *C07F 15/0033* (2013.01); *B01J 2231/32* (2013.01); *B01J 2531/0238* (2013.01); *B01J 2531/0261* (2013.01); *B01J 2531/824* (2013.01)

(58) Field of Classification Search
CPC ................ B01J 31/2247; B01J 31/2409; B01J 2531/0238; B01J 2531/0261; B01J 2531/824; C07F 9/6561; C07D 491/20; C07D 493/10; C07D 493/20
See application file for complete search history.

(56) References Cited

FOREIGN PATENT DOCUMENTS

| | | | |
|---|---|---|---|
| CN | 102424682 | * 4/2012 | ........... C07D 493/10 |
| CN | 102424682 A | 4/2012 | |
| CN | 102746338 A | 10/2012 | |

OTHER PUBLICATIONS

Wang, et al, Catalytic Asymmetric Synthesis of Aromatic Spiroketals by SpinPhox/Iridium(I)-Catalyzed Hydrogenation and Spiroketalization of α,α—-Bis(2-hydroxyarylidene) Ketones, Angewandte Chemie, vol. 51, Issue 4, pp. 936-940 (2011).*

Giancarlo Francio et al., Highly efficient enantioselective catalysis in supercritical carbon dioxide using the perfluoroalkyl-substituted ligand (R,S)-3-H2F6-BINAPHOS, J. of Organometallic Chem., Issue 621, pp. 130-142 (2001).*

Katritzky, et al., Comprehensive Organic Functional Group Transformations, vol. 2 (2003).*

Dimitri, et al., Copper-catalyzed C'P Bond Construction via Direct Coupling of Secondary Phosphines and Phosphites with Aryl and Vinyl Halides, Organic Letters, vol. 5, Issue 13, pp. 2315-2318 (2003).*

(Continued)

*Primary Examiner* — Erich A Leeser
(74) *Attorney, Agent, or Firm* — Panitch Schwarze Belisario & Nadel LLP

(57) ABSTRACT

Disclosed are aromatic spiroketal diphosphine ligands, preparation methods and uses thereof. The ligands have the structure of formula (I), in which $R^1$, $R^2$, $R^3$, $R^4$, $R^5$, $R^6$, $R^7$, $R^8$, X and n are defined as such described in the specification. The aromatic spiroketal diphosphine ligands are prepared from aromatic spiroketal compounds. Also disclosed are the preparation methods of aromatic spiroketal compounds. The preparation methods are simple and can produce racemic or chiral aromatic spiroketal diphosphine ligands. The ligands can be used as catalysts of asymmetrical catalytic reactions having economical practicability and industry application prospect

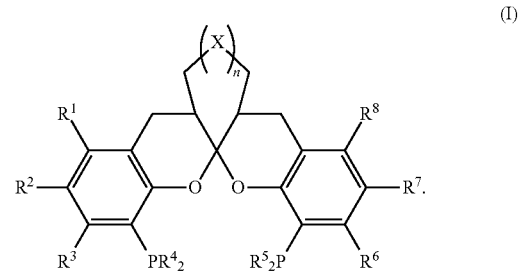

18 Claims, No Drawings

(56) References Cited

OTHER PUBLICATIONS

Int'l Search Report issued May 2, 2013 in Int'l Application No. PCT/CN2013/071091.
Wang et al, "Catalytic Asummetric Synthesis of Aromatic Spiroketals by SpinPhw/Iridium(I)-Catalyzed Hydrogenation and Spiroketalization of alpha, alpha'-Bis(2-hydroxyarylidene) Ketones," Angewante Chemie, International Ed., vol. 51, No. 4, pp. 936-940 (2012).
Giancarlo et al, "Highly efficient enantioselective catalysts in supercritical carbondioxide using the perfluoroalkyl-substituted ligand(R,S)-3-H2F6-BINAPHOS," Journal of Organometallic Chemistry, vol. 621, pp. 130-142 (2001).
Katritzky et al, "Comprehensive Organic Functional Group Transformations, vol. 2," Elsevier, pp. 826-827 (2003).
Gelman et al, "Copper-Catalyzed C—P Bond Construction via Direct Coupling of Secondary Phosphines and Phosphites with Aryl and Vinyl Halides," Organic Letters, vol. 5, No. 13, pp. 2315-2318 (2003).
Xin et al, "BF3-promoted cyclization reaction of imines and salicylaldehyde with silylenol ethers: unexpected formation of dioxaspiro compounds," tetrahedron, vol. 64, No. 39, pp. 9315-9319 (2008).
Xie et al, "Chiral Diphosphine and Monodentate Phosphorus Ligands on a Spiro Scaffold for Transition-Metal-Catalyzed Asymmetric Reactions," Accounts of Chemical Research, vol. 41, No. 5, pp. 581-593 (May 2008).
Qin et al, "Studies in the Total Synthesis of Heliquionomycinone: Proof of Concept and Assembly of a Fully Mature Spirocyclization Precursor," Angew. Chem. Int. Ed., vol. 40, No. 24, pp. 4709-4713 (2001).
Siu et al, "The Total Synthesis of Heliquinomycinone," Angew. Chem. Int. Ed., vol. 40, No. 24, pp. 4713-4716 (2001).
Freixa et al, "SPANphos: A C2-Symmetric trans-Coordinating Diphosphane Ligand," Angew. Chem. Int. Ed., vol. 42, No. 11, pp. 1284-1287 (2003).
Freixa et al, "Activity of SPANphos Rhodium Dimers in Methanol Carbonylation," Angew. Chem. Int. Ed., vol. 44, pp. 4385-4388 (2005).
Akai et al, "Total Synthesis of (+−)-gamma-Rubromycin on the Basis of Two Aromatic Pummerer-Type Reactions," Angew. Chem. Int. Ed., vol. 46, pp. 7458-7461 (2007).
Ding et al, "Spiro Skeletons: A Class of Privileged Structure for Chiral Ligand Design," Chem. Asian. J., vol. 4, pp. 32-41 (2009).
Li et al, "Spiro-2,2'-bichroman-based bisoxazoline (SPANbox) ligands for ZnII-catalyzed enantioselective hydroxylation of beta-keto esters and 1,3-diester," Chem. Sci., vol. 2, pp. 1141-1144 (2011).
Capecchi et al, "Synthesis of the bisbenzannelated sprioketal core of the gamma-rubromycins. The use of a novel Nef-type reaction mediated by Pearlman's catalyst," J. Chem. Soc., Perkin Trans., vol. I, pp. 2681-2688 (2000).
Caruso et al, "A New Reaction of Bisphenol A and Preparation of Polysubstituted 9,9-Dimethylxanthenes," J. Org. Chem., vol. 62, pp. 1058-1063 (1997).
Lindsey et al, "Synthesis of Electron Deficient 5,6-Aryloxy Spiroketals," Organic Letters, vol. 8, No. 11, pp. 2365-2367 (2006).
Sorgel et al, "Synthesis of Bisbenzannulated Spiroketals—Model Studies for a Modular Approach to Rubromycins," Organic Letters, vol. 8, No. 21, pp. 4875-4878 (2006).
Zhang et al, "Gold-Catalyzed Double Intromolecular Alkyne Hydroalkoxylation: Synthesis of the Bisbenzannelated Spiroketal Core of Rubromycins," Synlett, vol. 6, pp. 940-944 (2008).
Venkatesh et al, "Model Studies for the Synthesis of Heliquinomycin: Preparation of New Spiroketals," Synthesis, vol. 22, pp. 3605-3614 (2008).
Brimble et al, "A facile synthesis of fused aromatic sprioacetals based on the 3,4,3',4'-tetrahydro-2,2'-spriobis(2H-1-benzopyran) skeleton," Tetrahedron, vol. 62, pp. 5883-5896 (2006).
Capecchi et al, "Nitroalkenes as PRecursors to the Aromatic Spiroketal Skeleton of gamma-Rubromycin. A Nef-type Reaction Mediated by Pearlman's Catalyst," Tetrahedron Letters, vol. 39, pp. 5429-5432 (1998).
Zhou et al, "Expeditious synthesis of the aromatic spiroketal skeleton using hetero-Diels-Alder cycloaddition," Tetrahedron Letters, vol. 47, pp. 3349-3352 (2006).

* cited by examiner

COMPOUNDS OF CHIRAL AROMATIC SPIROKETAL DIPHOSPHINE LIGANDS, PREPARATION METHODS AND USES THEREOF

CROSS-REFERENCE TO RELATED APPLICATIONS

This application is a Section 371 of International Application No. PCT/CN2013/071091, filed Jan. 29, 2013, which was published in the Chinese language on Jan. 23, 2014, under International Publication No. WO 2014/012371 A1 and the disclosure of which is incorporated herein by reference.

BACKGROUND OF THE INVENTION

1. Technical Field

The present invention relates to the filed of organic chemistry, specially, to a chiral aromatic spiroketal bisphosphine ligand, preparation method and use thereof.

2. Background Art

Catalytic asymmetric synthesis is the research hotspot in the field of organic synthesis chemistry (Ohkuma, T.; Kitamura, M.; Noyori, R. 1999, Catalytic asymmetric synthesis. 2nd Ed.). Design and development of excellent chiral ligands and catalyst systems play a central role in asymmetric catalytic synthesis. Because chiral spirane structures (such as chiral aromatic spiroketals) have good rigid structure and formed transition metal complexes have advantages such as high stereoselectivity and chemical selectivity, etc. in asymmetric catalytic reactions, the studies on such ligands have received much attention from organic chemistry researcher (*Acc. Chem. Res.* 2008, 41, 581; *Chem. Asian J.* 2009, 4, 32.). In recent years, aromatic spiroketal ligands gradually got attention by people. For example, the complex formed from SPANPhos having benzodihydopyran backbone and metal rhodium showed good catalytic performance in the carbonylation of methanol for preparing formic acid (*Angew. Chem. Int. Ed* 2003, 42, 1284; *Angew. Chem. Int. Ed* 2005, 44, 4385). Another bisoxazoline ligand SPANBox having chiral aromatic spiroketal backbone has successfully been applied in asymmetric electrophilic hydroxylation of β-dicarbonyl compound catalyzed by Zn(II) (*Chem. Sci.* 2011, 2, 1141). However, the synthesis of benzodihydopyran backbone is relatively complicated and the yield is low. Moreover, it is difficult to adjust the backbone. Only racemic backbone can be obtained and further resolution is necessary to obtain optical pure backbone, which is not economic or environmentally friendly.

Chiral aromatic spiroketal is an important structure unit of natural products, bioactive compounds and chiral ligands. Reported methods includes spiroketalization of bisphenol hydroxy-ketone (or analogues) under the catalysis of acids (Tetrahedron Lett. 1998, 39, 5429; J. Chem. Soc., Perkin Trans. 1 2000, 2681; Org. Lett. 2006, 8, 4875; Tetrahedron 2006, 62, 5883; Synthesis 2008, 22, 3605), etherification of benzofuran under halogen (Angew. Chem. Int. Ed. 2001, 40, 4709), intramolecular addition reaction of hydroxy unsaturated bond catalyzed by transition metal (Synlett 2008, 940.), Mitsunobu reaction (Angew. Chem. Int. Ed. 2001, 40, 4713), aromatic Pumerer reaction (Angew. Chem. Int. Ed. 2007, 46, 7458), cycloaddition reaction (J. Org. Chem. 1997, 62, 1058; Org. Lett. 2006, 8, 2365; Tetrahedron Lett. 2006, 47, 3349) and so on. However, these methods are limited to synthesize racemic aromatic spiroketal products. Generally, the resolution of racemic aromatic spiroketal products is necessary to obtain optical pure chiral aromatic spiroketal compounds. The process is complicated and not economic or environmentally friendly.

It is necessary in the art to develop a novel aromatic spiroketal compound and a preparation method for chiral ligand, thereby obtaining racemates or compounds having optcal activity (opitcal pure) through simple reaction to avoid resolution.

BRIEF SUMMARY OF THE INVENTION

One object of the present invention is to provide a chiral aromatic spiroketal bisphosphine ligand, synthesis method and use thereof.

Another object of the present invention is to provide a preparation method for chiral aromatic spiroketal compounds.

In the first aspect of the present invention, a preparation method for a compound of formula I is provided, comprising the step of synthetizing the compound of formula I from a compound of formula II,

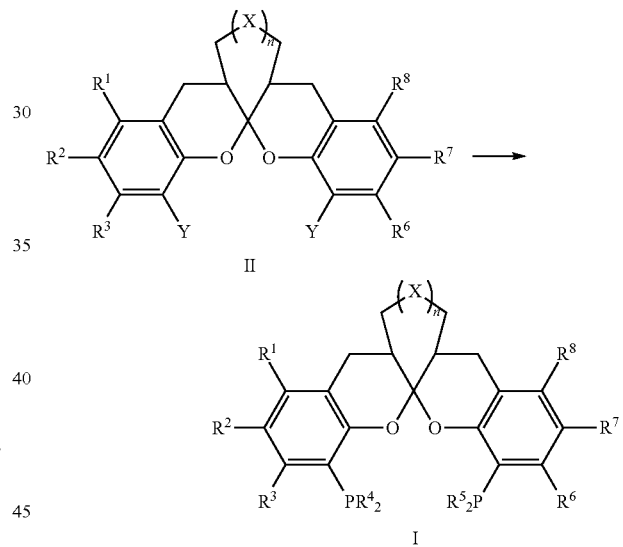

wherein $R^1$, $R^2$, $R^3$, $R^6$, $R^7$ and $R^8$ are independently selected from a hydrogen, a halogen, substituted or unsubstituted following groups: a $C_1$-$C_{10}$ alkyl, a $C_1$-$C_4$ alkoxyl, a $C_3$-$C_{30}$ cycloalkyl or an aryl;

$R^4$ and $R^5$ are independently selected from substituted or unsubstituted following groups: a $C_3$-$C_{10}$ cycloalkyl, a $C_1$-$C_{10}$ alkyl, 2-furyl, or an aryl;

X is selected from $CH_2$, NH, $NCH_3$, O or S; n=0-4;

wherein the substitution refers to be substituted by the following substituents: a halogen, a C1-6 alkyl, a C1-6 haloallcyl, or a C1-6 alkoxyl;

Y is F, Cl, Br or I.

In another preferred embodiment, $R^5$ are identical with $R^4$, and the method includes the steps:

(a1) a compound of formula II reacts with $R^4_2$POH in an organic solvent under the action of a metal catalyst to obtain a compound of formula III;

(b1) the compound of formula III is reduced to obtain the ligand,

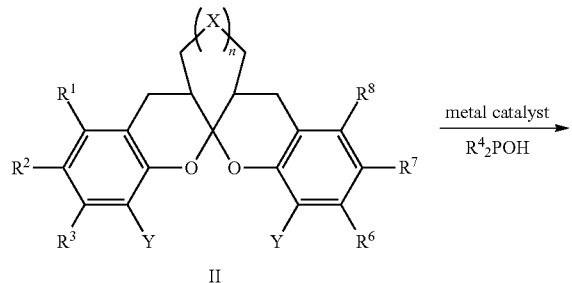

II

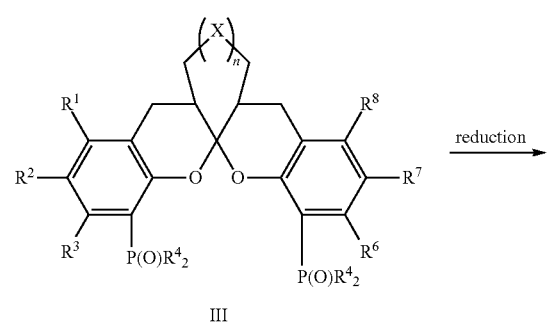

III

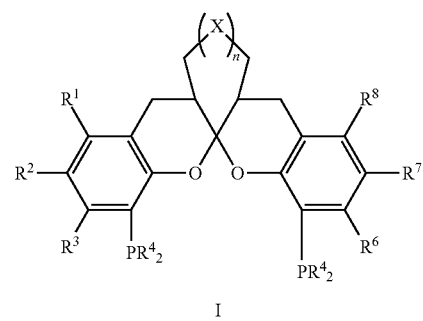

I or includes the step:

(a2) in an organic solvent and under the action of a base, Y group is removed from the compound of formula II and then the compound of formula II reacts with $R^4_2PCl$ or $R^4_2PBr$ to obtain the ligand,

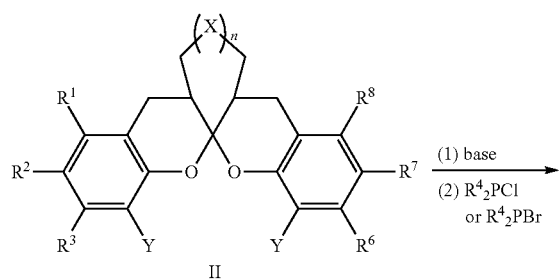

II

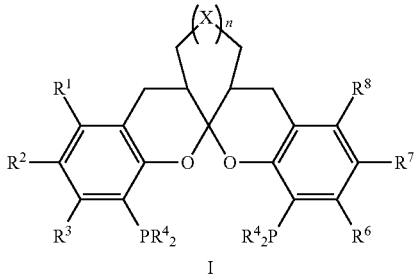

I or includes the step:

(a3) the compound of formula II reacts with $R^4_2PH$ in an organic solvent and under the action of a metal catalyst to obtain the ligand;

wherein Y is Cl, Br or I; $R^1$, $R^2$, $R^3$, $R^4$, $R^6$, $R^7$, $R^8$, X and n are defined as above.

In another preferred embodiment, in step (a2), the mole ratio of the base to the compound of formula II is 2:1-10:1; and the mole ratio of $R^4_2PCl$ or $R^4_2PBr$ to the compound of formula II is 2:1-10:1.

In another preferred embodiment, said metal catalyst is at least one selected from $Pd(OAc)_2$, $PdCl_2$, $Pd_2(dba)_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$, $dpppNiCl_2$, $Ni(PPh_3)_2Cl_2$, CuI, or a combination thereof.

In another preferred embodiment, in step (a3), the mole ratio of the metal catalyst to the compound of formula II is 0.001-0.5:1; the mole ratio of $R^4_2PH$ to the compound of formula II is 2-10:1. In another preferred embodiment, in step (a1), the mole ratio of the metal catalyst to the compound of formula II is 0.001-0.5:1; the mole ratio of $R^4_2POH$ to the compound of formula II is 2-10:1.

In another preferred embodiment, in step (b1), the reducing agent is selected from $HSiCl_3$, $(Me_2SiH)_2O$, LiAlH4, $(EtO)3SiH$, or a combination thereof.

In another preferred embodiment, said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof In another preferred embodiment, said base is selected from n-butyl lithium, tert-butyl lithium, cyclohexyl lithium, methyl lithium, isopropyl lithium, lithium bis(trimethylsilyl)amide, sodium bis(trimethylsilyl)amide, potassium bis(trimethylsilyl)amide, ethyl magnesium chloride, ethyl magnesium bromide, phenyl magnesium chloride, phenyl magnesium bromide.

In another preferred embodiment, $R^5$ is identical with $R^4$, and the method comprises the steps:

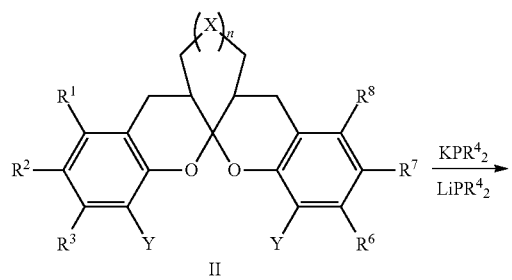

II the compound of formula II reacts with $KPR^4_2$ or $LiPR^4_2$ in an organic solvent to form the ligand, wherein Y is F; $R^1$, $R^2$, $R^3$, $R^4$, $R^6$, $R^7$, $R^8$, X and n are defined as above.

In another preferred embodiment, said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof In another preferred embodiment, the mole ratio of $KPR^4_2$ or $LiPR^4_2$ to the compound of formula II is 2:1-10:1.

In another preferred embodiment, the method comprises the steps:

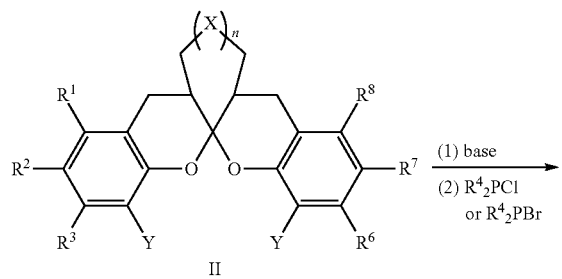

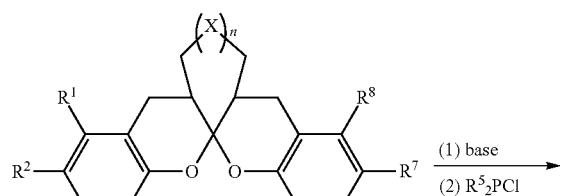

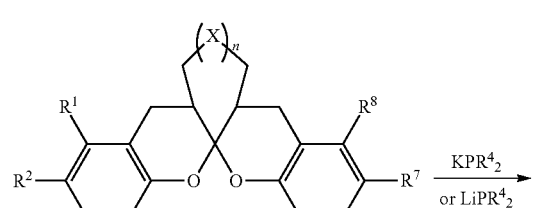

(i1) in an organic solvent, the compound of formula II reacts with a base and then reacts with $R^4_2PCl$ or $R^4_2PBr$ to form a compound of formula IV;

(ii1) the compound of formula IV reacts with a base and then reacts with $R^5_2PCl$ or $R^5_2PBr$ to form the ligand, wherein Y is Cl, Br or I;

$R^1$, $R^2$, $R^3$, $R^4$, $R^5$, $R^6$, $R^7$, $R^8$, X and n are defined as above, and $R^4 \neq R^5$;

or comprises the steps: (i2) in an organic solvent, the compound of formula II reacts with $KPR^4_2$ or $LiPR^4_2$ to form the compound of formula IV;

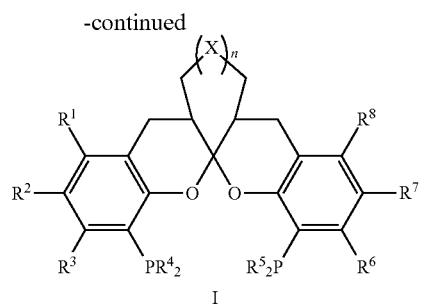

I (ii2) the compound of formula IV reacts with $KPR^5_2$ or $LiPR^5_2$ to form the ligand, wherein Y is F; $R^2$, $R^3$, $R^4$, $R^5$, $R^6$, $R^7$, $R^8$, X and n are defined as above, and $R4 \neq R5$.

In another preferred embodiment, in step (i1), the mole ratio of the base to the compound of formula II is 1:1-1.2:1; and the mole ratio of $R^4_2PCl$ or $R^4_2PBr$ to the compound of formula II is 1:1-1.2:1; and/or in step (ii1), the mole ratio of the base to the compound of formula IV is 1:1-1.2:1; and the mole ratio of $R^5_2PCl$ or $R^5_2PBr$ to the compound of formula IV is 1:1-1.2:1.

In another preferred embodiment, in step (i2), the mole ratio of $KPR^4_2$ or $LiPR^4_2$ to the compound of formula II is 1:1-1.2:1; and/or in step (ii2), the mole ratio of $KPR^5_2$ or $LiPR^5_2$ to the compound of formula IV is 1:1-1.2:1.

In another preferred embodiment, said organic solvent is one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof In another preferred embodiment, said base is selected from n-butyl lithium, tert-butyl lithium, cyclohexyl lithium, methyl lithium, isopropyl lithium, lithium bis(trimethylsilyl)amide, sodium bis(trimethylsilyl)amide, potassium bis(trimethylsilyl)amide, ethyl magnesium chloride, ethyl magnesium bromide, phenyl magnesium chloride, phenyl magnesium bromide.

In the second aspect of the present invention, a ligand is provided, having a structure as shown in general formula I:

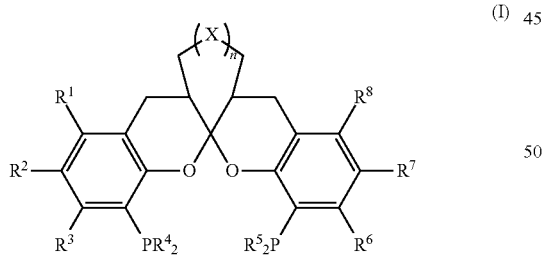

(I)

wherein,
$R^1$, $R^2$, $R^3$, $R^6$, $R^7$ and $R^8$ are independently selected from a hydrogen, a halogen, substituted or unsubstituted following groups: a $C_1$-$C_{10}$ alkyl, a $C_1$-$C_4$ alkoxyl, a $C_3$-$C_{30}$ cycloalkyl or an aryl;
$R^4$ and $R^5$ are independently selected from substituted or unsubstituted following groups: a $C_3$-$C_{10}$ cycloalkyl, a $C_1$-$C_{10}$ alkyl, 2-furyl, or an aryl; X is selected from $CH_2$, NH, $NCH_3$, O or S; n=0-4;
wherein the substitution refers to be substituted by the following substituents: a halogen, a $C_{1-6}$ alkyl, a $C_{1-6}$ haloalkyl, or a $C_{1-6}$ alkoxyl, "aryl" includes but not limited to phenyl, phenylene, naphthyl, naphthalene, pyrenyl, anthryl, phenanthryl.

In another preferred embodiment, the ligand is prepared according to the method of the first aspect.

In another preferred embodiment, when all of $R^1$, $R^2$, $R^3$, $R^6$, $R^7$ and $R^8$ are hydrogen, X is $CH_2$ and n=1, not both of $R^4$ and $R^5$ are phenyl.

In another preferred embodiment, not both of $R^4$ and $R^5$ are phenyl.

In another preferred embodiment, $R^1$, $R^2$, $R^3$, $R^6$, $R^7$ and $R^8$ are independently selected from a hydrogen, a $C_1$-$C_6$ alkyl, a $C_1$-$C_4$ alkoxyl, a $C_3$-$C_{10}$ cycloalkyl, a phenyl or a halogen;

$R^4$, $R^5$ are independently selected from a phenyl or a substituted phenyl, a $C_3$-$C_6$ cycloalkyl or a $C_2$-$C_6$ alkyl, and the substitution is mon-substituted, di-substituted or tri-substituted by the following substituents: a halogen, a $C_{1-6}$ alkyl, a $C_{1-6}$ haloalkyl, or a $C_{1-6}$ alkoxyl;

X is selected from $CH_2$, O, $NCH_3$ or S. Preferably, when all of $R^1$, $R^2$, $R^3$, $R^6$, $R^7$ and $R^8$ are hydrogen, X is $CH_2$ and n=1, not both of $R^4$ and $R^5$ are phenyl. More preferably, not both of $R^4$ and $R^5$ are phenyl.

In another preferred embodiment, the ligand is any one selected from compounds of formulae 6a~6w, or enantiomers, racemates or diastereoisomers of the compounds of formulae 6a~6w:

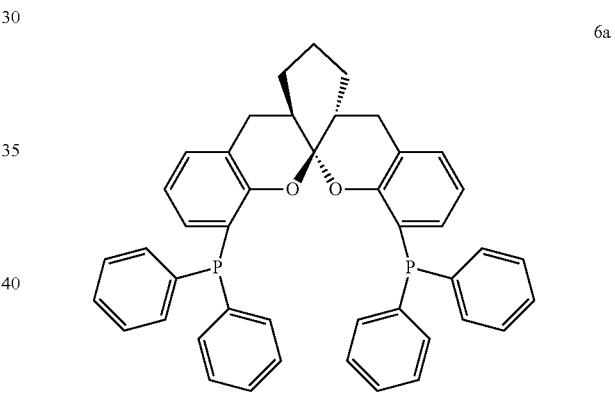

6a

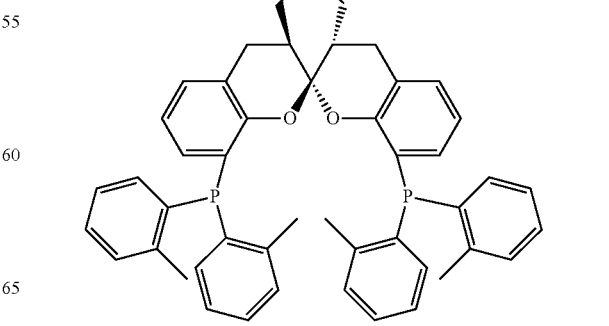

6b

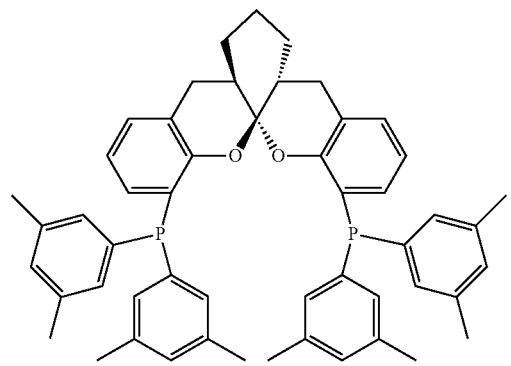
6c
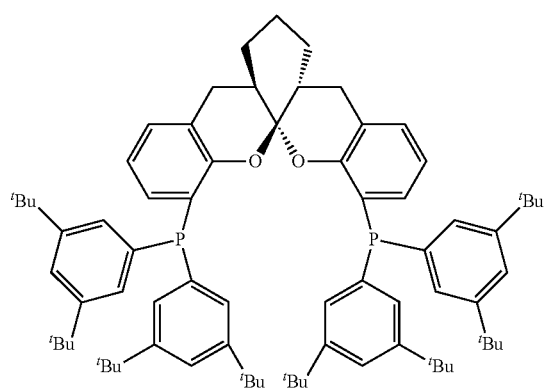
6d
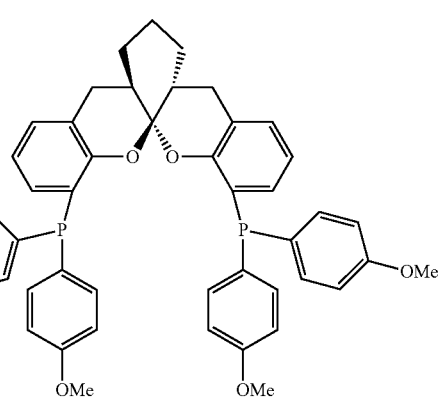
6g
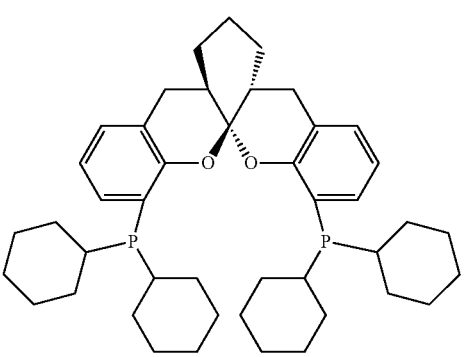
6h
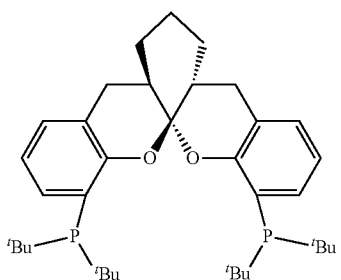
6i
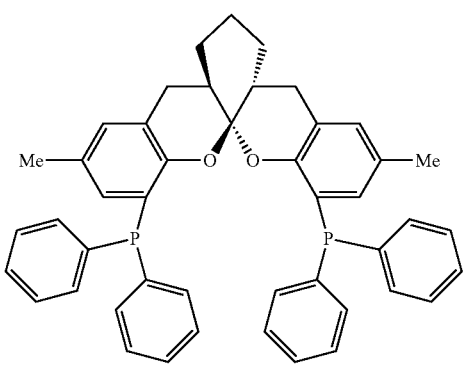
6j

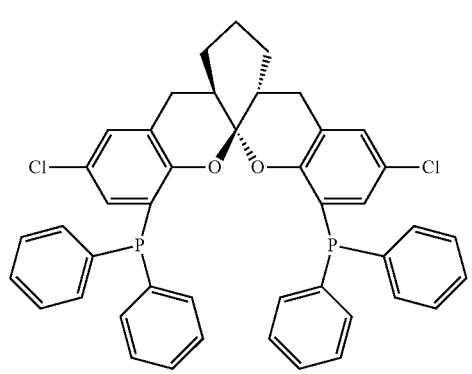
6k
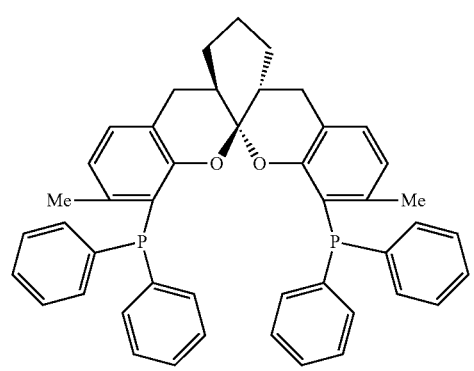
6l
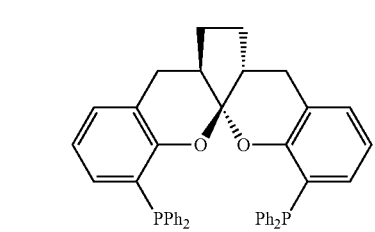
6m
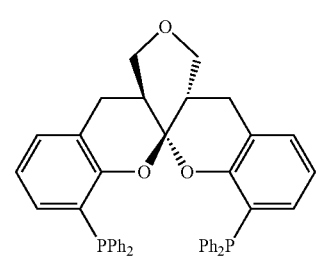
6n
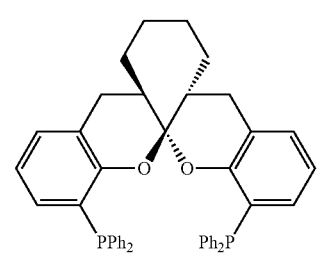
6o
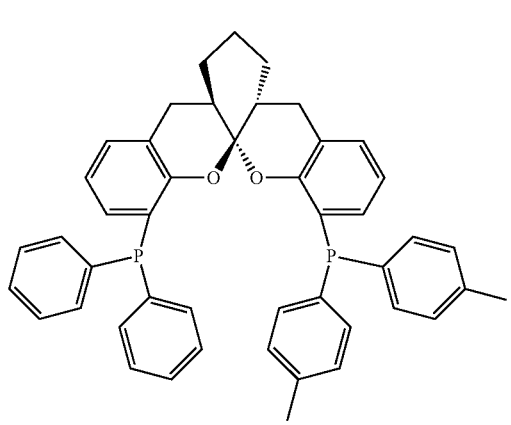
6p
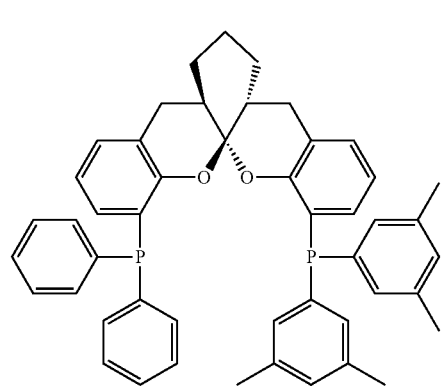
6q
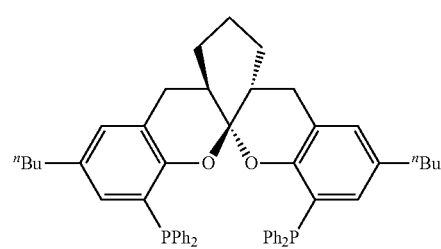
6r
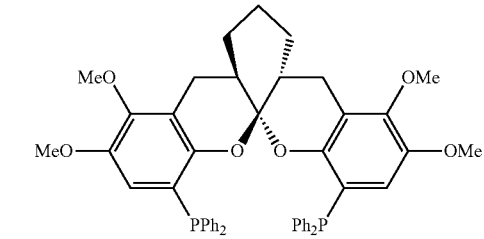
6s
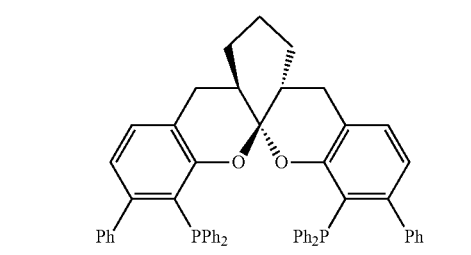
6t -continued

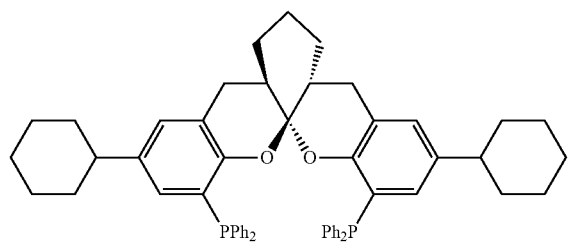
6u

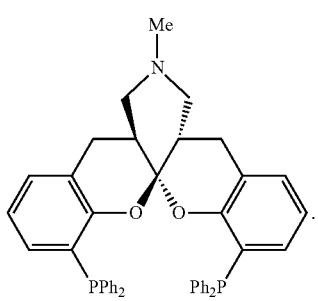
6v

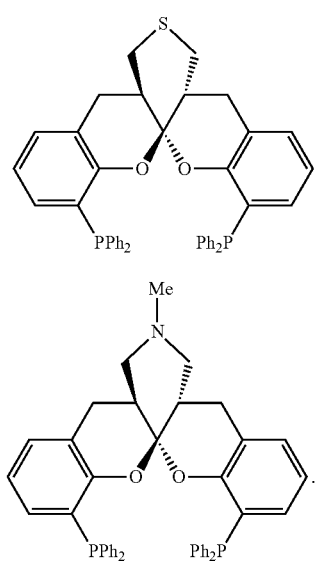
6w

In the third aspect of the present invention, a use of the ligand of the second aspect is provided, for a catalyst or for synthesizing a catalyst.

In another preferred embodiment, the complex formed from the ligand and a metal is used as the catalyst.

In another preferred embodiment, the catalyst is a catalyst used for asymmetric catalytic reaction.

In the fourth aspect of the present invention, a preparation method for chiral aromatic spiroketal compounds is provided, comprising the following steps:

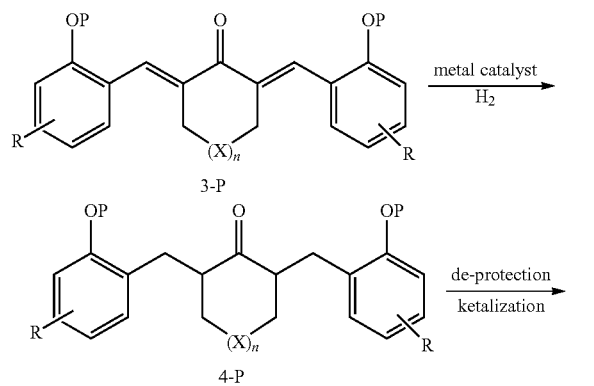

-continued

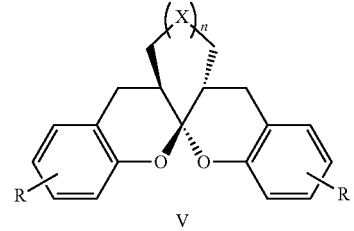
V (a) under hydrogen atmosphere, a compound of formula 3-P as a substrate is subjected to catalytic hydrogenation in an organic solvent by using a metal complex as a catalyst to obtain a hydrogenated product, a compound of formula 4-P;

(b) protecting groups are removed from the compound of formula 4-P, and then the compound is subjected to ketalization to obtain a chiral aromatic spiroketal compound, wherein the chiral aromatic spiroketal compound is a compound of general formula V or an enantiomer, racemate or diastereoisomer thereof, wherein, X is selected from $CH_2$, NH, $NCH_3$, O or S; n=0-4; R on the left is one or more of $R^{11}$, $R^{12}$, $R^{13}$ and $R^{14}$, R on the right is one or more of $R^{15}$, $R^{16}$, $R^{17}$ and $R^{18}$, and $R^{11}$, $R^{12}$, $R^{13}$, $R^{14}$, $R^{15}$, $R^{16}$, $R^{17}$ and $R^{18}$ are independently selected from a hydrogen, a $C_1$-$C_{10}$ alkyl, a $C_1$-$C_4$ alkoxyl, a $C_3$-$C_{30}$ cycloalkyl, a halogen or an aryl;

P is a methyl, a benzyl, a p-methoxy benzyl, a tert-butyl, a tert-butyldimethylsilyl, a tert-butyldiphenylsilyl, an allyl, a methoxymethyl, a methylthiomethyl, a methoxyethoxymethyl, a benzyloxymethyl, a tetrahydro 2-pyranyl or ester group.

In another preferred embodiment, the mole ratio of the compound of formula 3-P to the metal complex catalyst is 10000:1-10:1.

In another preferred embodiment, the metal complex is a complex of metal rhodium, ruthenium, palladium or iridium.

In another preferred embodiment, the metal complex is a complex of phosphine-nitrogen ligand and iridium.

In another preferred embodiment, the catalytic hydrogenation reaction is carried out under 1-100 normal atmospheric pressure of hydrogen at −78-80° C. for 1-48 hrs.

In another preferred embodiment, said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide.

In another preferred embodiment, separation and purification can be carried out during the process from 4-P to V or from 3-P to 4-P to V. Alternatively, the reaction can be finished in one-pot without separation.

DETAILED DESCRIPTION OF THE INVENTION

It should be understood that, within the scope of the present invention, the technical features specifically described above and below (such as the Examples) can be combined with each other, thereby constituting a new or preferred technical solution which needs not be described one by one.

Specific Mode for Carrying out the Invention

Upon extensive and in-depth research, chiral or racemic aromatic spiroketal bisphosphine ligands are prepared by the inventors of the present application using a simple reaction, so as to avoid resolution. Moreover, the ligand can be used as a catalyst in asymmetric catalytic reaction and has economic utility and industrial application prospect.

Term

The term "alkyl" refers to a saturated linear or branched chain-hydrocarbon moiety, such as —CH$_3$ or —CH(CH$_3$)$_2$. The term "alkoxy" refers to a group generated from binding an alkyl and oxygen atom, such as —OCH$_3$, —OCH$_2$CH$_3$. The term "cycloalkyl" refers to a saturated cyclic hydrocarbon moiety, such as cyclohexyl. The term "aryl" means a hydrocarbon moiety containing one or more aromatic rings, including but not limited to phenyl, phenylene, naphthyl, naphthalene, pyrenyl, anthryl, phenanthryl and benzyl.

Unless otherwise specified, the alkyl, alkoxy, cycloalkyl and aryl described herein include substituted or unsubstituted moieties. Feasible substituents on the alkyl, alkoxy, cycloalkyl and aryl may include, but are not limited to: a $C_1$-$C_6$ alkyl, a $C_1$-$C_6$ haloalkyl, a $C_2$-$C_6$ alkenyl, a $C_2$-$C_6$ alkynyl, a $C_3$-$C_{10}$ cycloalkyl, a $C_3$-$C_{10}$ cycloalkenyl, a $C_1$-$C_6$ alkoxy, an aryl, a hydroxy, a halogen, an amino.

Preparation Method for Aromatic Spiroketal Compounds

The preparation method for aromatic spiroketal compounds according to the present invention comprises the following steps:

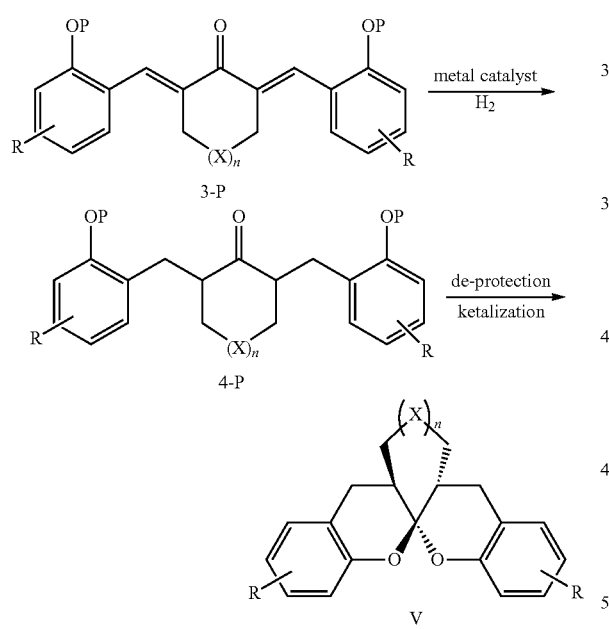

(a) under hydrogen atmosphere, a compound of formula 3-P as a substrate is subjected to catalytic hydrogenation by using a metal complex as catalyst in an organic solvent to obtain hydrogenated product, a compound of formula 4-P;

(b) the protecting groups are removed from the compound of formula 4-P, and then the compound is subjected to ketalization to obtain a chiral aromatic spiroketal compound, wherein the chiral aromatic spiroketal compound is the compound having general formula V or an enantiomer, racemate or diastereoisomer thereof, wherein X is selected from CH$_2$, NH, NCH$_3$, O or S; n=0-4; R on the left is one or more of $R^{11}$, $R^{12}$, $R^{13}$ and $R^{14}$, R on the right is one or more of $R^{15}$, $R^{16}$, $R^{17}$ and $R^{18}$, and $R^{11}$, $R^{12}$, $R^{13}$, $R^{14}$, $R^{15}$, $R^{16}$, $R^{17}$ and $R^{18}$ are independently selected from a hydrogen, a $C_1$-$C_{10}$ alkyl, a $C_1$-$C_4$ alkoxyl, a $C_3$-$C_{30}$ cycloalkyl, a halogen or an aryl;

P is a methyl, a benzyl, a p-methoxy benzyl, a tert-butyl, a tert-butyldimethylsilyl, a tert-butyldiphenylsilyl, an allyl, a methoxymethyl, a methylthiomethyl, a methoxyethoxymethyl, a benzyloxymethyl, a tetrahydro 2-pyranyl or ester group.

In another preferred embodiment, the preparation method for aromatic spiroketal compounds according to the present invention comprises the following steps:

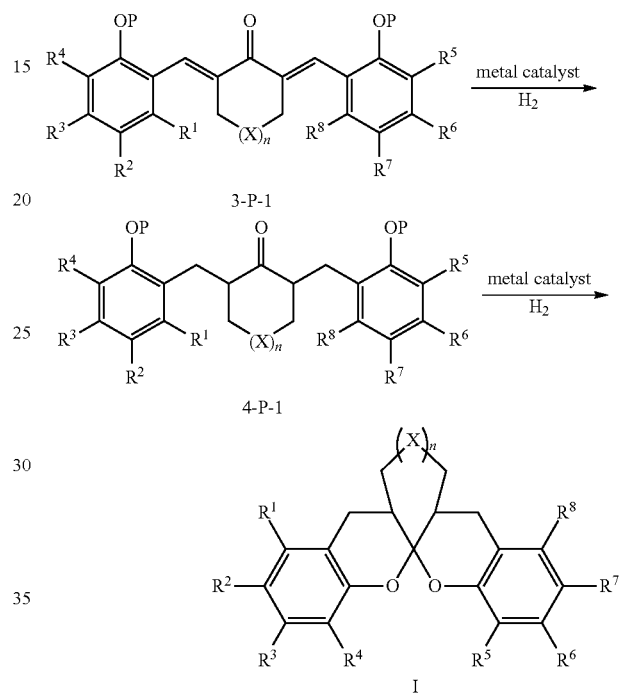

(a') under hydrogen atmosphere, a compound of formula 3-P-1 as a substrate is subjected to catalytic hydrogenation in an organic solvent by using metal complex as catalyst to obtain hydrogenated product, a compound of formula 4-P-1;

(b') the protecting groups are removed from the compound of formula 4-P-1, and then the compound is subjected to ketalization to obtain a chiral aromatic spiroketal compound, wherein $R^1$, $R^2$, $R^3$, $R^4$, $R^5$, $R^6$, $R^7$, $R^8$, X and n are defined as above.

In another preferred embodiment, the metal complex is chiral or non-chiral.

In another preferred embodiment, the metal complex is a complex of metal rhodium, ruthenium, palladium or iridium.

In another preferred embodiment, the metal complex is a complex of phosphine-nitrogen ligand and iridium.

In another preferred embodiment, in step (b) or step (b'), when P is a benzyl or a p-methoxylbenzyl, benzyl or a p-methoxylbenzyl can be removed through catalytic hydrogenation by using a metal catalyst in an organic solvent under hydrogen atmosphere.

In another preferred embodiment, in step (b) or step (b'), when P is a silyl protecting group (such as tert-butyldimethylsilyl (TBDMS), tert-butyldiphenylsilyl (TBDPS)), P can be removed in an organic solvent by using tetrabutylammonium fluoride, cesium fluoride, potassium fluoride, hydrofluoric acid pyridine complex.

In another preferred embodiment, in step (b) or step (b'), when P is an alkyl protecting group, P can be removed in an organic solvent by using boron tribromide, boron trifluoride in diethyl ether. The mole ratio of the compound of formula 3-P (or the compound of formula 3-P-1) to the metal complex catalyst is 10000:1-10:1, preferably 50:1-100:1.

The catalytic hydrogenation reaction is carried out under 1-100 normal atmospheric pressure of hydrogen at −78-80° C. for 1-48 hrs;
preferably, under 20-60 normal atmospheric pressure of hydrogen at 20-60° C. for 10-24 hrs.

The compound of formula 4-P (or the compound of formula 4-P-1) is subjected to de-protection and then automatically ketalization, or is subjected to acidation by adding an acid and then ketalization, to form a chiral aromatic spiroketal compound. The acid is preferably hydrochloric acid, sulfuric acid, p-toluenesulfonic acid, phosphoric acid, acetic acid, trifluoroacetic acid, aluminium trichloride, boron trifluoride, iridium trichloride, copper trifluoromesylate, zinc trifluoromesylate, tin tetrachloride.

Said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide.

The Aromatic spiroketal compound prepared by above method can further be derived to prepare racemic or chiral aromatic spiroketal bisphosphine ligand to be used as a catalyst in asymmetric catalytic reaction.

Ligand

The ligand according to the present invention has a structure as shown in general formula I:

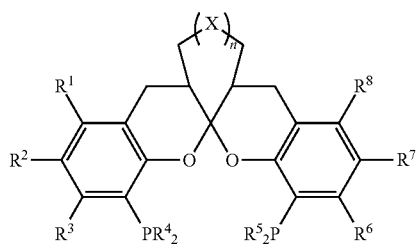

(I)

wherein $R^1$, $R^2$, $R^3$, $R^6$, $R^7$, $R^8$ are independently selected from a hydrogen, a halogen, substituted or unsubstituted following groups: a $C_1$-$C_{10}$ alkyl, $C_1$-$C_4$ alkoxyl, a $C_3$-$C_{30}$ cycloalkyl or an aryl;
  $R^4$ and $R^5$ are independently selected from substituted or unsubstituted following groups: a $C_3$-$C_{10}$ cycloalkyl, a $C_1$-$C_{10}$ alkyl, 2-furyl or a phenyl; X is selected from $CH_2$, NH, $NCH_3$, O or S; n=0-4;
  wherein the substitution refers to be substituted by the following substituents: a halogen, a $C_{1-6}$ alkyl, a $C_{1-6}$ haloalkyl, or a $C_{1-6}$ alkoxyl.

The additional condition is that not both of $R^4$ and $R^5$ are phenyl.

In another preferred embodiment, the aryl is selected from phenyl, phenylene, naphthyl, naphthalene, pyrenyl, anthryl, phenanthryl.

In another preferred embodiment, $R^4$ and $R^5$ are the same groups.

In another preferred embodiment, the substitution is mon-substituted, di-substituted or tri-substituted by the following substituents: a halogen, a $C_{1-6}$ alkyl, a $C_{1-6}$ haloalkyl, or a $C_{1-6}$ alkoxyl. In another preferred embodiment, the ligand is a compound of formula Ia, a compound of formula Ib, a compound of formula Ic or a compound of formula Id with the following structures:

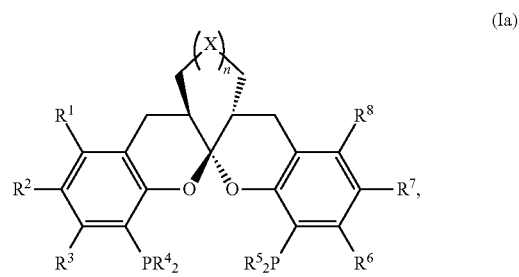

(Ia)

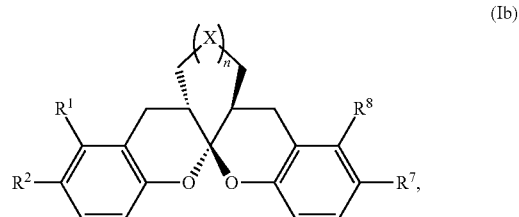

(Ib)

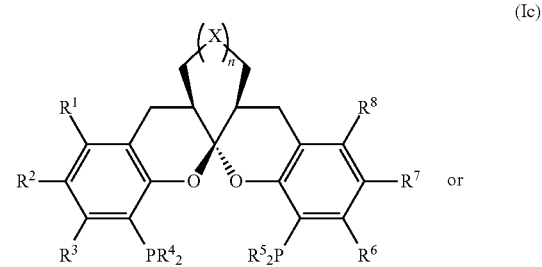

(Ic) or

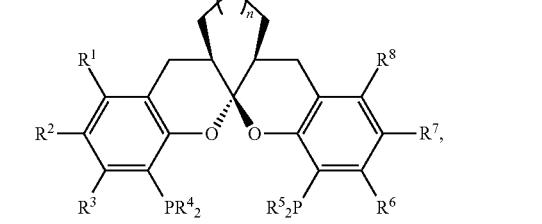

(Id)

wherein $R^1$, $R^2$, $R^3$, $R^4$, $R^5$, $R^6$, $R^7$, $R^8$, X and n are defined as above.

In another preferred embodiment, the ligand contains a compound of formula Ia and a compound of formula Ib.

In another preferred embodiment, the ligand contains a compound of formula Ic and a compound of formula Id.

In another preferred embodiment, $R^1$, $R^2$, $R^3$, $R^6$, $R^7$ and $R^8$ are independently selected from a hydrogen, a $C_1$-$C_6$ alkyl, a $C_1$-$C_4$ alkoxyl, a $C_3$-$C_{10}$ cycloalkyl, a phenyl or a halogen;

$R^4$ and $R^5$ are independently selected from a phenyl or a substituted phenyl, a $C_3$-$C_6$ cycloalkyl or a $C_2$-$C_6$ alkyl, and the substitution is mon-substituted, di-substituted or tri-substituted by the following substituents: a halogen, a $C_{1-6}$ alkyl, a $C_{1-6}$ haloalkyl, or a $C_{1-6}$ alkoxyl;

X is selected from $CH_2$, O, $NCH_3$ or S.

In another preferred embodiment, the ligand is any one selected from compounds of formulae 6b~6w, or enantiomers, racemates or diastereoisomers of the compounds of formulae 6b~6w. The racemate refers to a racemate composed of any one of the compounds of formulae 6b~6w and enantiomer thereof Preparation Method The preparation method for the ligand according to the present invention comprises the step of synthetizing the ligand from the compound of formula II,

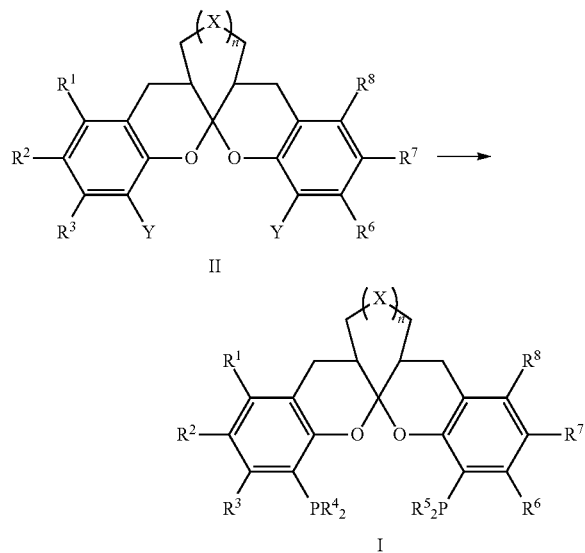

wherein $R^1$, $R^2$, $R^3$, $R^4$, $R^5$, $R^6$, $R^7$, $R^8$, X and n are defined as above, and Y is F, Cl, Br or I.

In another preferred embodiment, $R^5$ and $R^4$ are the same, and the method comprises the following steps:

(a1) the compound of formula II reacts with $R^4_2POH$ in an organic solvent under the action of a metal catalyst to form the compound of formula III;

(b1) the compound of formula III is reduced to obtain the ligand;

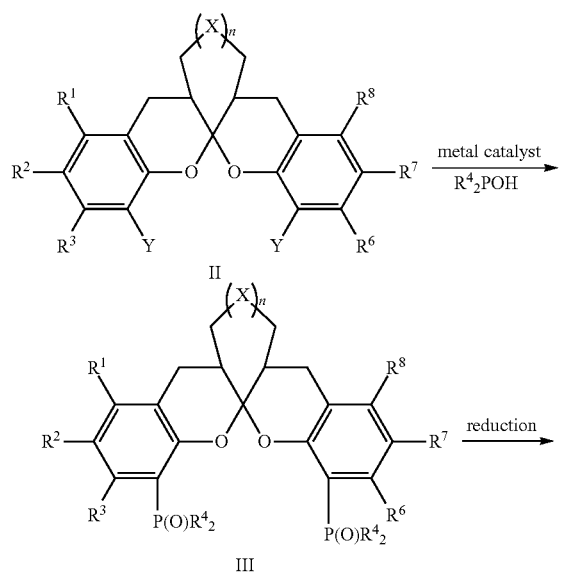

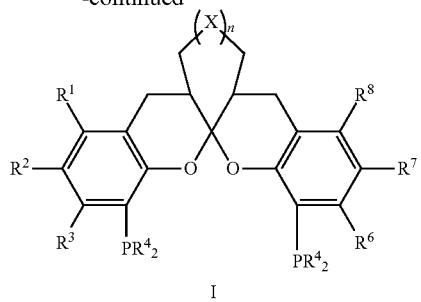

wherein Y is Cl, Br or I; $R^1$, $R^2$, $R^3$, $R^4$, $R^6$, $R^7$, $R^8$, X and n are defined as above.

In another preferred embodiment, said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof.

In another preferred embodiment, the metal catalyst is at least one selected from $Pd(OAc)_2$, $PdCl_2$, $Pd_2(dba)_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$, dpppNiCl$_2$, $Ni(PPh_3)_2Cl_2$, CuI or a combination thereof.

In another preferred embodiment, the metal catalyst is $Pd(OAc)_2$ or $Pd(PPh_3)_4$.

In another preferred embodiment, in step (a1), the mole ratio of the metal catalyst to the compound of formula II is 0.001-0.5:1, and the mole ratio of $R^4_2POH$ to the compound of formula II is 2-10:1.

In another preferred embodiment, the mole ratio of the metal catalyst to the compound of formula II in step (a1) is 0.005-0.1:1, preferably 0.01-0.05:1.

In another preferred embodiment, the mole ratio of $R^4_2POH$ to the compound of formula II in step (a1) is 2-6:1, preferably, 2-3:1.

In another preferred embodiment, the reaction temperature in step (a1) is 0° C.-150° C., preferably, 60° C.-100° C. The reaction time is 1-48 hrs, preferably, 6-12 hrs.

In another preferred embodiment, the reducing agent used in step (b1) is one selected from $HSiCl_3$, $(Me_2SiH)_2O$, $LiAlH_4$, $(EtO)_3SiH$ or a combination thereof.

In another preferred embodiment, the reducing agent is $HSiCl_3$.

In another preferred embodiment, the reaction temperature in step (b1) is 0° C.-150° C. The reaction time is 1-48 hrs.

In another preferred embodiment, $R^5$ and $R^4$ are the same and the method comprises the steps:

(a2) Y group is removed from the compound of formula II and then the compound reacts with $R^4_2PCl$ or $R^4_2PBr$ in an organic solvent under the action of a base to obtain the ligand;

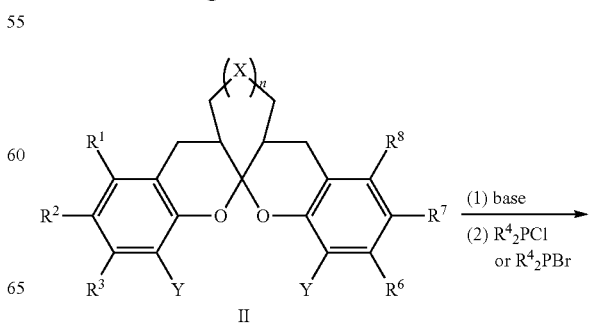

-continued

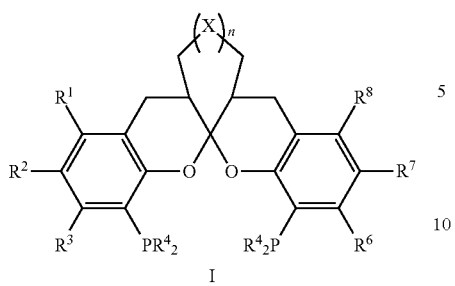

wherein Y is Cl, Br or I; $R^1$, $R^2$, $R^3$, $R^4$, $R^6$, $R^7$, $R^8$, X and n are defined as above.

In another preferred embodiment, said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof.

In another preferred embodiment, said base is selected from n-butyl lithium, tert-butyl lithium, cyclohexyl lithium, methyl lithium, isopropyl lithium, lithium bis(trimethylsilyl)amide, sodium bis(trimethylsilyl)amide, potassium bis(trimethylsilyl)amide, ethyl magnesium chloride, ethyl magnesium bromide, phenyl magnesium chloride, phenyl magnesium bromide.

In another preferred embodiment, said base is n-butyl lithium or tert-butyl lithium.

In another preferred embodiment, in step (a2), the mole ratio of the base to the compound of formula II is 2:1-10:1; and the mole ratio of $R^4_2PCl$ or $R^4_2PBr$ to the compound of formula II is 2:1-10:1.

In another preferred embodiment, the mole ratio of the base to the compound of formula II in step (a2) is 2:1-6:1; preferably, 2:1-3:1.

In another preferred embodiment, the mole ratio of $R^4_2PCl$ or $R^4_2PBr$ to the compound of formula II in step (a2) is 2:1-6:1; preferably, 2:1-3:1.

In another preferred embodiment, in step (a2), the reaction temperature is −78° C.-100° C., preferably, −78° C.-60° C., more preferably, −78° C.-25° C., particularly preferably, −78° C.-0° C.; and the reaction time is 0.5 hr-48 hrs, preferably, 1 hr-24 hrs.

In another preferred embodiment, $R^5$ and $R^4$ are the same, and the method comprises the steps:

(a3) under the action of a metal catalyst, the compound of formula II reacts with $R^4_2PH$ in an organic solvent to obtain the ligand;

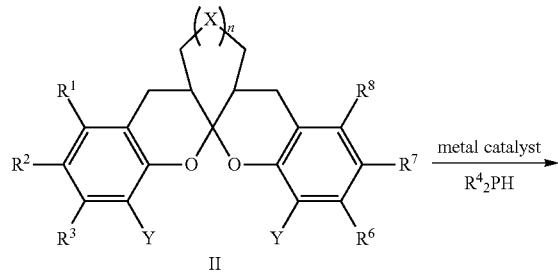

-continued

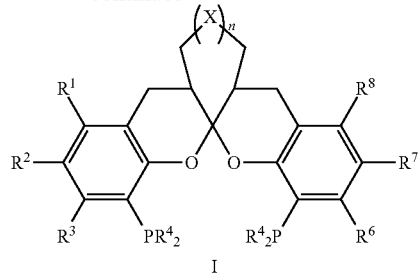

wherein Y is Cl, Br or I; and $R^1$, $R^2$, $R^3$, $R^4$, $R^6$, $R^7$, $R^8$, X and n are defined as above.

In another preferred embodiment, said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof.

In another preferred embodiment, the metal catalyst is at least one selected from $Pd(OAc)_2$, $PdCl_2$, $Pd_2(dba)_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$, dpppNiCl$_2$, Ni(PPh$_3$)$_2$Cl$_2$, CuI or a combination thereof.

In another preferred embodiment, the metal catalyst is $Pd(OAc)_2$ or $Pd(PPh_3)_4$.

In another preferred embodiment, in step (a3), the mole ratio of the metal catalyst to the compound of formula II is 0.001-0.5:1; and the mole ratio of $R^4_2PH$ to the compound of formula II is 2-10:1.

In another preferred embodiment, the mole ratio of the metal catalyst to the compound of formula II in step (a3) is 0.005-0.1:1, preferably, 0.01-0.05:1.

In another preferred embodiment, the mole ratio of $R^4_2PH$ to the compound of formula II in step (a3) is 2-6:1, preferably, 2~3:1.

In another preferred embodiment, in step (a3), the reaction temperature is 0° C.-150° C., preferably, 60° C.-100° C.; and the reaction time is 1 hr-48 hrs, preferably, 6-12 hrs.

In another preferred embodiment, $R^5$ and $R^4$ are the same, and the method comprises the steps:

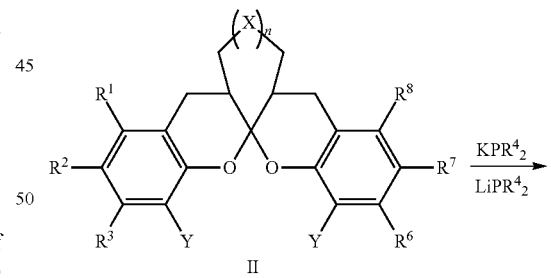

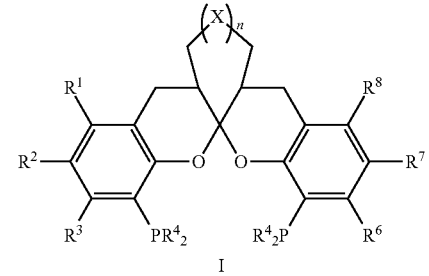

the compound of formula II reacts with KPR$^4_2$ or LiPR$^4_2$ in an organic solvent to form the ligand, wherein Y is F; and R$^1$, R$^2$, R$^3$, R$^4$, R$^6$, R$^7$, R$^8$, X and n are defined as above.

In another preferred embodiment, the mole ratio of KPR$^4_2$ or LiPR$^4_2$ to the compound of formula II is 2:1-10:1.

In another preferred embodiment, the mole ratio of KPR$^4_2$ or LiPR$^4_2$ to the compound of formula II is 2:1-6:1, preferably, 2:1-3:1.

In another preferred embodiment, KPR$^4_2$ or LiPR$^4_2$ can be prepared by corresponding phosphine compound and base on site.

In another preferred embodiment, reaction temperature is −78° C.-150° C., preferably, 20° C.-80° C., and reaction time is 0.5 hr-48 hrs, preferably, 6-10 hrs.

In another preferred embodiment, said organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof.

In another preferred embodiment, said base is selected from n-butyl lithium, tert-butyl lithium, cyclohexyl lithium, methyl lithium, isopropyl lithium, lithium bis(trimethylsilyl)amide, sodium bis(trimethylsilyl)amide, potassium bis(trimethylsilyl)amide, ethyl magnesium chloride, ethyl magnesium bromide, phenyl magnesium chloride, phenyl magnesium bromide.

In another preferred embodiment, said base is n-butyl lithium or tert-butyl lithium.

In another preferred embodiment, the method comprises the steps:

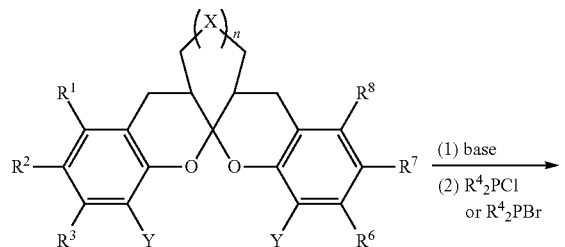

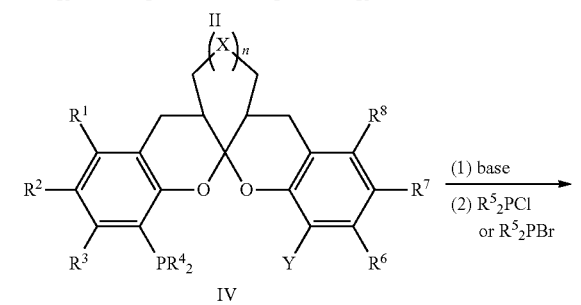

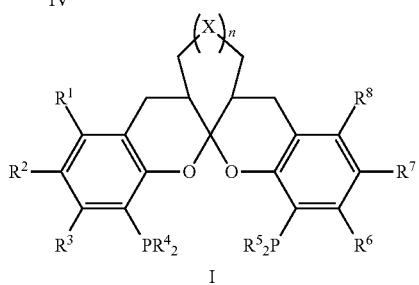

(i1) the compound of formula II reacts with a base in an organic solvent and then reacts with R$^4_2$PCl or R$^4_2$PBr to form a compound of formula IV;

(ii1) the compound of formula IV reacts with a base and then reacts with R$^5_2$PCl or R$^5_2$PBr to form the ligand, wherein Y is Cl, Br or I;
R$^1$, R$^2$, R$^3$, R$^4$, R$^5$, R$^6$, R$^7$, R$^8$, X and n are defined as above, and R$^4$≠R$^5$;
or comprises the steps:

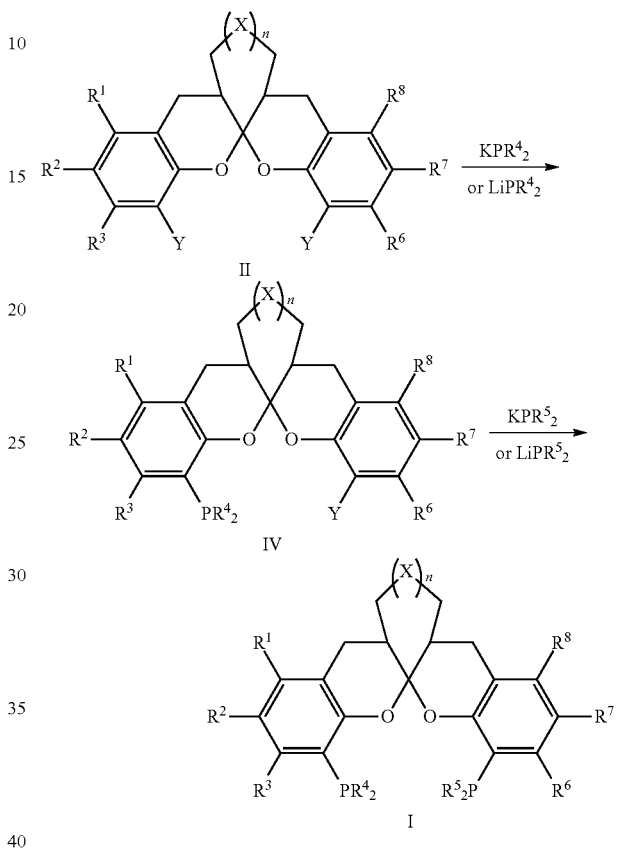

(i2) the compound of formula II reacts with KPR$^4_2$ or LiPR$^4_2$ in an organic solvent to form a compound of formula IV;

(ii2) the compound of formula IV reacts with KPR$^5_2$ or LiPR$^5_2$ to form the ligand,
wherein Y is F; R$^1$, R$^2$, R$^3$, R$^4$, R$^5$, R$^6$, R$^7$, R$^8$, R$^9$, R$^{10}$, X and n are defined as above, and R$^4$≠R$^5$.

In another preferred embodiment, in step (i1), the mole ratio of the base to the compound of formula II is 1:1-1.2:1; and the mole ratio of R$^4_2$PCl or R$^4_2$PBr to the compound of formula II is 1:1-1.2:1; and/or
in step (ii1), the mole ratio of the base to the compound of formula IV is 1:1-1.2:1; and the mole ratio of R$^5_2$PCl or R$^5_2$PBr to the compound of formula IV is 1:1-1.2:1.

In another preferred embodiment, reaction temperature is −78° C.-100° C., preferably, −78° C.-60° C., more preferably, −78° C.-25° C., particularly preferably, −78° C.-0° C.; and the reaction time is 0.5 hr-48 hrs, preferably, 1 hr-24 hrs.

In another preferred embodiment, the mole ratio of KPR$^4_2$ or LiPR$^4_2$ to the compound of formula II in step (i2) is 1:1-1.2:1; and/or the mole ratio of KPR$^5_2$ or LiPR$^5_2$ to the compound of formula
IV in step (ii2) is 1:1-1.2:1.

In another preferred embodiment, KPR$^4_2$, LiPR$^4_2$, KPR$^5_2$ or LiPR$^5_2$ can be prepared by corresponding phosphine compound and base on site.

In another preferred embodiment, the reaction temperature of step (i2) and (ii2) is −78° C.-150° C., preferably, 20° C.-80° C., and the reaction time is 0.5 hr-48 hrs, preferably 6-10 hrs.

In another preferred embodiment, said organic solvent is one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide, or a mixture thereof.

In another preferred embodiment, said base is selected from n-butyl lithium, tert-butyl lithium, cyclohexyl lithium, methyl lithium, isopropyl lithium, lithium bis(trimethylsilyl)amide, sodium bis(trimethylsilyl)amide, potassium bis(trimethylsilyl)amide, ethyl magnesium chloride, ethyl magnesium bromide, phenyl magnesium chloride, phenyl magnesium bromide.

In another preferred embodiment, said base is n-butyl lithium or tert-butyl lithium.

Use

The ligand according to the present invention can be used as a catalyst in asymmetric catalytic reaction. There is a ring system behind the spiroketalbackbone. The backbone can be effectively adjusted by changing ring system, thereby adjusting chiral-control ability of the ligand in different asymmetric catalytic reactions.

In one preferred embodiment, the ligand according to the present invention can form complex with a transition metal to be used as a catalyst in asymmetric allyl amination of Morita-Baylis-Hillman adduct, a compound of formula 8 to prepare a chiral α-alkylidene-β-amino carboxylic acid derivative, a compound of formula 9 with wide applications. The reaction equation is as follows:

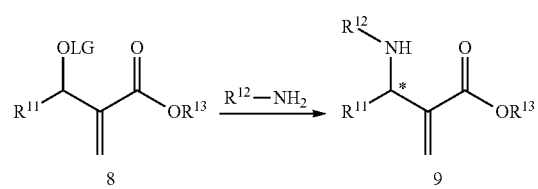

wherein $R^{11}$ and $R^{12}$ are independently selected from a phenyl, a substituted phenyl (for example, substituted by a halogen, a $C_{1-6}$ alkyl, a $C_{1-6}$ haloalkyl, or a $C_{1-6}$ alkoxyl), 2-furyl, a $C_3$-$C_{10}$ cycloalkyl or a $C_1$-$C_{10}$ alkyl;

$R^{13}$ is selected from a methyl, an ethyl, an isopropyl, an n-butyl, a tert-butyl, a benzyl, or an adamantly; and LG is selected from an acetyl (Ac), a t-butyloxycarbonyl (Boc), a methoxycarbonyl (—$CO_2Me$), a di(ethoxy)phosphinyl ($POEt_2$).

The advantages of the invention include:
(1) the present invention provides a novel aromatic spiroketal bisphosphine ligand with optical activity which can be used as a catalyst in asymmetric catalytic reaction; and
(2) the present invention provides a simple and feasible preparation method for the aromatic spiroketal bisphosphine ligand which is racemic or possesses optical activity and can be prepared by a simple method from racemic and optically pure aromatic spiroketal compounds to obtain chiral ligands without resolution.

The invention will be further illustrated with reference to the following specific examples. It should be understood that these examples are only intended to illustrate the invention, but not to limit the scope of the invention. The experimental methods in the following examples without particular conditions mentioned are performed under routine conditions or as instructed by the manufacturer.

EXAMPLE 1

The preparation method for the chiral aromatic spiroketal compound according to the present invention is illustrated by the preparation of chiral aromatic spiroketal compound 5a from 3a-Bn (the reaction route is shown below) in this example.

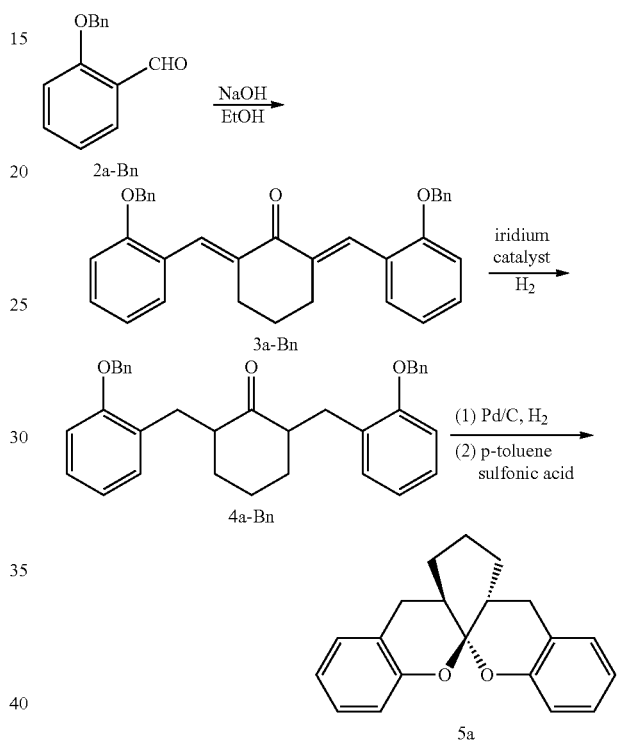

The first step: preparation of compound 3a-Bn from compound 2a-Bn

2a-Bn (4.0 g, 0.018 mol), cyclohexanone (0.93 mL, 0.009 mol), ethanol (10 mL) and 20% aqueous NaOH solution (5 mL) were added to a 250 mL one-necked flask and stirred at room temperature for 12 hrs. 100 mL of water was added and the reaction mixture was filtered to obtain yellow solids. After dried, yellow solids were recrystallized in a mixed solution of petroleum ether and ethyl acetate to obtain 3.5 g of yellow crystalline solids in 80% yield.

3a-Bn, yellow solid, $^1$H NMR (300 MHz, $CDCl_3$) δ 8.11 (s, 2H), 7.46-7.25 (s, 14H), 7.00-6.94 (m, 4H), 7.06-7.01 (m, 2H), 5.16 (s, 4H), 2.84 (t, J=4.5 Hz, 4H), 1.76-1.74 (m, 4H) ppm.

The second step: preparation of compound 4a-Bn from compound 3a-Bn

The hydrogenation product, 4a-Bn was prepared by using compound 3a-Bn as a hydrogenation substrate and different phosphine-oxazoline ligands-iridium complex as catalysts. The reaction was conducted as follows: 3a-Bn (48 mg, 0.1 mmol), iridium complex (0.001 mmol) and 2 mL of anhydrous dichloromethane were added to a hydrogenation flask.

The hydrogenation flask was placed in a glovebox and transferred to a high pressure reactor. Hydrogen displacement was performed for three times, and then the reactor was charged with 50 atm of hydrogen. The reaction was carried out at room temperature for 24 hrs. After hydrogen was discharged, the reactor was opened and the solvent was removed under reduced pressure. The ratio of cis-form to trans-form of the product was determined by crude $^1$H-NMR. The residue was separated by column chromatography. The yield of trans-4a-Bn was obtained and enantioselectivity was determined by chiral high pressure liquid chromatography.

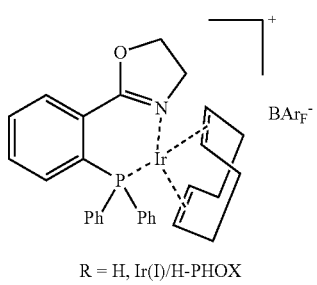

R = H, Ir(I)/H-PHOX

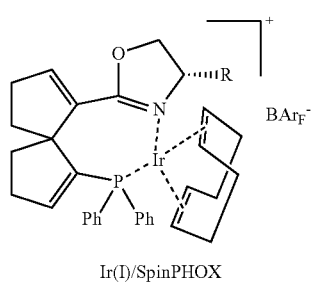

Ir(I)/SpinPHOX

R = $^t$Bu, (R,S)-7a (S,S)-7a
R = $^s$Bu, (R,S)-7b (S,S)-7b
R = Bn, (R,S)-7c (S,S)-7c
R = $^i$Pr, (R,S)-7d (S,S)-7d
R = Ph, (R,S)-7e (S,S)-7e

TABLE 1 asymmetric hydrogenation results of substrate 3a-Bn by using different phosphine-oxazoline ligands-iridium complex as catalysts

| catalyst | yield of trans-4a-Bn compound (%) | trans/cis | ee (%) (trans-4a-Bn compound) |
|---|---|---|---|
| Ir(I)/(R,S)-7a | 83 | 91/9 | >99 (−) |
| Ir(I)/(S,S)-7a | 77 | 83/17 | >99 (+) |
| Ir(I)/(R,S)-7b | 45 | 56/44 | 98 (−) |
| Ir(I)/(S,S)-7b | 81 | 84/16 | >99 (+) |
| Ir(I)/(R,S)-7c | 80 | 82/18 | >99 (−) |
| Ir(I)/(S,S)-7c | 89 | 93/7 | >99 (+) |
| Ir(I)/(R,S)-7d | 65 | 68/31 | >99 (−) |
| Ir(I)/(S,S)-7d | 87 | ND | ND (+) |
| Ir(I)/(R,S)-7e | 89 | 91/9 | >99 (−) |
| Ir(I)/(S,S)-7e | 88 | 90/10 | >99 (+) | note:
iridium complex used was prepared according to the method reported in Angew. Chem. Int. Ed. 2009, 48, 5345.

Results from Ir(I)/(S,S)-7c used as the catalyst: 4a-Bn, viscous liquid, $[\alpha]_D^{20}$=+28.6 (c 1.00, CHCl$_3$), >99% ee (determined by high performance liquid chromatography, chiral AD-H column, n-hexane/isopropyl alcohol=99:1, 1.0 mL/min, 230 nm; $t_R$ (major)=5.69 min; $t_R$ (minor)=6.82 min). $^1$H NMR (300 MHz, CDCl$_3$) δ 7.41-7.22 (m, 10H), 7.17-7.12 (m, 2H), 7.02 (d, J=Hz, 2H), 6.89-6.79 (m, 4H), 5.05 (s, 4H), 3.07 (dd, J=13.5, 5.7 Hz, 2H), 2.94-2.90 (m, 2H), 2.68 (dd, J=13.2, 9.0 Hz, 2H), 1.84-1.52 (m, 6H) ppm; $^{13}$C NMR (75 MHz, CDCl$_3$) δ 215.2, 156.4, 137.1, 130.8, 128.9, 128.3, 127.6, 127.2, 126.8, 120.4, 111.4, 69.5, 48.8, 32.1, 30.8, 20.4 ppm.

The third step: preparation of compound 5a from compound 4a-Bn

Compound 4a-Bn was used as a substrate and benzyl was removed by using Pd/C as a catalyst under hydrogen atmosphere to prepare compound 5a. The reaction was conducted as follows: 4a-Bn (80 mg, 0.16 mmol), Pd/C (10 mg) and 2 mL of methanol were added to a hydrogenation flask and then transferred to a high pressure reactor in air. Hydrogen displacement was performed for three times, and then the reactor was charged with 5 atm of hydrogen. The reaction was carried out at room temperature for 24 hrs. After hydrogen was discharged, the reactor was opened, and p-toluenesulfonic acid (10 mg) was added and then stirred at room temperature for 2 hrs. The solvent was removed under reduced pressure and the residue was separated by column chromatography to obtain trans-5a in 90% yield. The ee value of trans-5a is more than 99% and absolute configuration is (R,R,R).

EXAMPLE 2

The preparation method for the chiral aromatic spiroketal compound according to the present invention is illustrated by the preparation of chiral aromatic spiroketal compound 5a from 3a-Me (the reaction route is shown below) in this example.

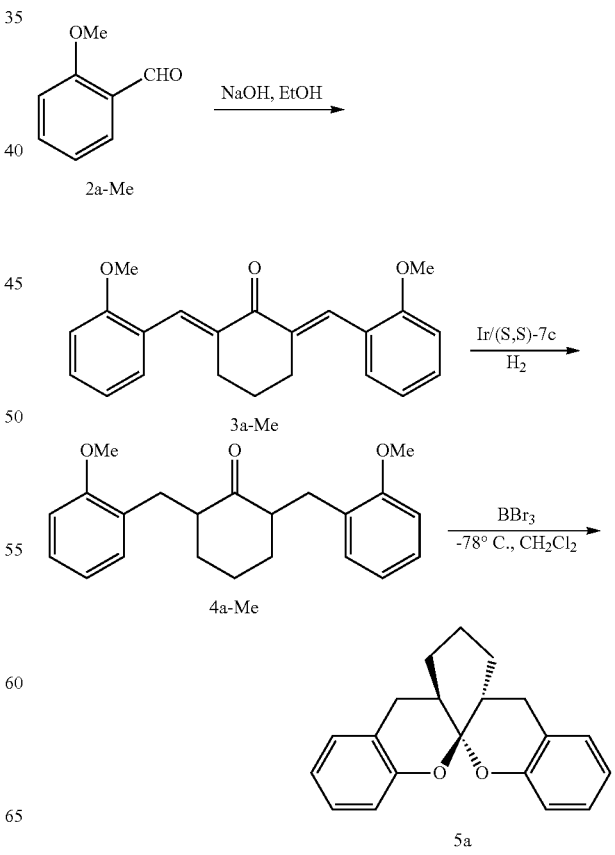

The first step: preparation of compound 3a-Me from compound 2a-Me

2a-Me (2.44 g, 0.018 mol), cyclohexanone (0.93 mL, 0.009 mol), ethanol (10 mL) and 20% aqueous NaOH solution (5 mL) were added to a 250 mL one-necked flask and stirred at room temperature for 12 hrs. 100 mL of water was added and the reaction mixture was filtered to obtain yellow solids. After dried, yellow solids were recrystallized in a mixed solution of petroleum ether and ethyl acetate to obtain 2.5 g of yellow crystalline solids in 83% yield.

3a-Me, yellow solid, $^1$H NMR (400 MHz, CDCl$_3$) δ 7.98 (s, 2H), 7.32-7.28 (m, 4H), 6.97-6.89 (m, 4H), 3.84 (s, 6H), 2.84-2.80 (m, 4H), 1.76-1.70 (m, 2H) ppm; $^{13}$C NMR (100 MHz, CDCl$_3$) δ 190.4, 158.2, 136.4, 132.3, 130.2, 129.9, 125.0, 119.8, 110.5, 55.3, 28.6, 23.4 ppm.

The third step: preparation of compound 4a-Me from compound 3a-Me

The hydrogenation product 4a-Me was prepared by using compound 3a-Me as a hydrogenation substrate and Ir(I)/(S,S)-7c as a catalyst. The reaction was conducted as follows: 3a-Me (33.4 mg, 0.1 mmol), Ir(I)/(S,S)-7c (1.6 mg, 0.001 mmol) and 2 mL of anhydrous dichloromethane were added to a hydrogenation flask. The hydrogenation flask was placed in glovebox and transferred to a high pressure reactor. Hydrogen displacement was performed for three times, and then the reactor was charged with 50 atm of hydrogen. The reaction was carried out at room temperature for 24 hrs. After hydrogen was discharged, the reactor was opened and the solvent was removed under reduced pressure. The ratio of cis-form to trans-form of the product was determined by crude $^1$H-NMR. The residue was separated by column chromatography. The yield of trans-4a-Me was 90%, the ratio of trans-form to cis-form was 94/6 and the ee value of trans-4a-Me was more than 99%.

4a-Me, viscous liquid, $[\alpha]_D^{20}$=+14.1 (c 1.00, CHCl$_3$), >99% ee (determined by high performance liquid chromatography, chiral OD-H column; n-hexane/isopropyl alcohol=90:10, 1.0 mL/min, 220 nm; $t_R$ (major)=7.97 min; $t_R$ (minor)=9.45 min). $^1$H NMR (300 MHz, CDCl$_3$) δ 7.16 (t, J=7.8 Hz, 2H), 7.05 (d, J=7.5 Hz, 2H), 6.86-6.80 (m, 4H), 3.77 (s, 6H), 3.11 (dd, J=13.5, 6.3 Hz, 2H), 2.90-2.85 (m, 2H), 2.62 (dd, J=13.5, 8.4 Hz, 2H), 1.86-1.69 (m, 4H), 1.59-1.53 (m, 2H) ppm; $^{13}$C NMR (75 MHz, CDCl$_3$) δ 215.3, 157.3, 130.6, 128.0, 127.2, 120.1, 110.1, 54.9, 48.9, 32.5, 30.9, 20.4 ppm.

The third step: preparation of compound 5a from compound 4a-Me

The substrate 4a-Me (110 mg, 0.32 mmol), anhydrous N,N-dimethylformamide (2 mL) and sodium thioethylate (60 mg, 0.704 mmol) were added to a 10 mL of water-free and oxygen-free Schlenk tube and heated to reflux for 5 hrs. The reaction mixture was cooled to room temperature and p-toluenesulfonic acid (20 mg) was added and stirred at room temperature for 1.5 hrs. 5 mL of saturated sodium bicarbonate was added to quench the reaction and the reaction mixture was extracted with dichloromethane for three times, dried on anhydrous sodium sulfate, filtered and concentrated. The residue was separated by column chromatography to obtain 5a in 78% yield, the ee value of which was more than 99%.

EXAMPLE 3

The preparation method for the chiral aromatic spiroketal compound according to the present invention is illustrated by the preparation of chiral aromatic spiroketal compound 5p from 3p-Bn (the reaction route is shown below) in this example.

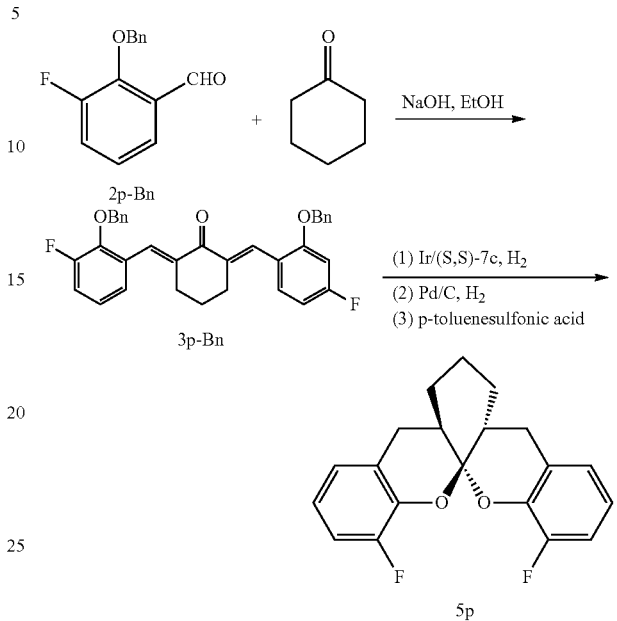

The first step: preparation of compound 3p-Bn from compound 2p-Bn

2p-Bn (4.14 g, 0.018 mol), cyclohexanone (0.93 mL, 0.009 mol), ethanol (10 mL) and 20% aqueous NaOH solution (5 mL) were added to a 250 mL one-necked flask and stirred at room temperature for 12 hrs. 100 mL of water was added and the reaction mixture was filtered to obtain yellow solids. After dried, yellow solids were recrystallized in a mixed solution of petroleum ether and ethyl acetate to obtain 3.8 g of yellow crystalline solids in 80.8% yield.

3p-Bn, yellow solid, $^1$H NMR (400 MHz, CDCl$_3$) δ 7.87, 7.42-7.39 (m, 4H), 7.33-7.27 (m, 6H), 7.10-6.98 (m, 6H), 5.08 (s, 4H), 2.68-2.64 (m, 4H), 1.64-1.58 (m, 2H) ppm; $^{19}$F NMR (368 MHz, CDCl$_3$) δ −129.1 ppm.

The second step: preparation of compound 5p from compound 3p-Bn

The compound 4p was prepared by using compound 3p-Bn as a hydrogenation substrate and Ir(I)/(S,S)-7c as a catalyst. The reaction was conducted as follows: 3p-Bn (52 mg, 0.1 mmol), Ir(I)/(S,S)-7c (1.6 mg, 0.001 mmol) and 2 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and the solvent was removed under reduced pressure. After the catalyst was removed by a short silica column, the obtained viscous liquid was directly added to a hydrogenation flask. 10 mg Pd/C and 4 mL of methanol were added and the hydrogenation flask was placed in a reactor. The reactor was charged with 5 atm of hydrogen and the reaction was carried out for 10 hrs. After hydrogen was discharged, p-toluenesulfonic acid (10 mg) was directly added to the hydrogenation flask and stirred at room temperature for 2 hrs. After filtered and concentrated, the residue was separated by column chromatography. The yield of trans-5p was 90%, the ratio of trans-form to cis-form was 93/7, the ee value of trans-5p was more than 99% and absolute configuration was (R,R,R).

5p, white solid, mp 160-161° C., $[\alpha]_D^{20}=-33.1$ (c 1.00, CHCl$_3$), >99% ee (determined by high performance liquid chromatography, chiral AD-H column, n-hexane/isopropyl alcohol=90:10, 1.0 mL/min, 230 nm; $t_R$ (minor)=4.99 min; $t_R$ (major)=7.57 min). $^1$H NMR (300 MHz, CDCl$_3$) δ 7.21-7.19 (m, 4H), 6.71 (d, J=9.0 Hz, 2H), 2.90 (dd, J=16.5, 6.0 Hz, 2H), 2.65 (dd, J=17.1, 7.5 Hz, 2H), 2.29-2.26 (m, 2H), 1.83-1.77 (m, 2H), 1.61-1.47 (m, 4H) ppm; $^{19}$F NMR (282 MHz, CDCl$_3$) δ 121.8 ppm.

EXAMPLE 4

The one-pot preparation method for the chiral aromatic spiroketal compound according to the present invention is illustrated by the preparation of chiral aromatic spiroketal compound 5a from 3a-Bn (the reaction route is shown below) in this example.

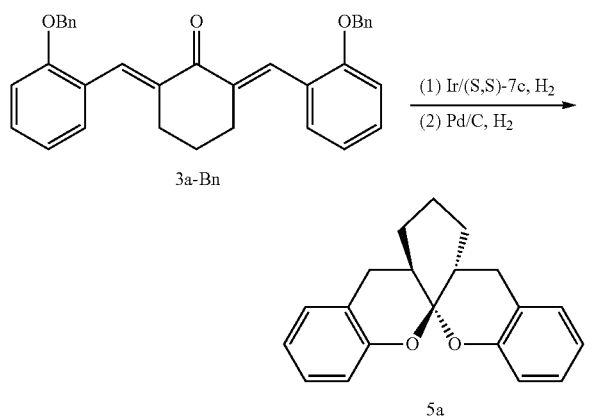

Compound 3a-Bn was used as a hydrogenation substrate and Ir(I)/(S,S)-7c was used as a catalyst. The reaction was conducted as follows: 3a-Bn (48 mg, 0.1 mmol), Ir(1)/(S,S)-7c (1.6 mg, 0.001 mmol) and 2 mL, of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and Pd/C (10 mg) was directly added to the hydrogenation flask which was then transferred to a high pressure reactor in air. Hydrogen displacement was performed for three times, and then the reactor was charged with 5 atm of hydrogen. The reaction was carried out at mom temperature for 24 hrs. After hydrogen was discharged, the reactor was opened and the solvent was removed under reduced pressure. The ratio of cis-form to trans-form of the product was determined by crude $^1$H-NMR. The residue was separated by column chromatography. The yield of trans-5a was 88%, the ratio of trans-form to cis-form was 92/8, the ee value of trans-5a was more than 99% and absolute configuration was (R,R,R).

EXAMPLE 5

The one-pot preparation method for the chiral aromatic spiroketal compound according to the present invention is illustrated by the preparation of chiral aromatic spiroketal compound 5p from 3p-Bn (the reaction route is shown below) in this example.

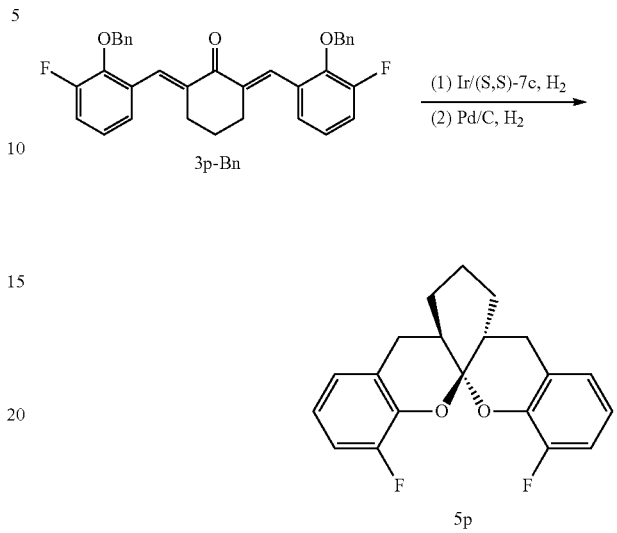

Compound 3p-Bn was used as a hydrogenation substrate and Ir(I)/(S,S)-7c was used as a catalyst. The reaction was conducted as follows: 3p-Bn (52 mg, 0.1 mmol), Ir(I)/(S,S)-7c (1.6 mg, 0.001 mmol) and 2 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 10 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain trans-5p in 91% yield. The ratio of trans-form to cis-form was 92/8, the ee value of trans-5p was more than 99% and absolute configuration was (R,R,R).

EXAMPLE 6

Compounds of Formulae 3b-Bn-3i-Bn were prepared according to the method of example 1 by using benzyl-protecting 3-fluoro-5-methylsalicylaldehyde, 3-fluoro-5-chlorosalicylaldehyde, 3-fluoro-4-methylsalicylaldehyde, 3-benzyloxysalicylaldehyde, 5-methylsalicylaldehyde, 4-methoxysalicylaldehyde to replace benzyl-protecting salicylaldehyde, respectively.

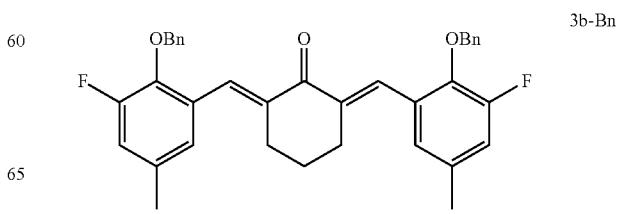

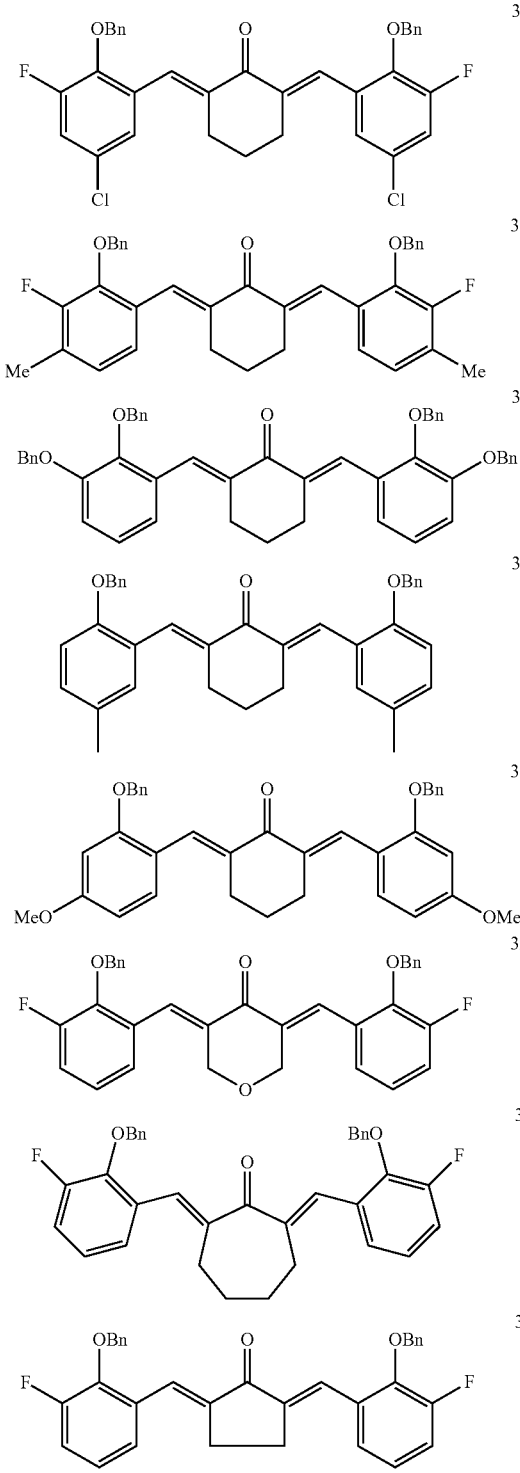

3b-Bn, $^1$H NMR (400 MHz, CDCl$_3$) δ 8.06 (s, 2H), 7.31-7.26 (m, 8H), 7.11-7.09 (m, 2H), 7.05-6.81 (m, 4H), 5.15 (s, 4H), 2.82 (t, J=4.8 Hz, 4H), 2.32 (s, 6H), 1.75-1.71 (m, 2H) ppm. $^{19}$F NMR (282 MHz, CDCl$_3$) δ 123.6 ppm.

3c-Bn, $^1$H NMR (400 MHz, CDCl$_3$) δ 7.89 (s, 2H), 7.38-7.21 (m, 10H), 7.07-6.92 (m, 4H), 5.19 (s, 4H), 2.88-2.69 (m, 4H), 1.69-1.58 (m, 2H) ppm. $^{19}$F NMR (282 MHz, CDCl$_3$) δ 125.6 ppm.

3d-Bn, $^1$H NMR (400 MHz, CDCl$_3$) δ 8.01 (s, 2H), 7.38-7.27 (m, 8H), 7.09-7.06 (m, 2H), 7.01-6.71 (m, 4H), 5.04 (s, 4H), 2.81-2.78 (m, 4H), 2.33 (s, 6H), 1.77-1.72 (m, 2H) ppm. $^{19}$F NMR (282 MHz, CDCl$_3$) δ 127.9 ppm.

3e-Bn, $^1$H NMR (400 MHz, CDCl$_3$) δ 7.92 (s, 2H), 7.48-7.21 (m, 20H), 7.05-6.90 (m, 6H), 5.14 (s, 4H), 5.01 (s, 4H), 2.71-2.64 (m, 4H), 1.63-1.57 (m, 2H) ppm.

3f-Bn, $^1$H NMR (400 MHz, CDCl$_3$) δ 8.03 (s, 2H), 7.42-7.28 (m, 10H), 7.13 (s, 2H), 7.06-7.04 (m, 2H), 6.83 (d, J=8.4 Hz, 2H), 5.11 (s, 4H), 2.83 (t, J=5.2 Hz, 4H), 2.29 (s, 6H), 1.76-1.70 (m, 2H) ppm.

3 g-Bn, $^1$H NMR (400 MHz, CDCl$_3$) δ 8.07 (s, 2H), 7.47-7.27 (m, 12H), 6.53-6.49 (m, 4H), 5.13 (s, 4H), 3.79 (s, 6H), 2.87-2.81 (m, 4H), 1.80-1.71 (n, 2H) ppm.

3 h-Bn, $^1$H NMR (400 MHz, CDCl$_3$) δ 7.99 (s, 2H), 7.63-7.52 (m, 10H), 7.45-7.31 (m, 2H), 6.90-6.82 (m, 4H), 5.15 (s, 4H), 4.81 (s, 4H) ppm; $^{19}$F NMR (282 MHz, CDCl$_3$) δ 126.2 ppm.

3i-Bn, $^1$H NMR (400 MHz, CDCl$_3$) δ 7.69 (s, 2H), 7.45-7.32 (m, 8H), 7.24-7.17 (m, 4H), 6.90-6.83 (m, 4H), 5.19 (s, 4H), 2.78-2.68 (m, 4H), 1.97-1.82 (m, 4H) ppm; $^{19}$F NMR (282 MHz, CDCl$_3$) δ 125.3 ppm.

3j-Bn, $^1$H NMR (400 MHz, CDCl$_3$) δ 7.79 (s, 2H), 7.54-7.38 (m, 10H), 6.89-6.78 (m, 2H), 6.65-6.60 (m, 4H), 5.20 (s, 4H), 2.69-2.78 (m, 4H) ppm; $^{19}$F NMR (282 MHz, CDCl$_3$) δ 124.2 ppm. The preparation method for the following compounds were described in detail by the following examples.

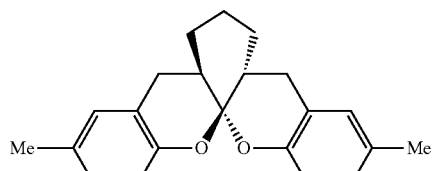

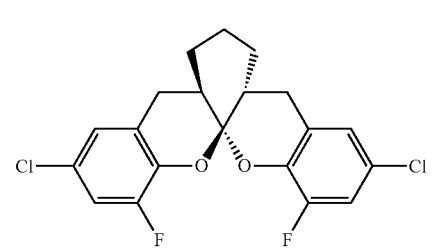

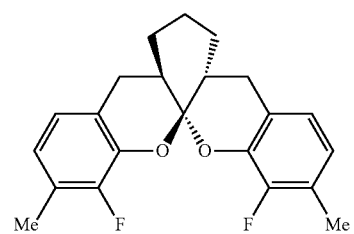

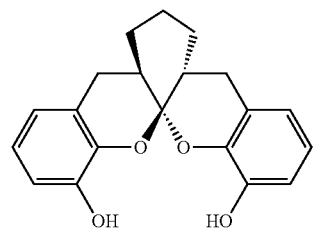

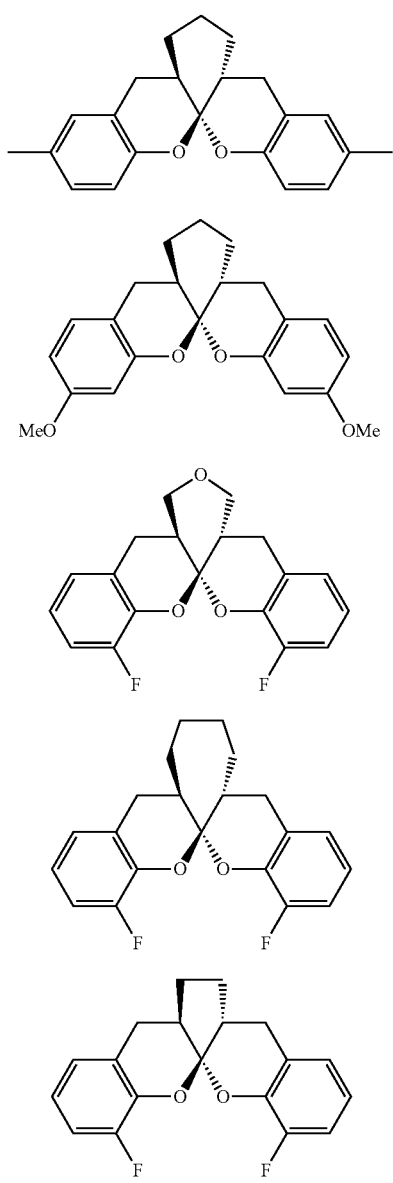

the reaction mixture was filtered and concentrated and the residue was separated by column chromatography to obtain (R,R,R)-5b in 87% yield, the ee value of which was more than 99%.

(R,R,R)-5b, $[\alpha]_D^{20}=-97.8$ (c 1.0, CHCl$_3$), >99% ee (determined by high performance liquid chromatography, chiral AD-H column; n-hexane/isobutanol=99:1, 1.0 mL/min, 230 nm; $t_R$ (major)=4.87 min; $t_R$ (minor)=6.52 min). $^1$H NMR (400 MHz, CDCl$_3$) δ 7.15 (s, 2H), 6.81 (s, 2H), 2.95 (dd, J=16.2, 6.0 Hz, 2H), 2.68 (dd, J=16.6, 7.2 Hz, 2H), 2.38-2.32 (m, 2H), 2.25 (s, 6H), 1.85-1.78 (m, 2H), 1.58-1.47 (m, 4H) ppm; $^{19}$F NMR (282 MHz, CDCl$_3$) δ 123.5 ppm.

EXAMPLE 8

Compound 3c-Bn prepared in example 6 was used as a hydrogenation substrate and compound Ir(I)/(S,S)-7e was used as a catalyst to prepare chiral aromatic spiroketal compound (R,R,R)-5c. The reaction was conducted as follows: 3c-Bn (295 mg, 0.5 mmol), catalyst Ir(I)/(S,S)-7e (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain (R,R,R)-5c in 89% yield, the ee value of which was more than 99%.

(R,R,R)-5c, $[\alpha]_D^{20}=-77.2$ (c 1.20, CHCl$_3$), >99% ee (determined by high performance liquid chromatography, chiral AD-H column; n-hexane/isobutanol=99:1, 1.0 mL/min, 230 nm; $t_R$ (major)=6.68 min; $t_R$ (minor)=6.98 min). $^1$H NMR (400 MHz, CDCl$_3$) δ 7.32 (d, J=2.6 Hz, 2H), 7.06 (d, J=2.6 Hz, 2H), 3.03 (dd, J=16.4 Hz, 6.2 Hz, 2H), 2.68 (dd, J=16.6 Hz, 7.8 Hz, 2H), 2.35-2.33 (m, 2H), 1.86-1.81 (m, 2H), 1.64-1.48 (m, 4H) ppm; $^{19}$F NMR (282 MHz, CDCl$_3$) δ 125.7 ppm.

EXAMPLE 9

Compound 3d-Bn prepared in example 6 was used as a hydrogenation substrate and compound Ir(I)/(S,S)-7e was used as a catalyst to prepare chiral aromatic spiroketal compound (R,R,R)-5d. The reaction was conducted as follows: 3d-Bn (275 mg, 0.5 mmol), catalyst Ir(I)/(S,S)-7e (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the

EXAMPLE 7

Compound 3b-Bn prepared in example 6 was used as a hydrogenation substrate and compound Ir(I)/(S,S)-7c was used as a catalyst to prepare chiral aromatic spiroketal compound (R,R,R)-5b. The reaction was conducted as follows: 3b-Bn (275 mg, 0.5 mmol), catalyst Ir(I)/(S,S)-7c (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, residue was separated by column chromatography to obtain (R,R,R)-5d in 92% yield, the ee value of which was more than 99%.

(R,R,R)-5d, $[\alpha]_D^{20}$=−81.2 (c 1.10, CHCl$_3$), >99% ee (determined by high performance liquid chromatography, chiral AD-H column; n-hexane/isobutanol=99:1, 1.0 mL/min, 230 nm; $t_R$ (major)=5.65 min; $t_R$ (minor)=6.25 min). $^1$H NMR (400 MHz, CDCl$_3$) δ 7.36 (d, J=2.6 Hz, 2H), 7.13 (d, J=2.4 Hz, 2H), 3.12 (dd, J=16.8 Hz, 6.6 Hz, 2H), 2.62 (dd, J=16.8 Hz, 7.9 Hz, 2H), 2.38-2.31 (m, 2H), 1.89-1.81 (m, 2H), 1.68-1.49 (m, 4H) ppm; $^{19}$F NMR (282 MHz, CDCl$_3$) δ 129.1 ppm.

EXAMPLE 10

Compound 3e-Bn prepared in example 6 was used as a hydrogenation substrate and compound Ir(I)/(S,S)-7e was used as a catalyst to prepare chiral aromatic spiroketal compound (R,R,R)-5e. The reaction was conducted as follows: 3e-Bn (349.4 mg, 0.5 mmol), catalyst Ir(1)/(S,S)-7e (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain (R,R,R)-5e in 86% yield, the ee value of which was more than 99%.

(R,R,R)-5e, $[\alpha]_D^{20}$=−99.2 (c 1.00, CHCl$_3$), >99% ee (determined by high performance liquid chromatography, chiral AD-H column; n-hexane/isobutanol=90:10, 1.0 mL/min, 230 nm; $t_R$ (major)=6.46 min; $t_R$ (minor)=6.98 min). 1H NMR (400 MHz, CDCl3) δ 6.86-6.75 (m, 4H), 6.67-6.63 (m, 2H), 5.42 (s, 2H), 2.99-2.89 (m, 2H), 2.79-2.68 (In, 2H), 2.44-2.34 (m, 2H), 1.90-1.78 (m, 2H), 1.68-1.52 (m, 4H) ppm.

EXAMPLE 11

Compound 3f-Bn prepared in example 6 was used as a hydrogenation substrate and compound Ir(I)/(S,S)-7b was used as a catalyst to prepare chiral aromatic spiroketal compound (R,R,R)-5f. The reaction was conducted as follows: 3f-Bn (257 mg, 0.5 mmol), catalyst Ir(1)/(S,S)-7b (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain (R,R,R)-5f in 77% yield, the ee value of which was more than 99%.

(R,R,R)-5f, $[\alpha]_D^{20}$=−37.9 (c 1.00, CHCl$_3$), >99% ee (determined by high performance liquid chromatography, chiral AD-H column, n-Hex/i-PrOH=90:10, 1.0 mL/min, 230 nm; $t_R$ (minor)=4.43 min; $t_R$ (major)=10.20 min). $^1$H NMR (400 MHz, CDCl$_3$) δ 6.91-6.88 (m, 4H), 6.74 (d, J=8.4 Hz, 2H), 2.90 (dd, J=16.4 Hz, 6.4 Hz, 2H), 2.63 (dd, J=16.8 Hz, 7.2 Hz, 2H), 2.31-2.26 (m, 8H), 1.82-1.77 (m, 2H), 1.60-1.49 (m, 4H) ppm.

EXAMPLE 12

Compound 3 g-Bn prepared in example 6 was used as a hydrogenation substrate and compound Ir(I)/(S,S)-7c was used as a catalyst to prepare chiral aromatic spiroketal compound (R,R,R)-5 g. The reaction was conducted as follows: 3 g-Bn (273 mg, 0.5 mmol), catalyst Ir(I)/(S,S)-7c (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain (R,R,R)-5 g in 79% yield, the ee value of which was more than 99%.

(R,R,R)-5 g, $[\alpha]_D^{20}$=−71.3 (c 1.05, CHCl$_3$), >99% ee (determined by high performance liquid chromatography, chiral AD-H column; n-hexane/isobutanol=95:5, 1.0 mL/min, 230 nm; $t_R$ (major)=5.78 min; $t_R$ (minor)=6.26 min). $^1$H NMR (400 MHz, CDCl$_3$) δ 7.35-7.20 (m, 2H), 7.05-6.99 (in, 2H), 6.58-6.46 (m, 2H), 3.78 (s, 6H), 2.99-2.87 (m, 2H), 2.73-2.60 (m, 2H), 2.38-2.30 (m, 2H), 1.91-1.78 (m, 2H), 1.70-1.51 (m, 4H) ppm.

EXAMPLE 13

Compound 3 h-Bn prepared in example 6 was used as a hydrogenation substrate and compound Ir(I)/(S,S)-7b was used as a catalyst to prepare chiral aromatic spiroketal compound (R,R,R)-5 h. The reaction was conducted as follows: 3 h-Bn (262 mg, 0.5 mmol), catalyst Ir(I)/(S,S)-7b (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain (R,R,R)-5 h in 70% yield, the ee value of which was more than 96%.

(S,S,R)-5 h, $[\alpha]_D^{20}$=−29.1 (c 0.95, CHCl$_3$), 96% ee (determined by high performance liquid chromatography, chiral AD-H column; n-hexane/isobutanol=98:2, 1.0 mL/min, 254 nm; $t_R$ (major)=15.32 min; $t_R$ (minor)=18.07 min). $^1$H NMR (400 MHz, CDCl$_3$) δ 7.25-7.12 (m, 2H), 6.96-6.89

(m, 4H), 3.95 (dd, J=16.6, 4.2 Hz, 2H), 3.65 (dd, J=15.2, 5.8 Hz, 2H), 3.04 (dd, J=16.9, 6.4 Hz, 2H), 2.81-2.75 (m, 2H), 2.42-2.32 (m, 2H) ppm; $^{19}$F NMR (282 MHz, CDCl$_3$) δ 111.5 ppm.

EXAMPLE 14

Compound 3i-Bn prepared in example 6 was used as a hydrogenation substrate and compound Ir(I)/(S,S)-7c was used as a catalyst to prepare chiral aromatic spiroketal compound (R,R,R)-5i. The reaction was conducted as follows: 3i-Bn (268 mg, 0.5 mmol), catalyst Ir(I)/(S,S)-7c (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain (R,R,R)-5i in 75% yield, the ee value of which was more than 99%.

(R,R,R)-5I, $[\alpha]_D^{20}$=−55.1 (c 1.00, CHCl$_3$), >99% ee (determined by high performance liquid chromatography, chiral AD-H column; n-hexane/isobutanol=95:5, 1.0 mL/min, 230 nm; $t_R$ (minor)=5.82 min; to (major)=7.23 min). $^1$H NMR (400 MHz, CDCl$_3$) δ 7.08 (d, J=12.4 Hz, 2H), 6.92 (t, J=7.4 Hz, 2H), 6.88-6.82 (m, 2H), 2.64 (dd, J=16.2, 4.2 Hz, 2H), 2.34-2.25 (m, 2H), 1.98-1.97 (m, 2H), 1.75-1.72 (m, 4H), 1.63-1.45 (m, 4H) ppm; $^{19}$F NMR (282 MHz, CDCl$_3$) δ 115.8 ppm.

EXAMPLE 15

Compound 3j-Bn prepared in example 6 was used as a hydrogenation substrate and compound Ir(I)/(S,S)-7c was used as a catalyst to prepare chiral aromatic spiroketal compound (R,R,R)-5j. The reaction was conducted as follows: 3j-Bn (268 mg, 0.5 mmol), catalyst Ir(1)/(S,S)-7c (4.8 mg, 0.003 mmol) and 10 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 20 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain (R,R,R)-5j in 60% yield, the ee value of which was more than 99%.

(R,R,R)-5j, $[\alpha]_D^{20}$=+99.2 (c 1.00, CHCl$_3$), >99% ee (determined by high performance liquid chromatography, chiral AD-H column; n-hexane/isobutanol=95:5, 1.0 mL/min, 230 nm; $t_R$ (major)=11.13 min; $t_R$ (minor)=12.90 min). $^1$H NMR (400 MHz, CDCl$_3$) δ 7.14-7.09 (m, 4H), 6.98-6.83 (m, 2H), 2.76 (dd, J=14.8, 4.2 Hz, 2H), 2.34-2.28 (m, 2H), 1.26-1.93 (m, 2H), 1.79-1.72 (m, 2H), 1.58-1.48 (m, 2H) ppm; $^{19}$F NMR (282 MHz, CDCl$_3$) δ 127.9 ppm.

EXAMPLE 16

Compound (S,S,S)-5p was prepared according to the preparation method of example 5.

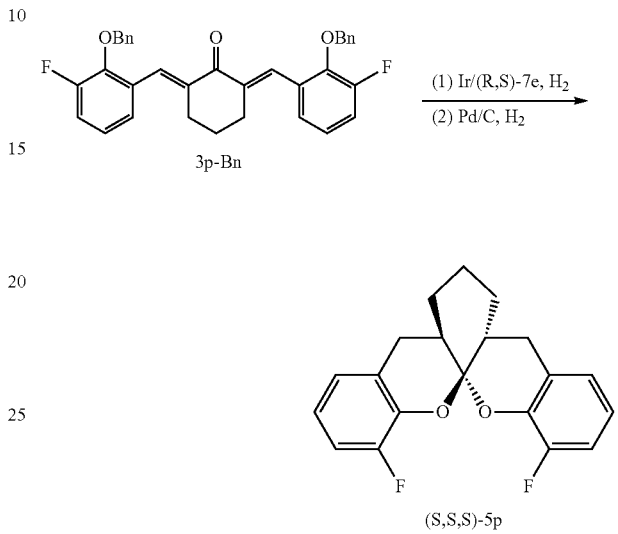

Compound 3p-Bn was used as a hydrogenation substrate and Ir(I)/(R,S)-7e was used as a catalyst. The reaction was conducted as follows: 3p-Bn (52 mg, 0.1 mmol), Ir(I)/(S, S)-7c (7.4 mg, 0.005 mmol) and 2 mL of anhydrous dichloromethane were added to a hydrogenation flask. The hydrogenation flask was placed in a glovebox and transferred to a high pressure reactor. Hydrogen displacement was performed for three times, the reactor was charged with 50 atm of hydrogen. The reaction was carried out at room temperature for 6 hrs. After hydrogen was discharged, the reactor was opened and 10 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography. The yield of the obtained trans-5P was 91% yield, the mole raio of trans-form and cis-form was 92/8, and the ee value of trans-5P was more than 99%. The NMR data was the same as that of compound 5P prepared in example 3. The absolute configuration was (S,S,S).

EXAMPLE 17

Racemic compound 5p was prepared according to the preparation method of example 5.

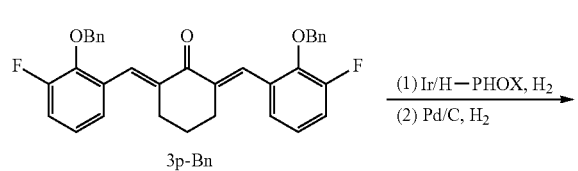

-continued

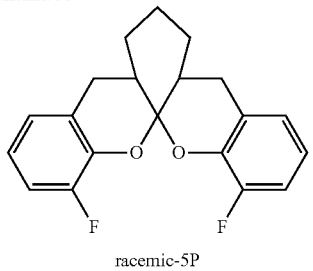

racemic-5P

Compound 3p-Bn was used as a hydrogenation substrate and Ir(1)/H-PHOX was used as a catalyst. The reaction was conducted as follows: 3p-Bn (52 mg, 0.1 mmol), Ir(I)/H-PHOX (1.6 mg, 0.001 mmol) and 2 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 10 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain racemic trans-5p in 45% yield.

EXAMPLE 18

Racemic compound 5p was prepared according to the preparation method of example 5.

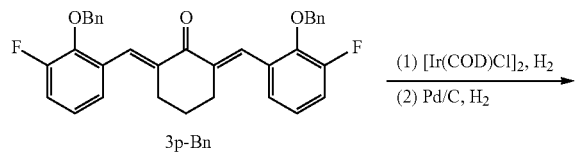

Compound 3p-Bn was used as a hydrogenation substrate and [Ir(COD)Cl]$_2$ was used as a catalyst. The reaction was conducted as follows: 3p-Bn (52 mg, 0.1 mmol), [Ir(COD)Cl]$_2$ (3.3 mg, 0.005 mmol) and 2 mL of anhydrous dichloromethane were added to a hydrogenation flask. The hydrogenation flask was placed in a glovebox and transferred to a high pressure reactor. Hydrogen displacement was performed for three times, and then the reactor was charged with 50 atm of hydrogen. The reaction was carried out at room temperature for 6 hrs. After hydrogen was discharged, the reactor was opened and 10 mg of Pd/C was directly added to the hydrogenation flask which was then placed in a reactor. The reactor was charged with 5 atm of hydrogen and the reaction was carried out for 10 hrs. After hydrogen was discharged, the reaction mixture was filtered and concentrated and the residue was separated by column chromatography to obtain racemic trans-5p in 40% yield.

EXAMPLE 19

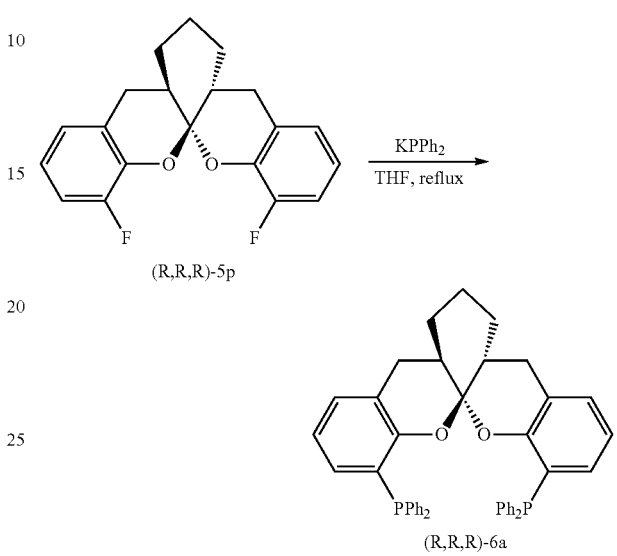

(R,R,R)-5p (500 mg, 1.52 mmol), anhydrous tetrahydrofuran (4 mL) and potassium diphenyl phosphine (KPPh$_2$, 9.12 mL, 0.5 mol/L in THF, 4.56 mmol) were added to a 50 mL of water-free and oxygen-free Schlenk tube and heated to reflux for 5 hr. After cooled, 10 mL of distilled water was added to quench the reaction. The reaction mixture was extracted with dichloromethane (3×10 mL) and the organic phase was dried on anhydrous sodium sulfate. After filtered and concentrated, the residue was purified by column chromatography to obtain target product (R,R,R)-6a in 80% yield.

(R,R,R)-6a, white solid. Mp 101-103° C., $[\alpha]_D^{20}$=+113.4 (c 1.00, CHCl$_3$). $^1$H NMR (400 MHz, CDCl$_3$) δ 7.30-7.26 (m, 20H), 6.89 (d, J=7.2 Hz, 2H), 6.74 (t, J=7.2 Hz, 2H), 6.53-6.50 (m, 2H), 2.34-2.30 (m, 4H), 1.95-1.92 (m, 2H), 1.30-1.29 (m, 2H), 1.17-1.15 (m, 4H) ppm; $^{13}$C NMR (100 MHz, CDCl$_3$) δ 153.1 (d, J$_{(P,C)}$=14.2 Hz), 137.1 (d, J$_{(P,C)}$=11.8 Hz), 136.7 (d, J$_{(P,C)}$=10.9 Hz), 134.2 (d, J$_{(P,C)}$=21.9 Hz), 133.9 (d, J$_{(P,C)}$=20.2 Hz), 130.9 (d, J$_{(P,C)}$=3.2 Hz), 129.9 (s), 128.5 (s), 128.2-128.1 (m), 124.9 (d, J$_{(P,C)}$=14.1 Hz), 120.4-120.3 (m), 101.3, 33.5, 27.6, 26.7, 19.4 ppm; $^{31}$P (162 MHz, CDCl$_3$) δ −15.8 (s) ppm.

EXAMPLE 20

(R,R,R)-5p (500 mg, 1.52 mmol), anhydrous tetrahydrofuran (4 mL) and lithium diphenyl phosphine (LiPPh$_2$, 9.12 mL, 0.5 mol/L in THF, 4.56 mmol) were added to a 50 mL of water-free and oxygen-free Schlenk tube and heated to reflux for 6 hr. After cooled, 10 mL of distilled water was added to quench the reaction. The reaction mixture was extracted with dichloromethane (3×10 mL) and the organic phase was dried on anhydrous sodium sulfate. After filtered and concentrated, the residue was purified by column chromatography to obtain pure bisphosphine ligand (R,R,R)-6a in 75% yield.

EXAMPLE 21

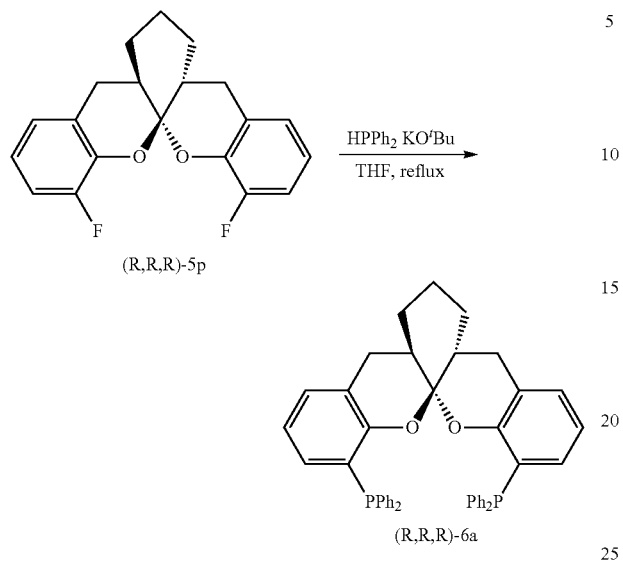

(R,R,R)-5p (500 mg, 1.52 mmol), anhydrous tetrahydrofuran (10 mL), diphenyl phosphine (849 mg, 4.56 mmol) and potassium tert-butoxide (511.6 mg, 4.56 mmol) were added to a 50 mL of water-free and oxygen-free Schlenk tube and heated to reflux for 10 hr. After cooled, 10 mL of distilled water was added to quench the reaction. The reaction mixture was extracted with dichloromethane (3×10 mL) and the organic phase was dried on anhydrous sodium sulfate. After filtered and concentrated, the residue was purified by column chromatography to obtain pure bisphosphine ligand (R,R,R)-6a in 77% yield.

EXAMPLE 22

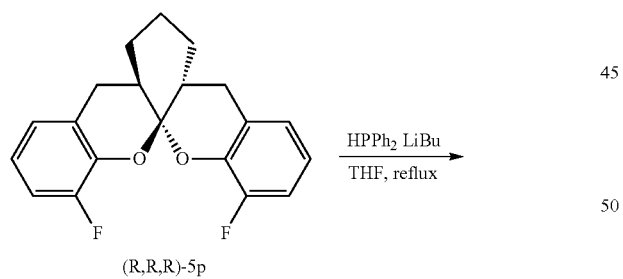

Diphenyl phosphine (849 mg, 4.56 mmol) and anhydrous tetrahydrofuran (10 mL) were added to a 50 mL of water-free and oxygen-free Schlenk tube and cooled to below −78° C. n-butyllithium (2.85 mL, 1.6 mol/L, 4.56 mmol) was slowly added dropwise, stirred at below −78° C. for 0.5 hr and then warmed to room temperature. (R,R,R)-5p (500 mg, 1.52 mmol) was added and heated to reflux for 12 hrs and then cooled to room temperature. The reaction mixture was concentrated and directly purified by column chromatography to obtain (R,R,R)-6a as white solids in 76% yield.

EXAMPLE 23

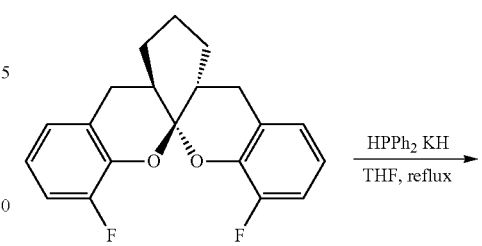

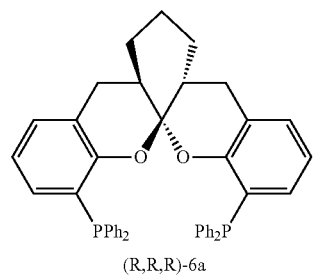

Diphenyl phosphine (849 mg, 4.56 mmol), potassium hydride (182.4 mg, 4.56 mmol) and anhydrous tetrahydrofuran (10 mL) were added to a 50 mL of water-free and oxygen-free Schlenk tube at room temperature and stirred for 0.5 hr. (R,R,R)-5p (500 mg, 1.52 mmol) was added and heated to reflux for 12 hrs and then cooled to room temperature. The reaction mixture was concentrated and directly purified by column chromatography to obtain (R,R,R)-6a as white solids in 89% yield.

EXAMPLE 24

The reaction route for preparing (S,S,S)-6a was shown as follows.

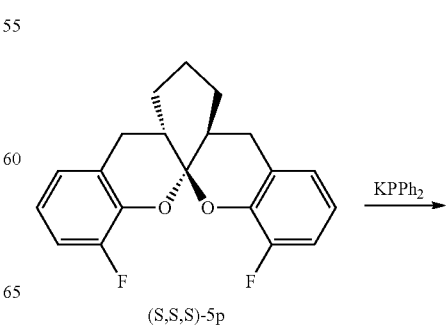

-continued

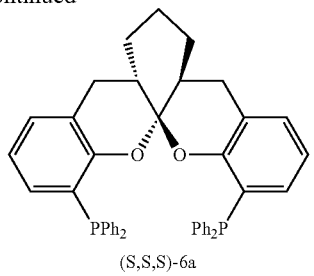

(S,S,S)-6a (S,S,S)-5 g (328 mg, 1.0 mmol), anhydrous tetrahydrofuran (4 mL) and potassium diphenyl phosphine (KPPh$_2$, 6.0 mL, 0.5 mol/L in THF, 3.0 mmol) were added to a 50 mL of water-free and oxygen-free Schlenk tube and heated to reflux for 10 hrs. After cooled, 10 mL of distilled water was added to quench the reaction and the reaction mixture was extracted with dichloromethane (3×10 mL). The organic phase was dried on anhydrous sodium sulfate, filtered and concentrated. The residue was purified by column chromatography to obtain target product, (S,S,S)-6a in 74% yield.

EXAMPLE 25

The reaction route for preparing racemic 6a was shown as follows.

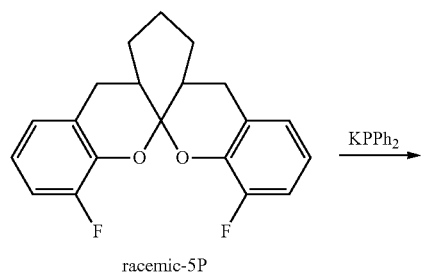

Racemic compound 5p (500 mg, 1.52 mmol), anhydrous tetrahydrofuran (4 mL) and potassium diphenyl phosphine (KPPh$_2$, 9.12 mL, 0.5 mol/L in THF, 4.56 mmol) were added to a 50 mL of water-free and oxygen-free Schlenk tube and heated to reflux for 5 hrs. After cooled, 10 mL of distilled water was added to quench the reaction and the reaction mixture was extracted with dichloromethane (3×10 mL). The organic phase was dried on anhydrous sodium sulfate, filtered and concentrated. The residue was purified by column chromatography to obtain target product, racemic 6a in 80% yield.

EXAMPLE 26

The preparation method in this example was the same as that of example 23 except that diphenyl phosphine was replaced by di(o-tolyl)phosphine to prepare chiral aromatic spiroketal bisphosphine ligand (R,R,R)-6b.

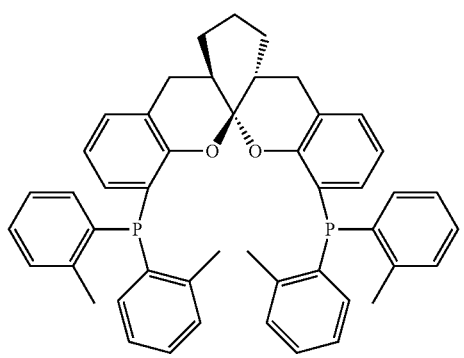

(R,R,R)-6b, white solid, 40% yield. Mp 125-127° C., [α]$_D^{20}$=+143.5 (c 1.00, CHCl$_3$). $^1$H NMR (400 MHz, CDCl$_3$) δ=7.24-7.12 (m, 8H), 7.05 (t, J=7.2 Hz, 4H), 6.88-6.85 (m, 4H), 6.79-6.72 (m, 4H), 6.53-6.50 (m, 2H), 2.39 (s, 6H), 2.34-2.23 (m, 2H), 2.18 (s, 6H), 1.99-1.95 (m, 2H), 1.34-1.15 (m, 8H) ppm; $^{13}$C NMR (75 MHz, CDCl$_3$) δ 153.5 (d, J$_{(P,C)}$=15.2 Hz), 143.2 (d, J$_{(P,C)}$=28.3 Hz), 142.7 (d, J$_{(P,C)}$=25.9 Hz), 135.3 (d, J$_{(P,C)}$=11.4 Hz), 134.9 (d, J$_{(P,C)}$=13.8 Hz), 133.5 (d, J$_{(P,C)}$=40.1 Hz), 131.0 (d, J$_{(P,C)}$=2.9 Hz), 130.0-129.6 (in), 128.3 (d, J$_{(P,C)}$=15.8 Hz), 125.8 (d, J$_{(P,C)}$=24.0 Hz), 123.3 (d, J$_{(P,C)}$=12.7 Hz), 120.6-120.5 (m), 101.4, 33.3, 27.7, 26.6, 21.2 (d, J$_{(P,C)}$=21.1 Hz), 21.0 (d, J$_{(P,C)}$=23.7 Hz), 19.3 ppm; $^{31}$P (121 MHz, CDCl$_3$) δ −33.4 ppm.

EXAMPLE 27

The preparation method in this example was the same as that of example 23 except that diphenyl phosphine was replaced by di(3,5-dimethylphenyl)phosphine to prepare chiral aromatic spiroketal bisphosphine ligand (R,R,R)-6c.

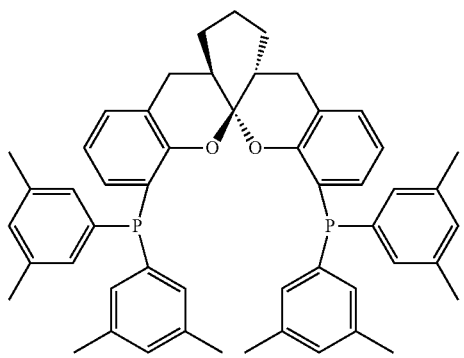

(R,R,R)-6c, white solid, 70% yield. Mp 102-103° C., [α]$_D^{20}$=+166.5 (c 1.00, CHCl$_3$). $^1$H NMR (300 MHz, CDCl$_3$) δ=6.93-6.84 (m, 14H), 6.73 (t, J=6.9 Hz, 2H), 6.47 (t, J=4.8 Hz, 2H), 2.45-2.38 (m, 4H), 2.24 (s, 12H), 2.21 (s, 12H), 2.04-1.97 (m, 2H), 1.30-1.26 (m, 2H), 1.12-1.07 (m, 4H) ppm; $^{13}$C NMR (75 MHz, CDCl$_3$) δ=153.1 (d, J$_{(P,C)}$=14.7 Hz), 137.3 (d, J$_{(P,C)}$=7.4 Hz), 137.2 (d, J$_{(P,C)}$=7.8 Hz), 136.9 (d, J$_{(P,C)}$=10.2 Hz), 136.5 (d, J$_{(P,C)}$=10.9 Hz), 132.1 (s), 131.8 (s), 131.5 (s), 130.8 (d, J$_{(P,C)}$=1.5 Hz), 130.2 (s), 129.8 (d, J$_{(P,C)}$=41.7 Hz), 125.5 (d, J$_{(P,C)}$=14.2

Hz), 120.1 (s), 120.1 (d, $J_{(P,C)}$=1.7 Hz), 101.1, 33.4, 27.3, 26.7, 21.3, 21.2, 19.5 ppm; $^{31}$P (121 MHz, CDCl$_3$) δ −15.2 ppm.

EXAMPLE 28

The preparation method in this example was the same as that of example 23 except that diphenyl phosphine was replaced by bis(3,5-di-tert-butylphenyl)phosphine to prepare chiral aromatic spiroketal bisphosphine ligand (R,R,R)-6d.

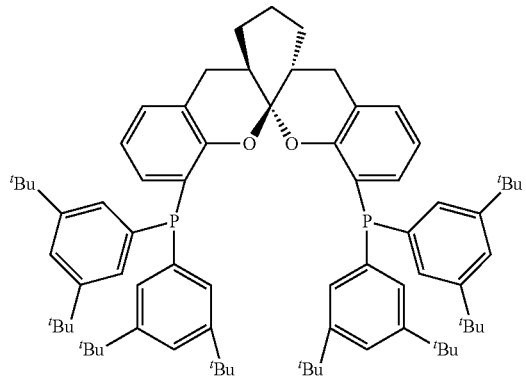

(R,R,R)-6d, white solid, 45% yield. Mp 100-101° C., $[α]_D^{20}$=+140.5 (c 1.00, CHCl$_3$). $^1$H NMR (400 MHz, CDCl$_3$) δ=6.91-6.82 (m, 14H), 6.69 (t, J=6.6 Hz, 2H), 6.37 (t, J=5.0 Hz, 2H), 2.41-2.32 (m, 4H), 2.28 (s, 36H), 2.15 (s, 36H), 2.10-1.97 (m, 2H), 1.30-1.28 (m, 2H), 1.11-1.09 (m, 4H) ppm; $^{13}$C NMR (100 MHz, CDCl$_3$) δ=155.1 (d, $J_{(P,C)}$=15.0 Hz), 139.5 (d, $J_{(P,C)}$=8.4 Hz), 137.7 (d, $J_{(P,C)}$=8.0 Hz), 136.1 (d, $J_{(P,C)}$=10.8 Hz), 135.4 (d, $J_{(P,C)}$=11.2 Hz), 133.4 (s), 131.8 (s), 130.9 (s), 130.8 (d, $J_{(P,C)}$=12.0 Hz), 130.4 (s), 129.6 (d, $J_{(P,C)}$=42.2 Hz), 126.5 (d, $J_{(P,C)}$=16.2 Hz), 120.9 (s), 120.4 (d, $J_{(P,C)}$=2.2 Hz), 99.1, 33.4, 29.8, 27.3, 26.7, 25.6, 21.3, 21.2, 19.5 ppm; $^{31}$P (121 MHz, CDCl$_3$) δ −17.8 ppm.

EXAMPLE 29

The preparation method in this example was the same as that of example 23 except that diphenyl phosphine was replaced by di(p-tolyl)phosphine to prepare chiral aromatic spiroketal bisphosphine ligand (R,R,R)-6e.

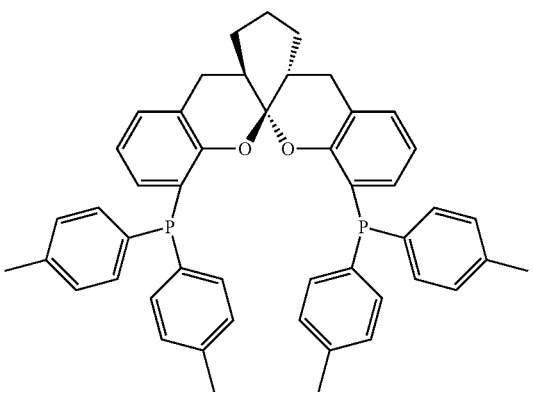

(R,R,R)-6e, white solid, 67% yield. Mp 90-92° C., $[α]_D^{20}$=+118.5 (c 1.00, CHCl$_3$). $^1$H NMR (400 MHz, CDCl$_3$) δ=7.21-7.14 (m, 8H), 7.10-7.07 (m, 8H), 6.87 (d, J=7.2 Hz, 2H), 6.73 (t, J=7.6 Hz, 2H), 6.54 (t, J=5.6 Hz, 2H), 2.36-2.25 (m, 16H), 1.96-1.92 (m, 2H), 1.32-1.26 (m, 2H), 1.19-1.15 (m, 4H) ppm; $^{13}$C NMR (100 MHz, CDCl$_3$) δ=153.1 (d, $J_{(P,C)}$=14.5 Hz), 138.2 (s), 137.8 (s), 134.3-133.8 (m), 133.4 (d, $J_{(P,C)}$=10.4 Hz), 130.8 (d, $J_{(P,C)}$=2.6 Hz), 129.7 (s), 129.0-128.9 (in), 125.5 (d, $J_{(P,C)}$=14.0 Hz), 120.3-120.2 (m), 101.2, 33.4, 27.6, 26.7, 21.3, 19.4 ppm; $^{31}$P NMR (162 MHz, CDCl$_3$) δ −17.9 ppm.

EXAMPLE 30

The preparation method in this example was the same as that of example 23 except that diphenyl phosphine was replaced by di(p-fluorophenyl)phosphine to prepare chiral aromatic spiroketal bisphosphine ligand (R,R,R)-6f.

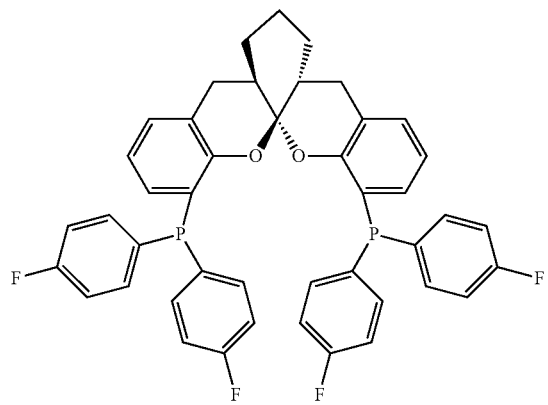

(R,R,R)-6f, white solid, 80% yield. Mp 76-77° C., $[α]_D^{20}$=+88.0 (c 1.00, CHCl$_3$). $^1$H NMR (400 MHz, CDCl$_3$) δ=7.27-7.20 (m, 8H), 6.99-6.93 (m, 10H), 6.76 (t, J=7.6 Hz, 2H), 6.49-6.46 (m, 2H), 2.50-2.39 (m, 4H), 2.01-1.94 (m, 2H), 1.33-1.32 (m, 2H), 1.20-1.11 (m, 4H) ppm; $^{31}$P NMR (162 MHz, CDCl$_3$) δ −17.8 ppm; $^{19}$F NMR (376 MHz, CDCl$_3$) δ −112.3, −112.5 ppm.

EXAMPLE 31

The preparation method in this example was the same as that of example 23 except that diphenyl phosphine was replaced by di(p-methoxyphenyl)phosphine to prepare chiral aromatic spiroketal bisphosphine ligand (R,R,R)-6 g.

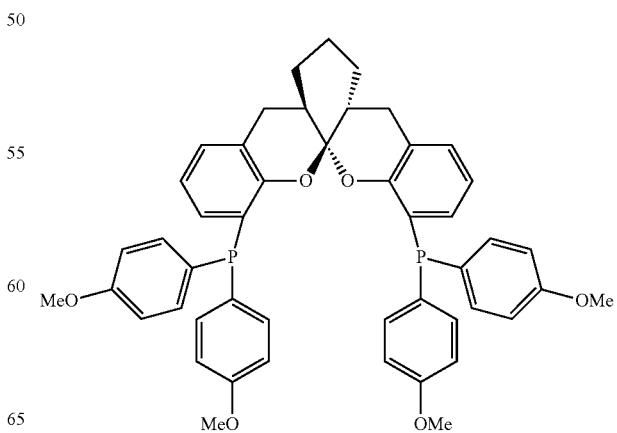

(R,R,R)-6 g, white solid, 65% yield. Mp 91-92° C., $[\alpha]_D^{20}$=+122.5 (c 1.00, CHCl$_3$). $^1$H NMR (400 MHz, CDCl$_3$) δ=7.26-7.19 (m, 8H), 6.88-6.87 (m, 2H), 6.84-6.81 (m, 8H), 6.73 (t, J=7.2 Hz, 2H), 6.51 (t, J=5.2 Hz, 2H), 3.75 (s, 6H), 3.71 (s, 6H), 2.35-2.31 (m, 4H), 1.94-1.91 (m, 2H), 1.31-1.26 (m, 3H), 1.20-1.16 (m, 3H) ppm; $^{13}$C NMR (100 MHz, CDCl$_3$) δ=159.8 (d, J$_{(P,C)}$=38.8 Hz), 152.8 (d, J$_{(P,C)}$=13.9 Hz), 135.5-135.0 (m), 130.4 (s), 129.5 (s), 128.3 (d, J$_{(P,C)}$=8.1 Hz), 127.6 (d, J$_{(P,C)}$=9.0 Hz), 125.8 (d, J$_{(P,C)}$=13.3 Hz), 120.1 (d, J$_{(P,C)}$=1.6 Hz), 113.8-113.7 (m), 101.0, 55.0, 54.9, 33.4, 27.6, 26.6, 19.3 ppm; $^{31}$P NMR (162 MHz, CDCl$_3$) δ −18.8 ppm.

EXAMPLE 32

The preparation method in this example was the same as that of example 23 except that diphenyl phosphine was replaced by dicyclohexylphosphine to prepare chiral aromatic spiroketal bisphosphine ligand (R,R,R)-6 h.

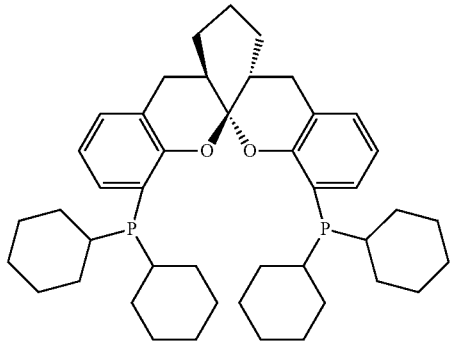

(R,R,R)-6 h, white solid, 55% yield. Mp 95-96° C., $[\alpha]_D^{20}$=+88.5 (c 1.00, CHCl$_3$). $^1$H NMR (400 MHz, CDCl$_3$) δ=7.21-7.15 (m, 4H), 6.89-6.85 (m, 2H), 2.39-2.30 (m, 8H), 1.98-1.87 (m, 6H), 1.30-1.25 (m, 18H), 1.23-1.14 (m, 20 H) ppm; $^{31}$P NMR (162 MHz, CDCl$_3$) δ −21.6 ppm.

EXAMPLE 33

The preparation method in this example was the same as that of example 23 except that diphenyl phosphine was replaced by di-tert-butylphosphine to prepare chiral aromatic spiroketal bisphosphine ligand (R,R,R)-6i.

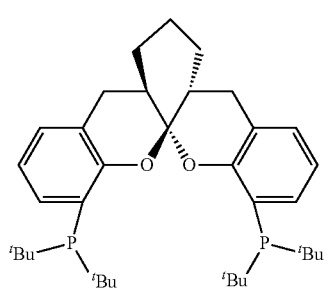

(R,R,R)-6i, white solid, 81% yield. $[\alpha]_D^{20}$=+78.1 (c 1.00, CHCl$_3$). $^1$H NMR (400 MHz, CDCl$_3$) δ=7.28-7.21 (m, 2H), 6.99-6.81 (m, 4H), 2.38-2.21 (m, 4H), 1.98-1.88 (m, 6H), 1.66-1.45 (m, 14H), 1.30-1.29 (m, 8H), 1.17-1.15 (m, 16H) ppm; $^{31}$P NMR (162 MHz, CDCl$_3$) δ −22.8 ppm.

EXAMPLE 34

The preparation method in this example was the same as that of example 19 except that (R,R,R)-5b was used as raw material to prepare chiral aromatic spiroketal bisphosphine ligand (R,R,R)-6j.

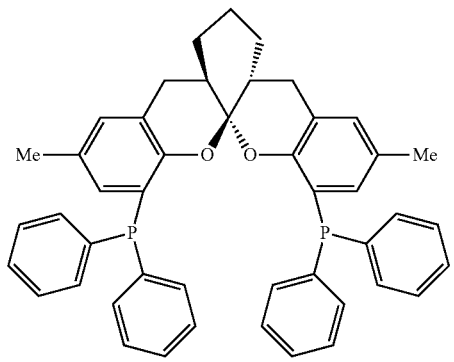

(R,R,R)-6j, white solid, 70% yield. Mp 98-100° C., $[\alpha]_D^{20}$=+109.3 (c 1.00, CHCl$_3$). $^1$H NMR (400 MHz, CDCl$_3$) δ 7.31-7.24 (m, 20H), 6.69 (s, 2H), 6.35 (d, J=5.6 Hz, 2H), 2.31-2.26 (m, 4H), 2.11 (s, 6H), 1.92-1.86 (m, 2H), 1.28-1.25 (m, 2H), 1.16-1.13 (m, 4H) ppm; $^{13}$C NMR (100 MHz, CDCl$_3$) δ 151.2, 151.1, 137.3, 137.2, 137.0, 136.9, 134.3, 134.1, 133.9, 133.7, 131.5, 131.4, 130.6, 129.2, 128.9, 128.4, 128.1, 128.0, 125.2, 124.4, 124.3, 120.1, 101.2, 33.4, 27.7, 26.7, 20.6, 19.4 ppm; $^{31}$P (162 MHz, CDCl$_3$) δ −15.3 ppm.

EXAMPLE 35

The preparation method in this example was the same as that of example 19 except that (R,R,R)-5c was used as raw material to prepare chiral aromatic spiroketal bisphosphine ligand (R,R,R)-6k.

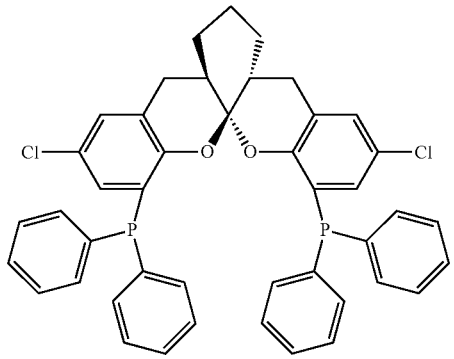

(R,R,R)-6k, white solid, 65% yield. Mp 98-100° C., $[\alpha]_D^{20}$=+101.1 (c 1.00, CHCl$_3$). $^1$H NMR (400 MHz, CDCl$_3$) δ 7.33-7.24 (m, 20H), 6.85 (s, 2H), 6.46-6.44 (m, 2H), 2.34-2.19 (m, 4H), 1.91-1.85 (m, 2H), 1.28-1.26 (m, 2H), 1.14-1.11 (m, 4H) ppm; $^{13}$C NMR (100 MHz, CDCl$_3$) δ 151.4, 151.3, 136.2, 136.1, 135.6, 135.5, 134.2, 134.05, 134.02, 133.8, 130.2, 130.1, 129.4, 128.9, 128.6, 128.46, 128.42, 128.38, 128.34, 127.7, 127.5, 125.5, 122.02, 122.01, 101.6, 33.2, 27.5, 26.6, 19.2 ppm; $^{31}$P (162 MHz, CDCl$_3$) δ −15.5 ppm.

EXAMPLE 36

The preparation method in this example was the same as that of example 19 except that (R,R,R)-5d was used as raw material to prepare chiral aromatic spiroketal bisphosphine ligand (R,R,R)-6l.

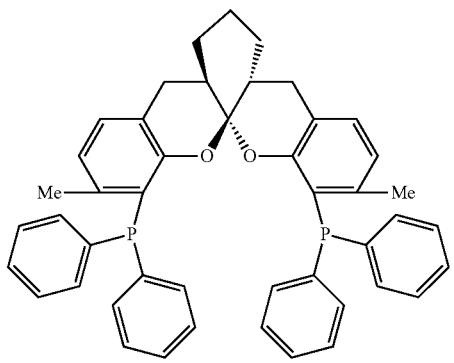

(R,R,R)-6l, white solid, 47% yield. Mp 110-112° C., $[\alpha]_D^{20}$=+100.3 (c 0.90, CHCl$_3$). $^1$H NMR (400 MHz, CDCl$_3$) δ 7.31-7.24 (m, 20H), 6.88-6.79 (m, 2H), 6.56-6.37 (m, 2H), 2.36-2.29 (m, 4H), 2.18 (s, 6H), 1.94-1.83 (m, 2H), 1.29-1.21 (m, 2H), 1.17-1.12 (m, 4H) ppm; $^{31}$P (162 MHz, CDCl$_3$) δ −14.6 ppm.

EXAMPLE 37

The preparation method in this example was the same as that of example 19 except that (R,R,R)-5 h was used as raw material to prepare chiral aromatic spiroketal bisphosphine ligand (R,R,R)-6m.

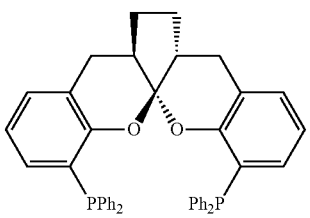

(R,R,R)-6m, white solid, 75% yield. Mp 109-111° C., $[\alpha]_D^{20}$=+83.1 (c 1.00, CHCl$_3$). $^1$H NMR (400 MHz, CDCl$_3$) δ 7.42-7.17 (m, 20H), 6.95 (d, J=7.2 Hz, 2H), 6.76 (t, J=7.6 Hz, 2H), 6.58 (t, J=7.2 Hz, 2H), 2.45 (dd, J=16.0 Hz, 6.4 Hz, 2H), 2.28 (dd, J=16.0 Hz, 6.8 Hz, 2H), 1.98-1.95 (m, 2H), 1.47-1.43 (m, 2H), 1.12-1.08 (m, 2H) ppm; $^{31}$P (162 MHz, CDCl$_3$) δ −15.5 ppm.

EXAMPLE 38

The preparation method in this example was the same as that of example 19 except that (S,S,R)-5i was used as raw material to prepare chiral aromatic spiroketal bisphosphine ligand (S,S,R)-6n.

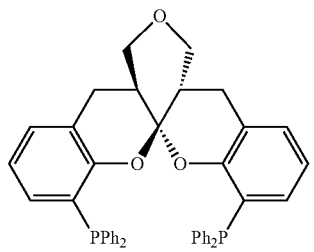

(S,S,R)-6n, white solid, 79% yield. Mp 111-112° C., $[\alpha]_D^{20}$=+75.2 (c 1.10, CHCl$_3$). $^1$H NMR (400 MHz, CDCl$_3$) δ 7.45-7.16 (m, 20H), 6.99-6.81 (m, 4H), 6.63-6.58 (m, 2H), 3.34-3.31 (m, 4H), 2.48-2.44 (m, 2H), 2.32-2.29 (m, 2H), 1.48-1.41 (m, 2H) ppm; $^{31}$P (162 MHz, CDCl$_3$) δ −17.3 ppm.

EXAMPLE 39

The preparation method in this example was the same as that of example 19 except that (R,R,R)-5j was used as raw material to prepare chiral aromatic spiroketal bisphosphine ligand (R,R,R)-6o.

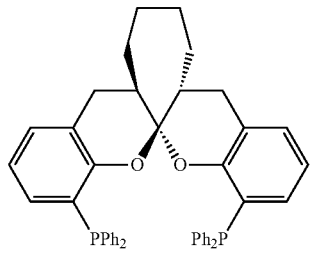

(R,R,R)-6o, white solid, 81% yield. Mp 89-92° C., $[12]_D^{20}$=+112.2 (c 1.30, CHCl$_3$). $^1$H NMR (400 MHz, CDCl$_3$) δ 7.35-7.14 (m, 20H), 6.91-6.85 (m, 2H), 6.76-6.58 (m, 4H), 2.46-2.41 (m, 2H), 2.34-2.31 (m, 2H), 1.48-1.41 (m, 6H), 1.22-1.09 (m, 4H) ppm; $^{31}$P (162 MHz, CDCl$_3$) δ −13.4 ppm.

EXAMPLE 40

Compounds of formulae 3k-Me-3m-Me were prepared according to the preparation method of example 2, respectively.

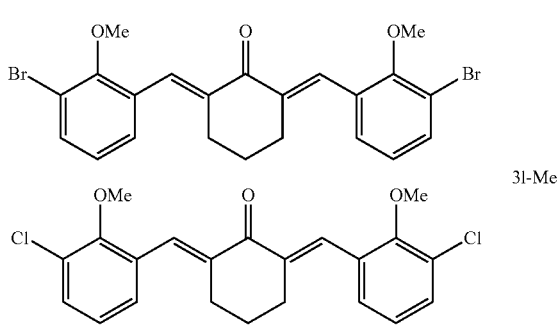

-continued

3m-Me

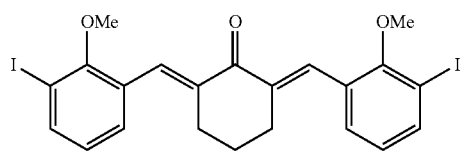

3k-Me, ESI-MS m/z: 490.9 [M+H⁺]; 3l-Me, ESI-MS m/z: 403.0 [M+H⁺];
3m-Me, ESI-MS m/z: 586.9 [M+H⁺].

EXAMPLE 41

Compounds of formulae 5k-5i were prepared according to the preparation method of example 2, respectively.

5k

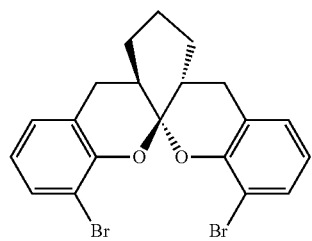

5l

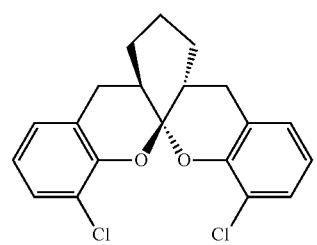

5i

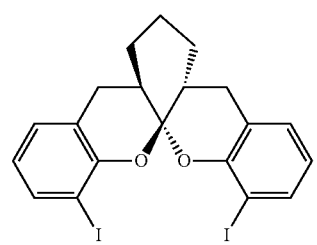

5k, EI-MS (70 eV) (m/z) 447 (M⁺); 5l, EI-MS (70 eV) (m/z) 360 (M⁺);
5i, EI-MS (70 eV) (m/z) 544 (M⁺).

EXAMPLE 42

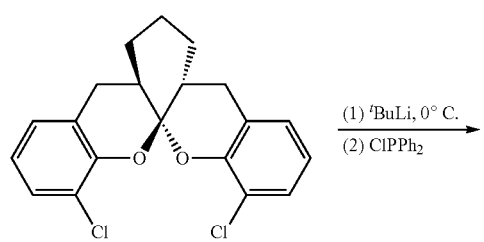

-continued

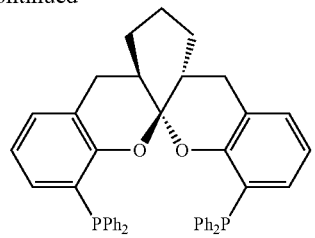

Substrate (R,R,R)-51 (722 mg, 2.0 mmol) and anhydrous tetrahydrofuran (10 mL) were added to a 50 mL of water-free and oxygen-free Schlenk tube and cooled to below −78° C. N-butyllithium (4 mL, 1.5 M in pentane, 6.0 mmol) was slowly added dropwise and the reaction mixture was stirred at below −78° C. for 0.5 hr. Chlorodiphenylphosphine (1.1 mL, 6.0 mmol) was slowly added dropwise and then naturally warmed to room temperature. The reaction mixture was stirred at room temperature for 10 hrs. 10 mL of distilled water was added to quench the reaction and the reaction mixture was extracted with dichloromethane (3×10 mL). The organic phase was dried on anhydrous sodium sulfate, filtered and concentrated. The residue was purified by column chromatography to obtain target product (R,R,R)-6a in 65% yield.

EXAMPLE 43

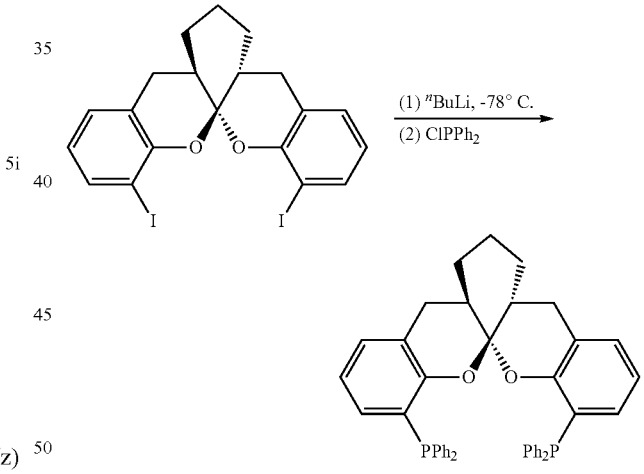

Substrate (R,R,R)-5m (544 mg, 1.0 mmol) and anhydrous tetrahydrofuran (10 mL) were added to a 50 mL of water-free and oxygen-free Schlenk tube and cooled to below −78° C. N-butyllithium (1.8 mL, 1.6 M in hexane, 3.0 mmol) was slowly added dropwise and the reaction mixture was stirred at below −78° C. for 0.5 hr. Chlorodiphenylphosphine (0.51 mL, 3.0 mmol) was slowly added dropwise and then naturally warmed to room temperature. The reaction mixture was stirred at room temperature for 10 hrs. 10 mL of distilled water was added to quench the reaction and the reaction mixture was extracted with dichloromethane (3×10 mL). The organic phase was dried on anhydrous sodium sulfate, filtered and concentrated. The residue was purified by column chromatography to obtain target product (R,R,R)-6a in 65% yield.

EXAMPLE 44

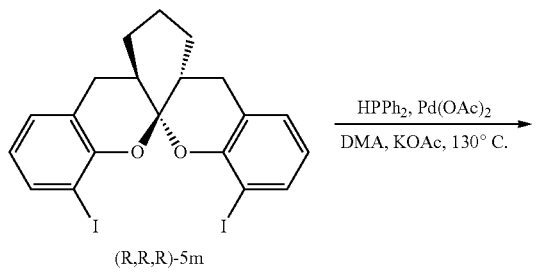

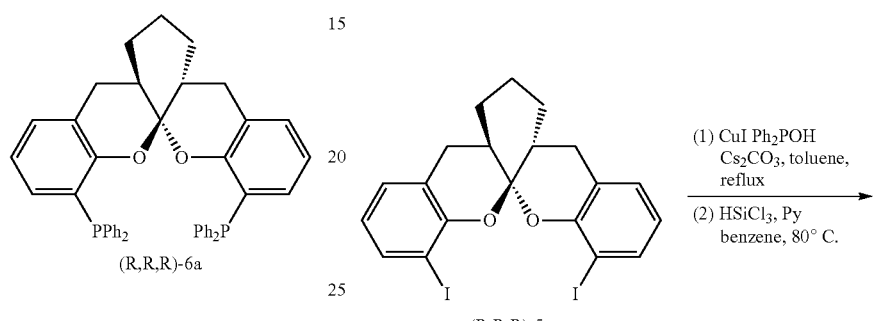

Under argon, palladium acetate (11.2 mg, 0.05 mmol), potassium acetate (215.8 mg, 2.2 mmol), (R,R,R)-5m (544 mg, 1.0 mmol) and diphenylphosphine (465 mg, 2.5 mmol) were added to a Schelenk tube. Anhydrous N,N-dimethylacetamide (DMA, 10 mL) was added and heated to 130° C. The reaction mixture was stirred for 6 hrs and then cooled to room temperature. 10 mL of distilled water was added to quench the reaction. The reaction mixture was extracted with dichloromethane (3×10 mL) and the organic phase was dried on anhydrous sodium sulfate. After filtered and concentrated, the residue was purified by column chromatography to obtain pure bisphosphine ligand (R,R,R)-6a in 79% yield.

EXAMPLE 45

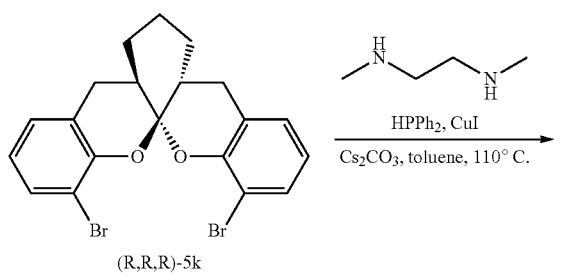

Under argon, cuprous iodide (47.6 mg, 0.25 mmol), cesium carbonate (2.44 g, 7.5 mmol), (R,R,R)-5k (900 mg, 2.0 mmol), N,N-dimethylethanediamine (154.2 mg, 1.75 mmol) and diphenylphosphine (930 mg, 5 mmol) were added to a Schelenk tube. Anhydrous toluene (20 mL) was added and heated to 110° C. The reaction mixture was stirred for 24 hrs and then cooled to room temperature. 50 mL of distilled water was added to quench the reaction. The reaction mixture was extracted with dichloromethane (3×10 mL) and the organic phase was dried on anhydrous sodium sulfate. After filtered and concentrated, the residue was purified by column chromatography to obtain pure bisphosphine ligand (R,R,R)-6a in 82% yield.

EXAMPLE 46

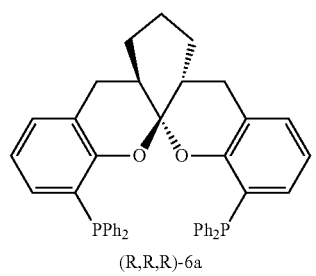

Under argon, cuprous iodide (19.4 mg, 0.1 mmol), cesium carbonate (390 mg, 1.2 mmol), (R,R,R)-5m (544 mg, 1.0 mmol) and diphenylphosphine oxide (465 mg, 2.5 mmol) were added to a 50 mL Schelenk tube. Anhydrous toluene (10 mL) was added and heated to reflux. The reaction mixture was stirred for 48 hrs and then cooled to room temperature. 10 mL of distilled water was added to quench the reaction. The reaction mixture was extracted with dichloromethane (3×20 mL) and the organic phase was dried on anhydrous sodium sulfate. After filtered and concentrated, the residue was purified by column chromatography. The obtained product was directly added to a 50 mL Schelenk tube and anhydrous benzene (10 mL) and pyridine (1.5 mL, 20 mmol) were added and cooled to 0° C. Trichlorosilane (1.0 mL, 10 mmol) was added and the reaction was carried out at 80° C. for 48 hrs. The reaction mixture was cooled to room temperature and saturated sodium bicarbonate aqueous solution (10 mL) was added to quench the reaction. The reaction mixture was extracted with dichloromethane (20 mL×3), and the resulting organic phase was dried on anhydrous sodium sulfate. After filtered and concentrated, the residue was purified by column chromatography to obtain (R,R,R)-6a as white solid in 62% yield.

EXAMPLE 47

(R,R,R)-6p was prepared according to the following reaction route.

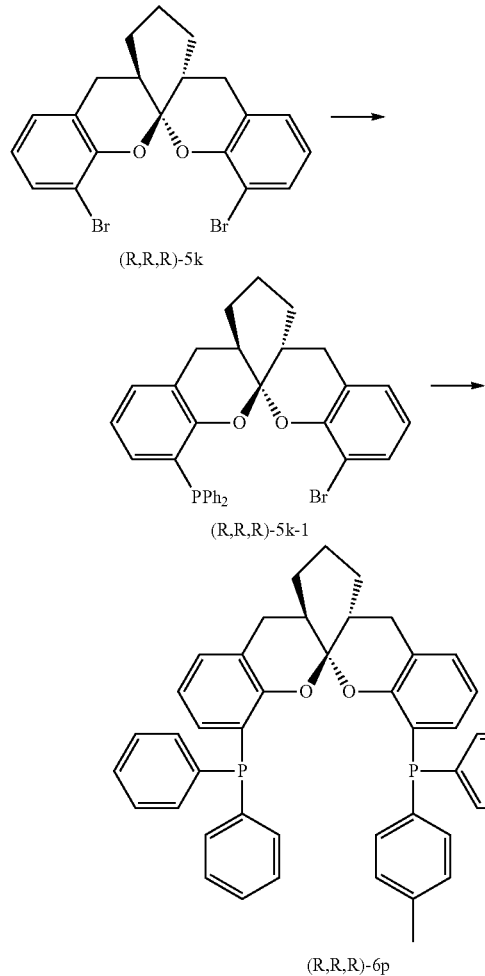

Substrate(R,R,R)-5k (350 mg, 0.77 mmol) and anhydrous tetrahydrofuran (6 mL) were added to a 50 mL of water-free and oxygen-free Schlenk tube and cooled to below −78° C. N-butyllithium (0.48 mL, 1.6 M in hexane, 0.77 mmol) was slowly added dropwise and the reaction mixture was stirred at −78° C. for 0.5 hr. Chlorodiphenylphosphine (0.15 mL, 0.77 mmol) was slowly added dropwise and then naturally warmed to room temperature. The reaction mixture was stirred at room temperature for 10 hrs. 15 mL of distilled water was added to quench the reaction and the reaction mixture was extracted with dichloromethane (3×20 mL). The organic phase was dried on anhydrous sodium sulfate, filtered and concentrated. The residue was purified by column chromatography to obtain target product (R,R,R)-5k-1 in 80% yield.

(R,R,R)-5k-1 (277.7 mg, 0.5 mmol) and anhydrous tetrahydrofuran (6 mL) were added to a 50 mL of water-free and oxygen-free Schlenk tube and cooled to below −78° C. N-butyllithium (0.31 mL, 1.6 M in hexane, 0.5 mmol) was slowly added dropwise and the reaction mixture was stirred at −78° C. for 0.5 hr. Chlorodi(p-tolyl)phosphine (0.10 mL, 0.5 mmol) was slowly added dropwise and then naturally warmed to room temperature. The reaction mixture was stirred at room temperature for 10 hrs. 15 mL of distilled water was added to quench the reaction and the reaction mixture was extracted with dichloromethane (3×20 mL). The organic phase was dried on anhydrous sodium sulfate, filtered and concentrated. The residue was purified by column chromatography to obtain target product (R,R,R)-6p in 74% yield.

(R,R,R)-5k-1, white solid, Mp 109-110° C., $[\alpha]_D^{20}$=+89.1 (c 1.00, CHCl$_3$). $^1$H NMR (400 MHz, CDCl$_3$) δ=7.92-7.77 (m, 3H), 7.55-7.50 (m, 2H), 7.37-7.24 (m, 8H), 7.04-7.00 (m, 1H), 6.88-6.86 (m, 1H), 6.70-6.66 (m, 1H), 3.04 (dd, J=16.8 Hz, 5.6 Hz, 1H), 2.54-2.40 (3H), 2.09-2.05 (m, 1H), 1.83-1.76 (m, 1H), 1.58-1.56 (m, 1H), 1.44-0.97 (in, 5H) ppm. $^{31}$P (162 MHz, CDCl$_3$) δ −15.1 ppm.

(R,R,R)-6p, white solid, Mp 99-101° C., $[\alpha]_D^{20}$=+129.1 (c 1.00, CHCl$_3$). $^1$H NMR (400 MHz, CDCl$_3$) δ 7.37-7.21 (m, 22H), 6.68-6.46 (m, 2H), 2.39-2.28 (m, 4H), 2.21 (s, 6H), 1.99-1.87 (m, 2H), 1.32-1.28 (m, 2H), 1.21-1.19 (m, 4H) ppm; $^{31}$P (162 MHz, CDCl$_3$) δ −15.3, −19.6 ppm.

EXAMPLE 48

(R,R,R)-6q was prepared according to the following reaction route.

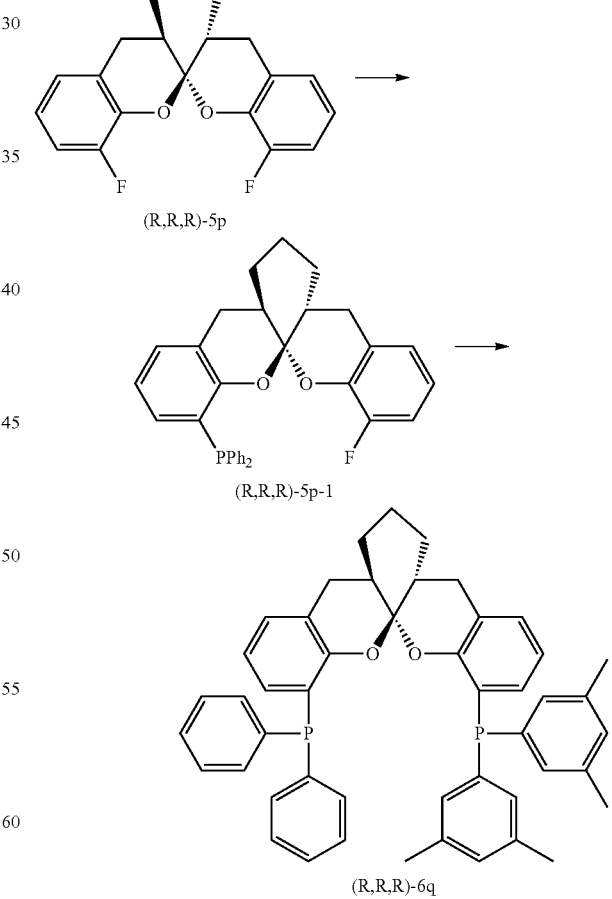

(R,R,R)-5p (328 mg, 1.0 mmol), anhydrous tetrahydrofuran (4 mL) and potassium diphenyl phosphine (KPPh$_2$, 2.0 mL, 0.5 mol/L in THF, 1.0 mmol) were added to a 50 mL of water-free and oxygen-free Schlenk tube and heated to reflux for 10 hrs. After cooled, 10 mL of distilled water was added to quench the reaction and the reaction mixture was extracted with dichloromethane (3×10 mL). The organic phase was dried on anhydrous sodium sulfate, filtered and concentrated. The residue was purified by column chromatography to obtain compound (R,R,R)-5p-1 in 74% yield.

(R,R,R)-5p-1 (296.7 mg, 0.6 mmol), anhydrous tetrahydrofuran (4 mL), bis(3,5-ditolyl)phosphine (155 mg, 0.6 mmol) and potassium tert-butoxide (67.3 mg, 0.6 mmol) were added to a 50 mL of water-free and oxygen-free Schlenk tube and heated to reflux for 10 hrs. After cooled, 10 mL of distilled water was added to quench the reaction and the reaction mixture was extracted with dichloromethane (3×10 mL). The organic phase was dried on anhydrous sodium sulfate, filtered and concentrated. The residue was purified by column chromatography to obtain target product (R,R,R)-6q in 80% yield.

(R,R,R)-5p-1, white solid, Mp 107-110° C., $[\alpha]_D^{20}$=+104.2 (c 1.10, CHCl$_3$). $^1$H NMR (400 MHz, CDCl3) δ=7.88-7.7.74 (m, 3H), 7.48-7.34 (m, 9H), 7.03-6.87 (m, 1H), 6.85-6.67 (m, 3H), 2.93 (dd, J=16.4 Hz, 5.2 Hz, 1H), 2.66 (dd, J=16.4 Hz, 6.8 Hz, 1H), 2.44-2.42 (m, 2H), 2.21-2.18 (m, 1H), 1.91-1.85 (m, 1H), 1.70-1.67 (m, 1H), 1.50-1.08 (m, 5H) ppm; $^{31}$P (162 MHz, CDCl$_3$) δ −17.1 ppm; $^{19}$F-NMR (376 MHz, CDCl$_3$) δ −136.6 ppm.

(R,R,R)-6q, Mp 105-107° C., $[\alpha]_D^{20}$=+136.6 (c 1.40, CHCl$_3$). $^1$H NMR (400 MHz, CDCl$_3$) 7.49-7.24 (m, 20H), 6.75-6.59 (m, 2H), 6.21-6.13 (m, 2H), 2.43-2.32 (m, 4H), 2.29 (s, 6H), 2.21 (s, 6H), 2.03-1.98 (m, 2H), 1.35-1.29 (m, 2H), 1.25-1.21 (m, 4H) ppm; $^{31}$P (162 MHz, CDCl$_3$) δ −14.5, −20.4 ppm.

EXAMPLE 49

(R,R,R)-6a was prepared according to the following reaction route.

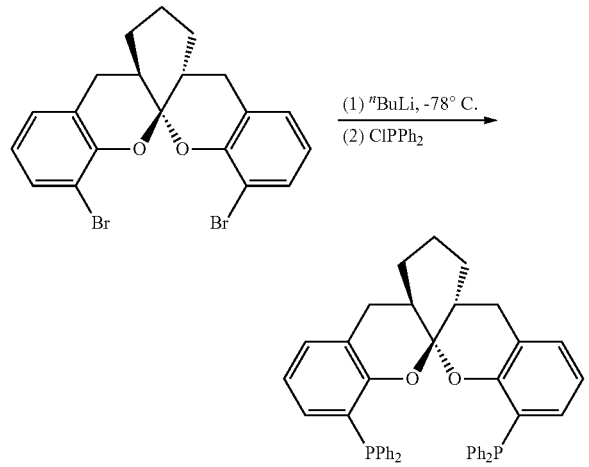

(R,R,R)-5a  (R,R,R)-6a

Substrate (R,R,R)-5a (175 mg, 0.389 mmol) and anhydrous tetrahydrofuran (4 mL) were added to a 10 mL of water-free and oxygen-free Schlenk tube and cooled to below −78° C. N-butyllithium (0.39 mL, 2.5 M in hexane, 0.972 mmol) was slowly added dropwise and the reaction mixture was stirred at −78° C. for 0.5 hr. Chlorodiphenylphosphine (0.18 mL, 0.972 mmol) was slowly added dropwise and then naturally warmed to room temperature. The reaction mixture was stirred at room temperature for 10 hrs. 10 mL of distilled water was added to quench the reaction and the reaction mixture was extracted with dichloromethane (3×10 mL). The organic phase was dried on anhydrous sodium sulfate, filtered and concentrated. The residue was purified by column chromatography to obtain target product (R,R,R)-6a (187 mg, 73% yield).

EXAMPLE 50 catalysts were prepared on site by using different bisphosphine ligands (R,R,R)-6 and metal salt [Pd(η-C$_3$H$_5$)Cl]$_2$ and used in the asymmetric allyl amination of Morita-Baylis-Hillman conjugate 8a to prepare chiral α-alkylidene-β-amino carboxy acid derivative 9a.

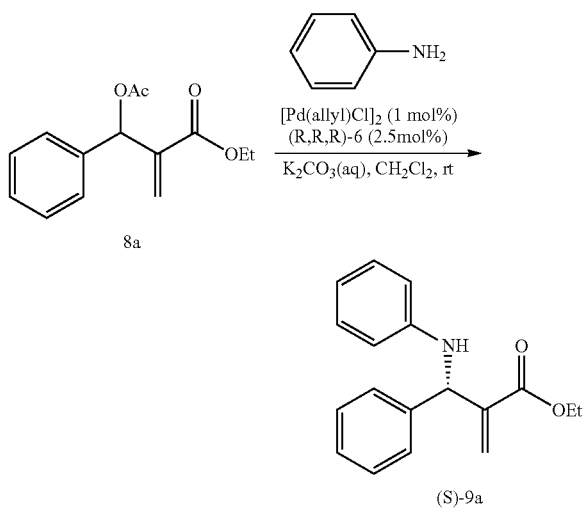

The reaction was conducted as follows: under argon atmosphere, [Pd(C$_3$H$_5$)Cl]$_2$ (1.8 mg, 0.005 mmol) and bisphosphine ligand (R,R,R)-6 (0.0125 mmol) were separately added to a schlenk tube. Anhydrous CH$_2$Cl$_2$ (5 mL) was added and stirred at room temperature for 10 mins to obtain the catalyst. Substrate 8a (124.1 mg, 0.5 mmol), K$_2$CO$_3$ (1.0 M aqueous solution, 1.5 mL, 1.5 mmol) and aniline (140 mg, 1.5 mmol) were successively added and stirred at room temperature for 3 hrs. The reaction mixture was extracted with dichloromethane (3×10 mL), dried on anhydrous sodium sulfate, filtered, concentrated and purified by column chromatography to obtain viscous liquid (S)-9a. The results of preparing (S)-9a through asymmetric amination by using 8a as the substrate and complexes of different bisphosphine ligands (R,R,R)-6 and metal palladium as catalysts were shown in table 2.

TABLE 2

| results of asymmetric amination | | | |
|---|---|---|---|
| | ligand | yield of (S)-9a | ee (%) |
| 1 | (R,R,R)-6a | 90 | (+)-94 |
| 2 | (R,R,R)-6b | 71 | (+)-59 |
| 3 | (R,R,R)-6c | 89 | (+)-96 |
| 4 | (R,R,R)-6d | 89 | (+)-95 |
| 5 | (R,R,R)-6e | 90 | (+)-93 |
| 6 | (R,R,R)-6f | 87 | (+)-89 |
| 7 | (R,R,R)-6g | 88 | (+)-90 |
| 8 | (R,R,R)-6h | 85 | (+)-89 |

TABLE 2-continued results of asymmetric amination

| | ligand | yield of (S)-9a | ee (%) |
|---|---|---|---|
| 9 | (R,R,R)-6i | 80 | (+)-87 |
| 10 | (R,R,R)-6j | 82 | (+)-93 |
| 11 | (R,R,R)-6k | 87 | (+)-93 |
| 12 | (R,R,R)-6l | 81 | (+)-88 |
| 13 | (R,R,R)-6m | 79 | (+)-87 |
| 14 | (R,R,R)-6n | 80 | (+)-92 |
| 15 | (R,R,R)-6o | 85 | (+)-93 |
| 16 | (R,R,R)-6p | 89 | (+)-91 |
| 17 | (R,R,R)-6q | 92 | (+)-94 |

(S)-9a, $[\alpha]_D^{20}$=+120.0 (c 1.00, CHCl$_3$), 96% ee (determined by high performance liquid chromatography, chiral AD-H column; n-hexane/isobutanol=95:5, 1.0 mL/min, 254 nm; $t_R$ (major)=7.07 min; $t_R$ (minor)=7.81 min). $^1$H NMR (400 MHz, CDCl$_3$) δ=7.38-7.27 (m, 5H), 7.16 (t, J=8.4 Hz, 2H), 6.72 (t, J=7.2 Hz, 1H), 6.57 (d, J=8.8 Hz, 2H), 6.38 (s, 1H), 5.94 (s, 1H), 5.40 (d, J=4.8 Hz, 1H), 4.19-4.09 (m, 3H), 1.20 (t, J=7.2 Hz, 3H) ppm; $^{13}$C NMR (100 MHz, CDCl$_3$) δ=166.1, 146.6, 140.6, 140.2, 129.1, 128.7, 127.7, 127.5, 125.9, 117.8, 113.3, 60.7, 59.0, 14.0 ppm.

EXAMPLE 51

The catalyst was prepared on site by using bisphosphine ligand (R,R,R)-6c and metal [Pd(C$_3$H$_5$)Cl]$_2$ to catalyze asymmetric allyl amination of Morita-Baylis-Hillman adduct 8. The reaction equation was shown as follows.

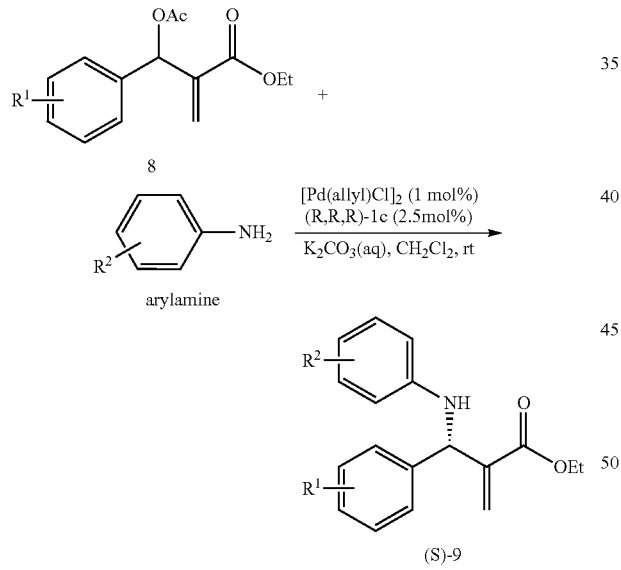

The reaction was conducted as follows: under argon atmosphere, [Pd(C$_3$H$_5$)Cl]$_2$ (1.8 mg, 0.005 mmol) and (R,R,R)-6c (9.6 mg, 0.0125 mmol) were separately added to a schlenk tube. Anhydrous CH$_2$Cl$_2$ (5 mL) was added and stirred at room temperature for 10 mins. Substrate 8 (0.5 mmol), K$_2$CO$_3$ (1.0 M aqueous solution, 1.5 mL, 1.5 mmol) and arylamine (1.5 mmol) were successively added and stirred at room temperature for 3 hrs. The reaction mixture was extracted with dichloromethane (3×10 mL), dried on anhydrous sodium sulfate, filtered, concentrated and purified by column chromatography to obtain chiral amination product (S)-9. The results were shown as follows.

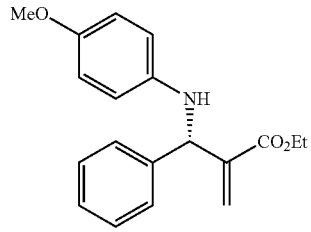 [SMILES: C=C(C(=O)OCC)[C@@H](Nc1ccc(OC)cc1)c1ccccc1]

(S)-9b, colourless liquid, 88% yield, $[\alpha]_D^{20}$=+98.4 (c 1.00, CHCl$_3$), 95% ee (determined by high performance liquid chromatography, chiral AD-H column; n-hexane/isobutanol=95:5, 1.0 mL/min, 254 mm; $t_R$ (major)=11.08 min; $t_R$ (minor)=12.12 min). $^1$H NMR (400 MHz, CDCl$_3$) δ=7.38-7.25 (m, 5H), 6.75 (d, J=8.8 Hz, 2H), 6.54 (d, J=9.2 Hz, 2H), 6.37 (s, 1H), 5.93 (s, 1H), 5.32 (s, 1H), 4.18-4.09 (m, 2H), 3.94 (s, 1H), 3.72 (s, 3H), 1.20 (t, J=7.2 Hz, 3H) ppm; $^{13}$C NMR (100 MHz, CDCl$_3$) δ=166.2, 152.2, 141.0, 140.9, 140.5, 128.6, 127.6, 127.4, 125.8, 114.7, 114.6, 60.7, 59.7, 55.7, 14.0 ppm.

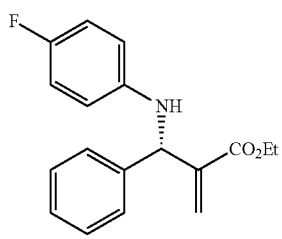 [SMILES: C=C(C(=O)OCC)[C@@H](Nc1ccc(F)cc1)c1ccccc1]

(S)-9c, colourless liquid, 89% yield, $[\alpha]_D^{20}$=+78.9 (c 1.00, CHCl$_3$), 95% ee (determined by high performance liquid chromatography, chiral AD-H column; n-hexane/isobutanol=99:1, 1.0 mL/min, 254 nm; $t_R$ (major)=18.31 min; $t_R$ (minor)=22.32 min). $^1$H NMR (400 MHz, CDCl$_3$) δ=7.37-7.25 (m, 5H), 6.86 (t, J=8.8 Hz, 2H), 6.51-6.48 (m, 2H), 6.37 (s, 1H), 5.89 (s, 1H), 5.33 (s, 1H), 4.16-4.13 (m, 2H), 4.08 (s, br, 1H), 1.21 (t, J=7.2 Hz, 3H) ppm; $^{13}$C NMR (100 MHz, CDCl$_3$) δ=166.1, 155.9 (d, $J_{(P,C)}$=234.0 Hz), 143.0 (d, $J_{(F,C)}$=1.8 Hz), 140.4 (d, $J_{(F,C)}$=23.4 Hz), 128.7 (s), 127.7 (s), 127.4 (s), 125.9 (s), 115.6 (s), 115.4 (s), 114.2 (d, $J_{(F,C)}$=7.4 Hz), 60.8, 59.5, 14.0 ppm; $^{19}$F-NMR (376 MHz, CDCl$_3$) δ −127.4 ppm.

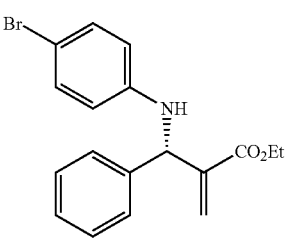 [SMILES: C=C(C(=O)OCC)[C@@H](Nc1ccc(Br)cc1)c1ccccc1]

(S)-9d, white solid, 83% yield. Mp 78-80° C., $[\alpha]_D^{20}$=+115.0 (c 1.00, CHCl$_3$), 95% ee (determined by high performance liquid chromatography, chiral AD-H column; n-hexane/isobutanol=98:2, 1.0 mL/min, 254 nm; $t_R$ (major)=16.31 min; $t_R$ (minor)=18.01 min). $^1$H NMR (400 MHz, CDCl$_3$) δ=7.33-7.19 (m, 7H), 6.42 (d, J=8.8 Hz, 2H), 6.36 (s, 1H), 5.85 (s, 1H), 5.35 (s, 1H), 4.16-4.05 (m, 3 H), 1.18

(t, J=7.2 Hz, 3H) ppm; $^{13}$C NMR (100 MHz, CDCl$_3$) δ=165.9, 145.5, 140.0, 139.8, 131.7, 128.6, 127.7, 127.3, 125.9, 114.9, 109.3, 60.7, 58.8, 13.9 ppm. The absolute configuration of obtained compound 9d was (S) determined by X-ray crystal diffraction diagram and the absolute configurations of other chiral α-alkylidene-β-amino carboxy acid derivatives 9a-9c and 9e-9k were determined by comparison of Cotton effect with (S)-9d.

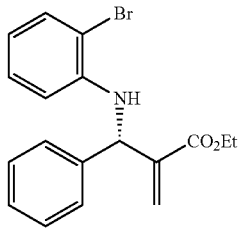 [SMILES: C=C(C(=O)OCC)[C@@H](Nc1ccccc1Br)c1ccccc1]

(S)-9e, colourless liquid, 67% yield, [α]$_D^{20}$=+53.3 (c 1.00, CHCl$_3$), 96% ee (determined by high performance liquid chromatography, chiral AD-H column; n-hexane/isobutanol=99:1, 1.0 mL/min, 254 nm; t$_R$ (major)=7.96 min; t$_R$ (minor)=8.76 min). $^1$H NMR (400 MHz, CDCl$_3$) δ=7.43-7.25 (m, 6H), 7.11 (t, J=10.8 Hz, 1H), 6.59-6.54 (m, 2H), 6.38 (s, 1H), 5.85 (s, 1H), 5.49 (d, J=8.0 Hz, 1 H), 4.87 (d, J=7.6 Hz, 1H), 4.21-4.10 (m, 2H), 1.20 (t, J=9.2 Hz, 3H) ppm; $^{13}$C NMR (100 MHz, CDCl$_3$) δ=165.9, 143.4, 140.0, 139.9, 132.2, 128.7, 128.3, 127.7, 127.3, 125.9, 118.2, 112.4, 109.8, 60.8, 58.5, 13.9 ppm.

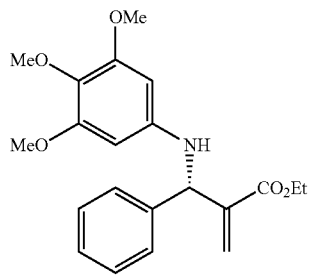 [SMILES: C=C(C(=O)OCC)[C@@H](Nc1cc(OC)c(OC)c(OC)c1)c1ccccc1]

(S)-9f, colourless liquid, 85% yield, [α]$_D^{20}$=+86.6 (c 1.00, CHCl$_3$), 96% ee (determined by high performance liquid chromatography, chiral AD-H column; n-hexane/isobutanol=85:15, 1.0 mL/min, 254 nm; t$_R$ (major)=10.38 min; t$_R$ (minor)=12.36 min). $^1$H NMR (400 MHz, CDCl$_3$) δ=7.38-7.24 (m, 5H), 6.39 (s, 1H), 5.95 (s, 1H), 5.82 (s, 2H), 5.40 (s, 1H), 4.19-4.10 (m, 3H), 3.73 (s, 9H), 1.20 (t, J=7.2 Hz, 3H) ppm; $^{13}$C NMR (100 MHz, CDCl$_3$) δ=166.0, 153.5, 143.3, 140.4, 130.0, 128.5, 127.5, 127.2, 125.7, 90.8, 60.7, 60.6, 59.0, 55.6, 13.8 ppm.

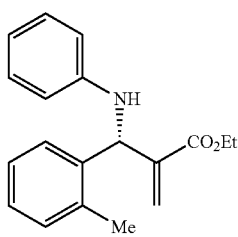 [SMILES: C=C(C(=O)OCC)[C@@H](Nc1ccccc1)c1ccccc1C]

(S)-9 g, white solid, 64% yield. Mp 93-94° C., [α]$_D^{20}$=+146.5 (c 1.00, CHCl$_3$), 91% ee (determined by high performance liquid chromatography, chiral AD-H column; n-hexane/isobutanol=98:2, 1.0 mL/min, 254 nm; t$_R$ (major)= 6.91 min; t$_R$ (minor)=8.44 min). $^1$H NMR (400 MHz, CDCl$_3$) δ=7.24-7.13 (m, 6H), 6.71 (t, J=7.2 Hz, 1H), 6.55 (d, J=8.0 Hz, 2H), 6.43 (s, 1H), 5.89 (s, 1H), 5.60 (s, 1H), 4.20-4.07 (m, 2H), 3.85 (s, br, 1H), 2.40 (s, 3H), 1.18 (t, J=7.2 Hz, 3H) ppm; $^{13}$C NMR (100 MHz, CDCl$_3$) δ=166.4, 146.8, 140.0, 138.7, 136.7, 130.7, 129.1, 127.7, 126.3, 126.2, 126.0, 117.6, 112.8, 60.7, 54.7, 19.1, 14.0 ppm.

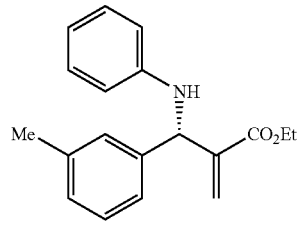 [SMILES: C=C(C(=O)OCC)[C@@H](Nc1ccccc1)c1cccc(C)c1]

(S)-9 h, white solid, 89% yield. Mp 56-57° C., [α]$_D^{20}$=+131.8 (c 1.00, CHCl$_3$), 97% ee (determined by high performance liquid chromatography, chiral AD-H column; n-hexane/isobutanol=98:2, 1.0 mL/min, 254 nm; t$_R$ (major)= 9.52 min; t$_R$ (minor)=11.05 min). $^1$H NMR (400 MHz, CDCl$_3$) δ=7.21-7.07 (m, 6H), 6.70 (t, J=7.6 Hz, 1H), 6.56 (d, J=8.4 Hz, 2H), 6.37 (s, 1H), 5.93 (s, 1H), 5.36 (s, 1H), 4.19-4.08 (m, 3H), 2.33 (s, 3H), 1.20 (t, J=7.2 Hz, 3H) ppm; $^{13}$C NMR (100 MHz, CDCl$_3$) δ=166.2, 146.7, 140.6, 140.2, 138.3, 129.1, 128.5, 128.4, 128.2, 125.7, 124.5, 117.7, 113.3, 60.7, 58.9, 21.4, 14.0 ppm.

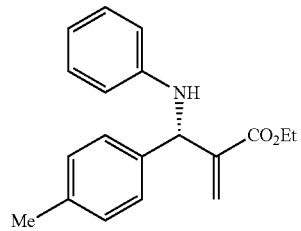 [SMILES: C=C(C(=O)OCC)[C@@H](Nc1ccccc1)c1ccc(C)cc1]

(S)-9i, colourless liquid, 90% yield, [α]$_D^{20}$=+129.6 (c 1.00, CHCl$_3$), 95% ee (determined by high performance liquid chromatography, chiral AD-H column; n-hexane/isobutanol=98:2, 1.0 mL/min, 254 nm; t$_R$ (major)=12.55 min; t$_R$ (minor)=14.98 min). $^1$H NMR (400 MHz, CDCl$_3$) δ=7.26-7.22 (m, 2H), 7.16-7.12 (m, 4H), 6.70 (t, J=8.4 Hz, 1H), 6.56 (d, J=8.4 Hz, 2H), 6.36 (s, 1H), 5.92 (s, 1H), 5.36 (s, 1H), 4.18-4.09 (m, 3H), 2.32 (s, 3H), 1.21 (t, J=7.6 Hz, 3H) ppm; $^{13}$C NMR (100 MHz, CDCl$_3$) δ=166.2, 146.7, 140.3, 137.7, 137.4, 129.3, 129.1, 127.4, 125.5, 117.7, 113.3, 60.7, 58.6, 21.0, 14.0 ppm.

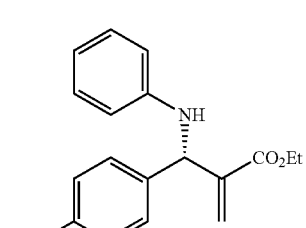

(S)-9j, colourless liquid, 96% yield, $[\alpha]_D^{20}$=+132.6 (c 1.00, CHCl$_3$), 95% ee (determined by high performance liquid chromatography, chiral AD-H column; n-hexane/isobutanol=98:2, 1.0 mL/min, 254 nm; $t_R$ (major)=20.63 min; $t_R$ (minor)=23.04 min). $^1$H NMR (400 MHz, CDCl$_3$) δ=7.28 (d, J=8.4 Hz, 2H), 7.15 (t, J=7.6 Hz, 2H), 6.86 (d, J=8.4 Hz, 2H), 6.71 (t, J=7.2 Hz, 1H), 6.56 (d, J=8.0 Hz, 2H), 6.35 (s, 1H), 5.92 (s, 1H), 5.35 (s, 1H), 4.19-4.09 (m, 3H), 3.78 (s, 3H), 1.21 (t, J=7.2 Hz, 3H) ppm; $^{13}$C NMR (100 MHz, CDCl$_3$) δ=166.2, 159.0, 146.7, 140.3, 132.7, 129.0, 128.6, 125.3, 117.7, 114.0, 113.3, 60.7, 58.3, 55.2, 14.0 ppm.

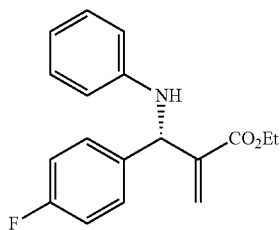 [SMILES: C=C(C(=O)OCC)[C@@H](Nc1ccccc1)c1ccc(F)cc1]

(S)-9k, colourless liquid, 96% yield, $[\alpha]_D^{20}$=+89.9 (c 1.00, CHCl$_3$), 97% ee (determined by high performance liquid chromatography, chiral AD-H column; n-hexane/isobutanol=98:2, 1.0 mL/min, 254 nm; $t_R$ (major)=12.72 min; $t_R$ (minor)=13.89 min). $^1$H NMR (400 MHz, CDCl$_3$) δ=7.35-7.32 (m, 2H), 7.16 (t, J=8.0 Hz, 2H), 7.01 (t, J=8.8 Hz, 2H), 6.73 (t, J=7.2 Hz, 1H), 6.57 (d, J=8.0 Hz, 2H), 6.38 (s, 1H), 5.92 (s, 1H), 5.38 (s, 1H), 4.18-4.13 (m, 3H), 1.21 (t, J=6.8 Hz, 3H) ppm; $^{13}$C NMR (100 MHz, CDCl$_3$) δ=166.0, 162.2 (d, $J_{(F,C)}$=244.0 Hz), 146.5 (s), 140.1 (s), 136.4 (d, $J_{(F,C)}$=2.9 Hz), 129.1 (d, $J_{(F,C)}$=7.8 Hz), 126.0 (s), 118.0 (s), 115.6 (s), 115.4 (s), 113.4 (s), 60.8, 58.3, 14.0 ppm; $^{19}$F-NMR (376 MHz, CDCl$_3$) δ −114.6 ppm.

EXAMPLE 52

Compounds of formulae 3n-Bn-3p-Bn were prepared according to the preparation method of example 1, respectively.

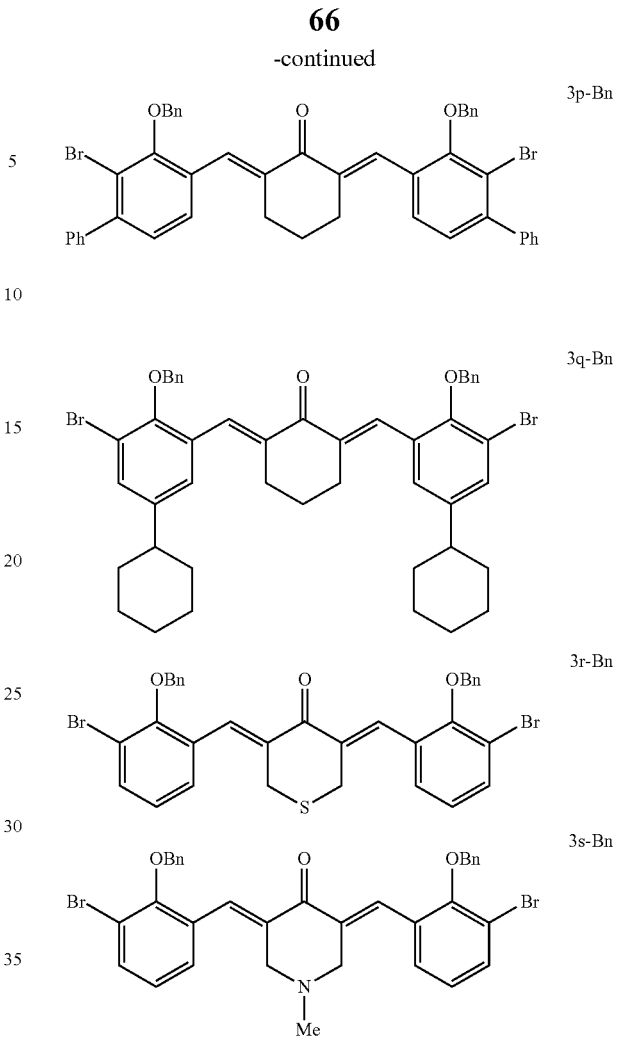

3n-Bn, ESI-MS m/z: 555.1 [M+H$^+$]; 3o-Bn, ESI-MS m/z: 763.0 [M+H$^+$];

3p-Bn, ESI-MS m/z: 795.1 [M+H$^+$]; 3q-Bn, ESI-MS m/z: 807.1 [M+H$^+$];

3r-Bn, ESI-MS m/z: 660.0 [M+H$^+$]; 3s-Bn, ESI-MS m/z: 658.0 [M+H$^+$].

EXAMPLE 53

Compounds of formulae (R,R,R)-5n-(R,R,R)-5s were prepared according to the preparation method of example 5 by using compounds 3n-Bn-3s-Bn as raw material, respectively.

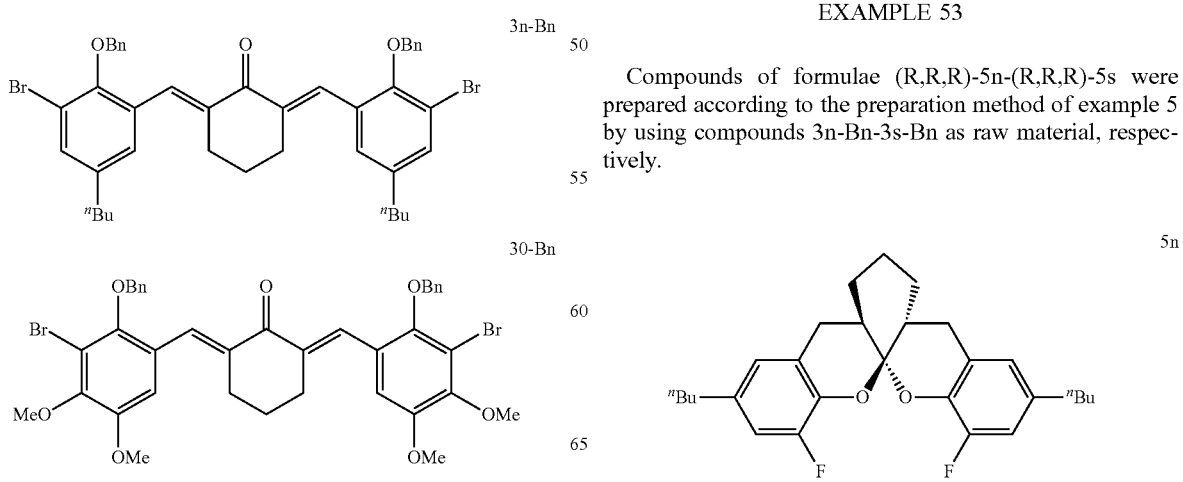

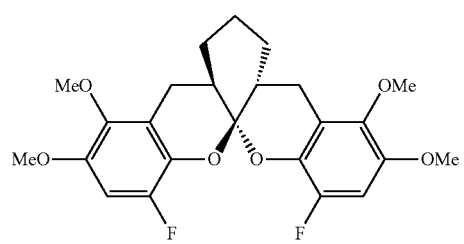

5o

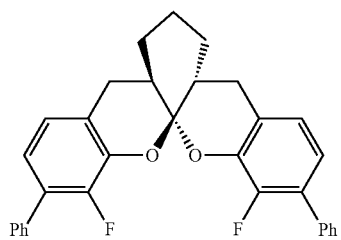

5p

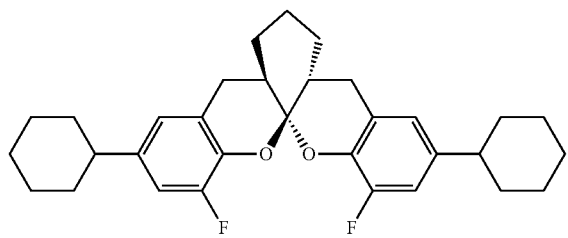

5q

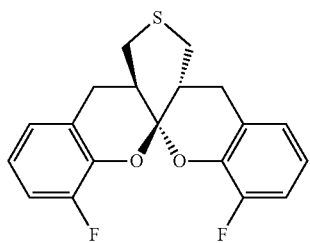

5r

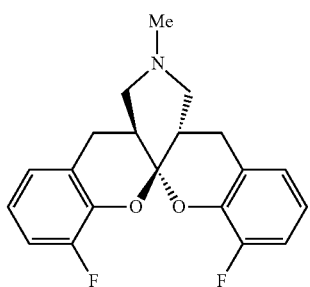

5s

5n, EI-MS (70 eV) (m/z) 440 (M$^+$); 5o, EI-MS (70 eV) (m/z) 448 (M$^+$);

5p, EI-MS (70 eV) (m/z) 480 (M$^+$); 5q, EI-MS (70 eV) (m/z) 492 (M$^+$);

5r, EI-MS (70 eV) (m/z) 346 (1M$^+$); 5s, EI-MS (70 eV) (m/z) 343 (M$^+$).

Similarly, compounds of formulae (S,S,S)-5n-(S,S,S)-5s were prepared according to the preparation method of example 16 by using compounds 3n-Bn-3s-Bn as raw material, respectively.

EXAMPLE 54

Compounds of formulae (R,R,R)-6r-(R,R,R)-6w were prepared according to the preparation method of example 16 by using compounds (R,R,R)-5n-(R,R,R)-5s as raw material, respectively.

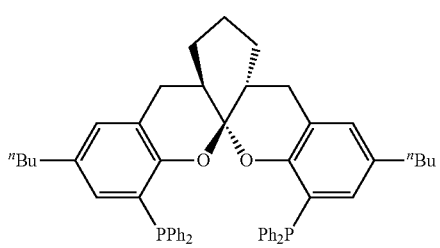

6r

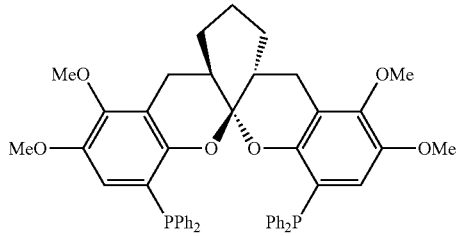

6s

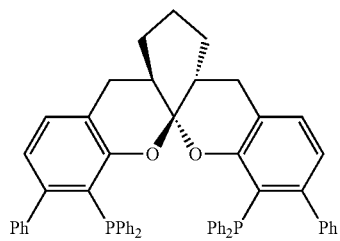

6t

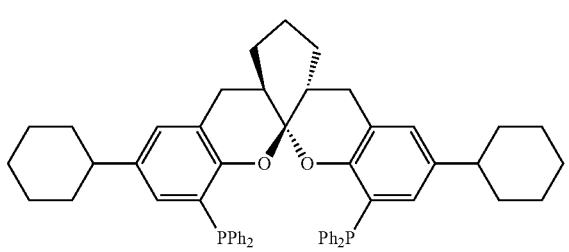

6u

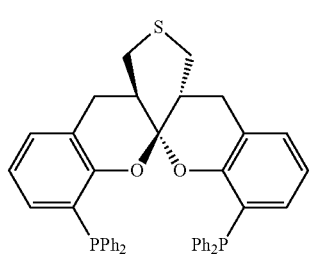

6v

-continued

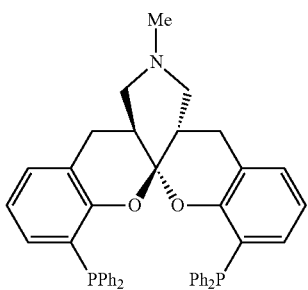

6w

6r, ESI-MS m/z: 773.8 [M+H$^+$]; 6s, ESI-MS m/z: 781.5 [M+H$^+$];
6t, ESI-MS m/z: 813.4 [M+H$^+$], 835.2 [M+Na$^+$]; 6u, ESI-MS m/z: 826.2 [M+H$^+$];
6v, ESI-MS m/z: 679.9 [M+H$^+$]; 6w, ESI-MS m/z: 676.8 [M+H$^+$].

Compounds of formulae (S,S,S)-6r-(S,S,S)-6w were prepared according to the preparation method of example 41 by using compounds (S,S,S)-5n-(S,S,S)-5s as raw material, respectively.

Racemic 6r-6w compounds were prepared according to the preparation method of example 43 by using racemic compounds 5k-5p as raw material, respectively.

EXAMPLE 55

The catalyst was prepared on site by using ligands (R,R,R)-6r-(R,R,R)-6w and metal salt [Pd(η-C$_3$H$_5$)Cl]$_2$, and used in asymmetric allyl amination of Morita-Baylis-Hillman conjugate 8 to prepare chiral α-alkylidene-β-amino carboxy acid derivative 9a.

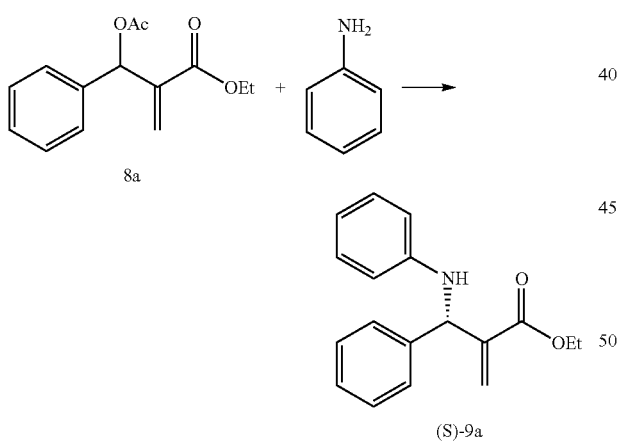

The reaction was conducted as follows: under argon atmosphere, [Pd(C$_3$H$_5$)Cl]$_2$ (1.8 mg, 0.005 mmol) and bis-phosphine ligands (R,R,R)-6 k-6p (0.0125 mmol) were separately added to a schlenk tube. Anhydrous CH$_2$Cl$_2$ (5 mL) was added and stirred at room temperature for 10 mins to obtain the catalyst. Substrate 8a (124.1 mg, 0.5 mmol), K$_2$CO$_3$ (1.0 M aqueous solution, 1.5 mL, 1.5 mmol) and aniline (140 mg, 1.5 mmol) were successively added and stirred at room temperature for 3 hrs. The reaction mixture was extracted with dichloromethane (3×10 mL), dried on anhydrous sodium sulfate, filtered, concentrated and purified by column chromatography to obtain viscous liquid (S)-9a.

TABLE 3 results of asymmetric amination

| | ligand | yield of (S)-9a (%) | ee (%) |
|---|---|---|---|
| 1 | (R,R,R)-6r | 89 | (+)-91 |
| 2 | (R,R,R)-6s | 91 | (+)-92 |
| 3 | (R,R,R)-6t | 85 | (+)-88 |
| 4 | (R,R,R)-6u | 83 | (+)-93 |
| 5 | (R,R,R)-6v | 90 | (+)-90 |
| 6 | (R,R,R)-6w | 88 | (+)-92 |

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A preparation method for a compound of formula I, comprising a step of synthesizing the compound of formula I from a compound of formula II by reacting a compound of formula II with a reagent selected from the group consisting of R$^4$$_2$PH, KPR$^4$$_2$, LiPR$^4$$_2$, KPR$^5$$_2$, and LiPR$^5$$_2$,

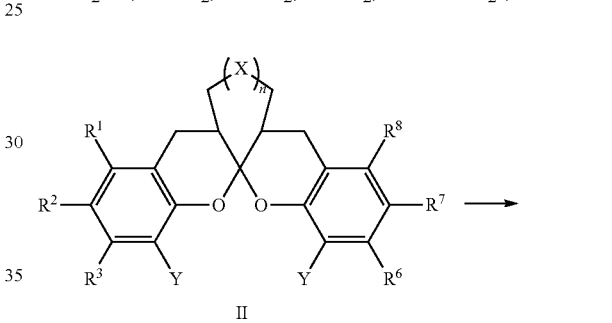

wherein R$^1$, R$^2$, R$^3$, R$^6$, R$^7$ and R$^8$ are each independently a hydrogen, a halogen, or a substituted or unsubstituted group selected from the group consisting of a C$_1$-C$_{10}$ alkyl, a C$_1$-C$_4$ alkoxyl, a C$_3$-C$_{30}$ cycloalkyl, and an aryl;
R$^4$ and R$^5$ are each independently a substituted or unsubstituted group selected from the group consisting of C3-C$_{10}$ cycloalkyl, a C$_1$-C$_{10}$ alkyl, 2-furyl, and an aryl;
X is selected from the group consisting of CH$_2$, NH, NCH$_3$, O, and S;
n=0-4;
wherein a substituent for substitution is a halogen, a C1-6 alkyl, a C$_{1-6}$ haloalkyl, or a C$_{1-6}$ alkoxyl;
Y is F, Cl, Br or I; and
wherein when R$^4$ and R$^5$ are the same, the step of synthesizing the compound of formula I comprises reacting a compound of formula II with a reagent selected from the group consisting of R$^4$$_2$PH, KPR$^4$$_2$, and LiPR$^4$$_2$, and when R$^4$ and R$^5$ are different, the step of synthesizing the compound of formula I comprises reacting a compound of formula II with a reagent selected from the group consisting of $KPR^4_2$ and $LiPR^4_2$, and then reacting with a reagent selected from the group consisting of $KPR^5_2$ and $LiPR^5_2$;

provided that when the reagent is $KPR^4_2$, $LiPR^4_2$, $KPR^5_2$, or $LiPR^4_2$, then Y is F.

2. The preparation method of claim 1, wherein $R^5$ and $R^4$ are the same and the method comprises the following step (a3):

(a3) reacting the compound of formula II with $R^4_2PH$ in an organic solvent and in the presence of a metal catalyst to obtain the compound of formula I:

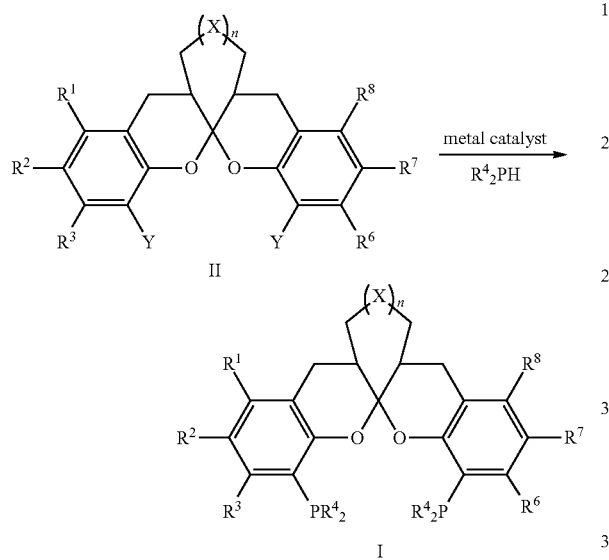

wherein Y is Cl, Br, or I; and $R^1$, $R^2$, $R^3$, $R^4$, $R^6$, $R^7$, $R^8$, X and n are defined as in claim 1; or the following step of reacting the compound of formula II with $KPR^4_2$ or $LiPR^4_2$ in an organic solvent to form the compound of formula I:

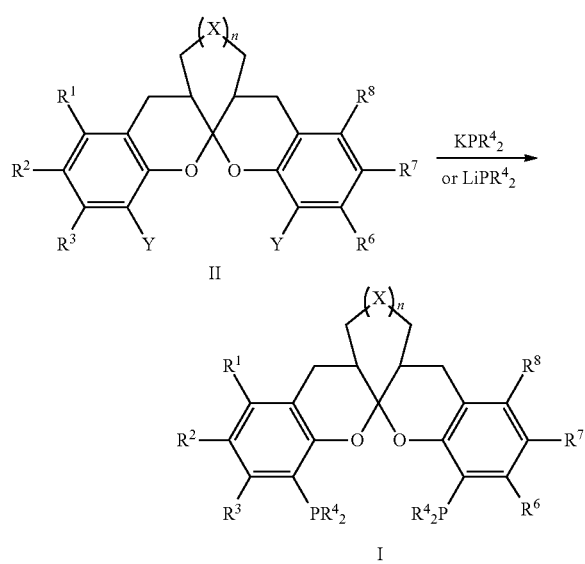

wherein Y is F; and $R^1$, $R^2$, $R^3$, $R^4$, $R^6$, $R^7$, $R^8$, X and n are defined as in claim 1;

or when $R^4$ and $R^5$ are not the same, the preparation method comprises:

(i2) reactin the compound of formula II with $KPR^4_2$ or $LiPR^4_2$ in an organic solvent to form a compound of formula IV; and (ii2) reacting the compound of formula IV with $KPR^5_2$ or $LiPR^5_2$ to form the compound of formula I:

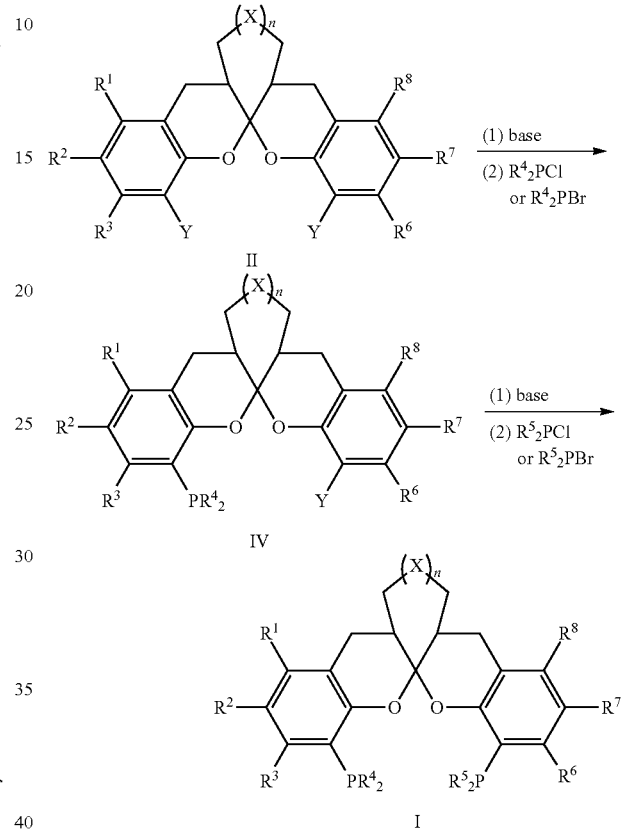

wherein Y is F; and $R^1$, $R^2$, $R^3$, $R^4$, $R^5$, $R^6$, $R^7$, $R^8$, X and n are defined as in claim 1.

3. The preparation method of claim 2, wherein, in step (a3), the mole ratio of the metal catalyst to the compound of formula II is 0.001-0.5:1; and the mole ratio of $R^4_2PH$ to the compound of formula II is 2-10:1.

4. The preparation method of claim 2, wherein the metal catalyst is at least one selected from the group consisting of $Pd(OAc)_2$, $PdCl_2$, $Pd_2(dba)_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$, dpppNiCl$_2$, $Ni(PPh_3)_2Cl_2$, CuI, and a combination thereof.

5. The preparation method of claim 2, wherein the mole ratio of $KPR^4_2$ or $LiPR^4_2$ to the compound of formula II is 2:1-10:1.

6. The preparation method of claim 2, wherein, in step (i2), the mole ratio of $KPR^4_2$ or $LiPR^4_2$ to the compound of formula II is 1:1-1.2:1; and/or in step (ii2), the mole ratio of $KPR^5_2$ or $LiPR^5_2$ to the compound of formula IV is 1:1-1.2:1.

7. The preparation method of claim 1, wherein the synthesis reaction is carried out in an organic solvent, and the organic solvent is benzene, toluene, xylene, dichloromethane, chloroform, carbon tetrachloride, 1,2dichloroethane, diethyl ether, tetrahydrofuran, methanol, ethanol, N,N dimethyl formamide, or dimethyl sulfoxide, or a mixture thereof.

8. The preparation method of claim 1, wherein the Synthesis reaction is carried out in the presence of a base, and the base is selected from the group consisting n butyl lithium, tert-butyl lithium, cyclohexyl lithium, methyl lithium, isopropyl lithium, lithium bis(trimethylsilyl)amide, sodium bis(trimethylsilyl)amide, potassium bis(trimethylsilyl)amide, ethyl magnesium chloride, ethyl magnesium bromide, phenyl magnesium chloride, and phenyl magnesium bromide.

9. A ligand having a structure as shown in general formula I:

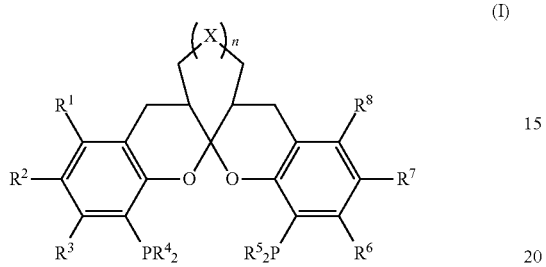

(I)

wherein, $R^1$, $R^2$, $R^3$, $R^6$, $R^7$, and $R^8$ are each independently a hydrogen, a halogen, or a substituted or unsubstituted group selected from the group consisting of a $C_1$-$C_{10}$ alkyl, a $C_1$-$C_4$ alkoxyl, a $C_3$-$C_{30}$ cycloalkyl, and an aryl;

$R^4$ and $R^5$ are each independently a substituted or unsubstituted group selected from the group consisting of a $C_3$-$C_{10}$ cycloalkyl, a $C_1$-$C_{10}$ alkyl, 2-furyl, and an aryl;

X is selected from the group consisting of $CH_2$, NH, $NCH_3$, O, and S; n=0-4;

wherein a substituent for substitution is a halogen, a $C_{1-6}$ alkyl, a $C_{1-6}$ haloalkyl, or a $C_{1-6}$ alkoxyl;

provided that when $R^1$, $R^2$, $R^3$, $R^6$, $R^7$, and $R^8$ are each hydrogen, X is $CH_2$, and n is 1, then $R^4$ and $R^5$ are not both unsubstituted phenyl simultaneously.

10. The ligand according to claim 9, wherein $R^1$, $R^2$, $R^3$, $R^6$, $R^7$, and $R^8$ are each independently selected from the group consisting of a hydrogen, a $C_1$-$C_6$ alkyl, a $C_1$-$C_4$ alkoxyl, a $C_3$-$C_{10}$ cycloalkyl, a phenyl, and a halogen;

$R^4$ and $R^5$ are each independently selected from the group consisting of a substituted phenyl, a $C_3$-$C_6$ cycloalkyl, and a $C_2$-$C_6$ alkyl, and the phenyl is mono-substituted, di-substituted or tri-substituted with one or more substituents selected from the group consisting of a halogen, a $C_{1-6}$ alkyl, a $C_{1-6}$ haloalkyl, and a $C_{1-6}$ alkoxyl; and X is selected from the group consisting of $CH_2$, O, $NCH_3$, and S.

11. The ligand according to claim 9, wherein the ligand is selected from the group consisting of:

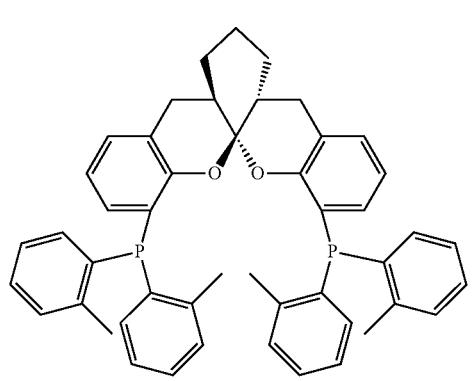

6b

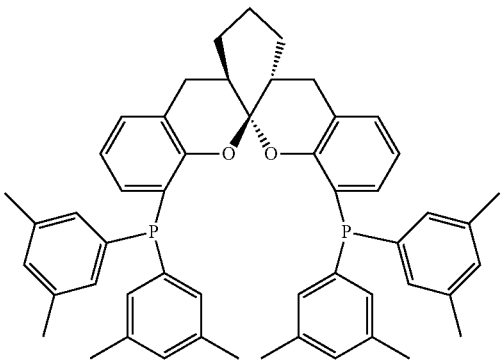

6c

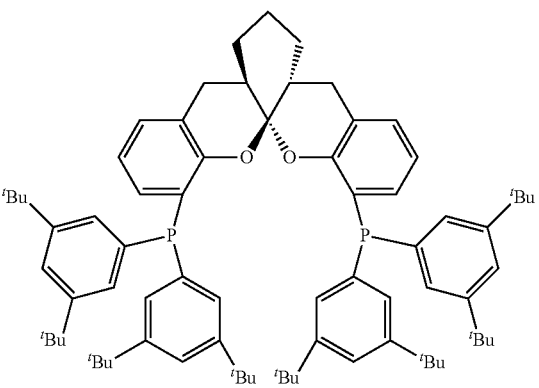

6d

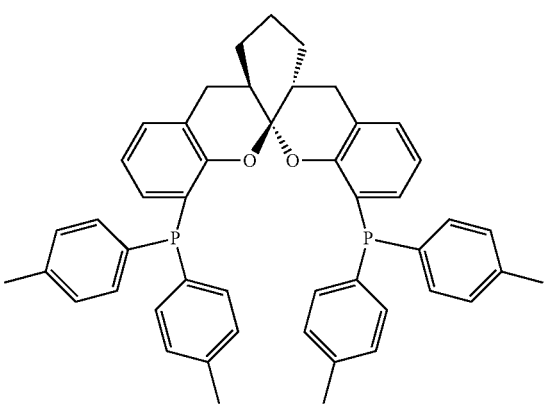

6e

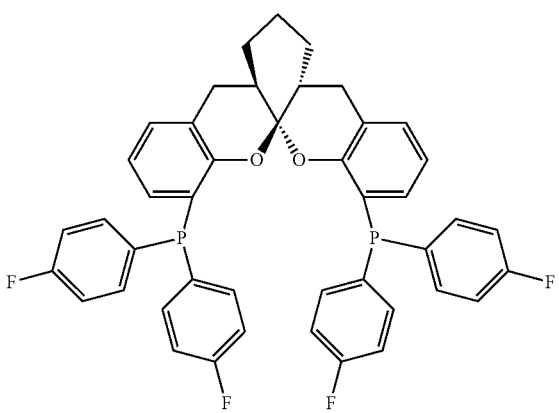

6f

-continued
6g
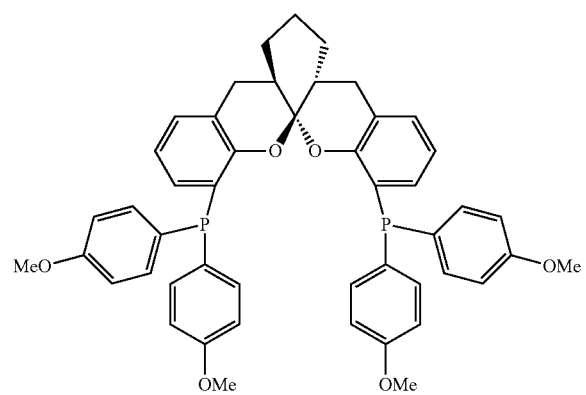
6h
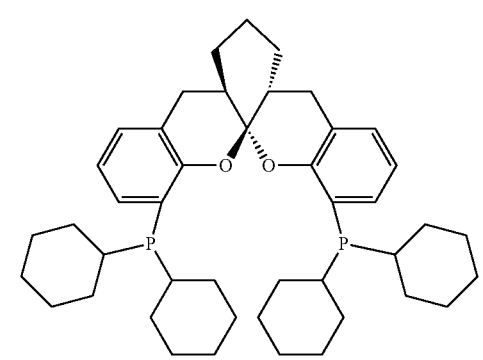
6i
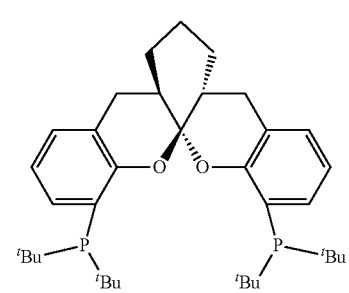
6j
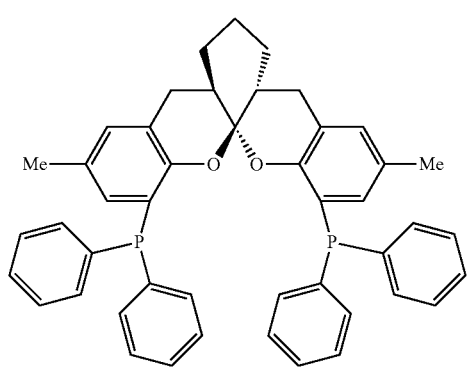
-continued
6k
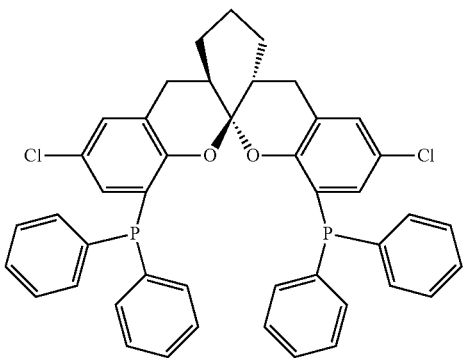
6l
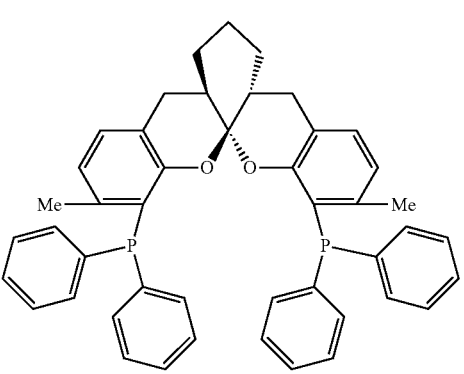
6m
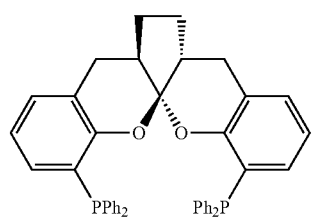
6n
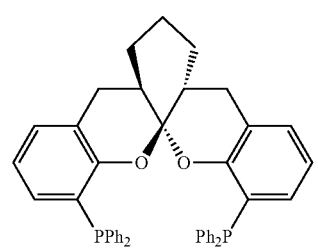
6o
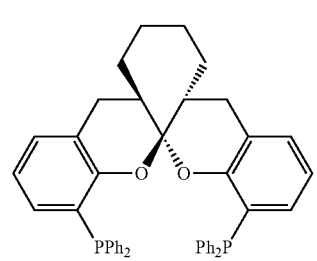

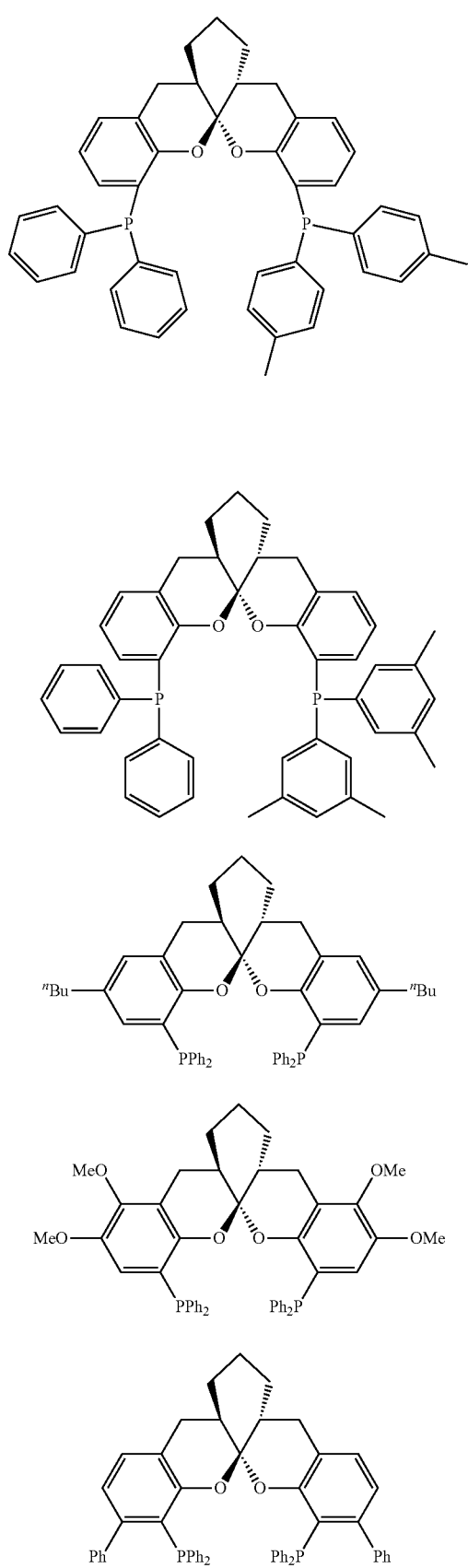
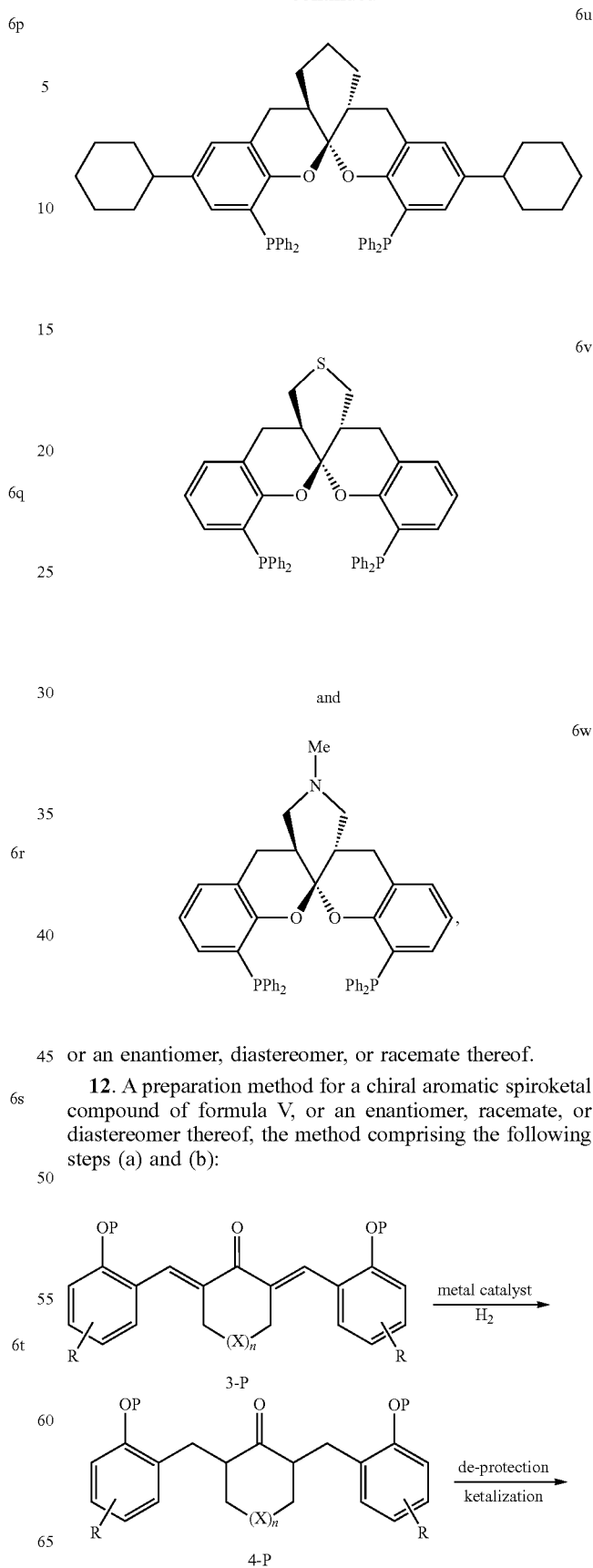
or an enantiomer, diastereomer, or racemate thereof.
12. A preparation method for a chiral aromatic spiroketal compound of formula V, or an enantiomer, racemate, or diastereomer thereof, the method comprising the following steps (a) and (b):

-continued

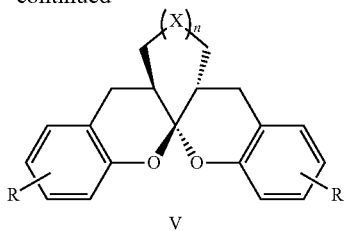

V (a) subjecting a compound of formula 3-P to a catalytic hydrogenation reaction in the presence of a metal complex catalyst in an organic solvent under a hydrogen atmosphere to obtain a compound of formula 4P;
(b) removing the protecting groups P from the compound of formula 4P, and then performing a ketalization reaction to obtain the chiral aromatic spiroketal compound of formula V, wherein X is selected from the group consisting of $CH_2$, NH, $NCH_3$, O, and S; n=0-4; each phenyl ring has one or more R groups, and each R group is independently selected from the group consisting of a hydrogen, a $C_1$-$C_{10}$ alkyl, a $C_1$-$C_4$ alkoxyl, a $C_3$-$C_{30}$ cycloalkyl, a halogen, and an aryl; and P is a methyl, a benzyl, a p-methoxy benzyl, a tert-butyl, a tert-butyldimethylsilyl, a tert-butyldiphenylsilyl, an allyl, a methoxymethyl, a methylthiomethyl, a methoxyethoxymethyl, a benzyloxymethyl, a tetrahydro 2pyranyl, or an ester group.

13. The preparation method of claim 12, wherein the mole ratio of the compound of formula 3-P to the metal complex catalyst is 10000:1-10:1.

14. The preparation method of claim 12, wherein the metal complex catalyst is a complex of metal rhodium, ruthenium, palladium or iridium.

15. The preparation method of claim 12, wherein the metal complex catalyst is a complex of phosphine nitrogen ligand and iridium.

16. The preparation method of claim 12, wherein the catalytic hydrogenation reaction is carried out under 1-100 normal atmospheric pressure of hydrogen at −78-80° C. for 1-48 hrs.

17. The preparation method of claim 12, wherein the said organic solvent is at least one selected from the group consisting of benzene, toluene, xylene, dichloromethane, chloroform, carbon tetrachloride, 1,2dichloroethane, diethyl ether, tetrahydrofuran, methanol, ethanol, N,N-dimethyl formamide, and dimethyl sulfoxide.

18. The preparation method of claim 1, wherein $R^5$ and $R^4$ are the same and the method comprises the following step (a3):

(a3) reacting the compound of formula II with $R^4_2PH$ in an organic solvent and in the presence of a metal catalyst to obtain the compound of formula I:

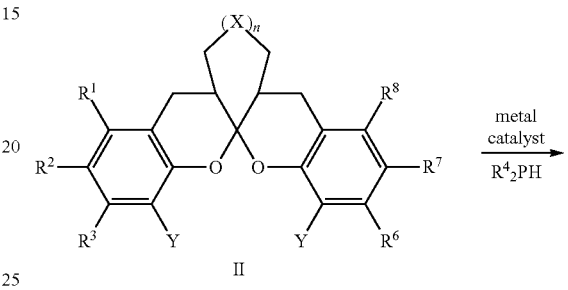

II

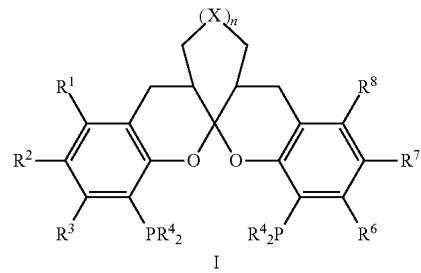

I wherein Y is Cl, Br, or I; and $R^1$, $R^2$, $R^3$, $R^4$, $R^6$, $R^7$, $R^8$, X, and n are defined as in claim 1.

* * * * *